(12) United States Patent
Thurieau et al.

(10) Patent No.: US 7,858,789 B2
(45) Date of Patent: *Dec. 28, 2010

(54) DERIVATIVES OF 4-AMINOPIPERIDINE AND THEIR USE AS A MEDICAMENT

(75) Inventors: Christophe Thurieau, Paris (FR); Jérôme Gonzalez, Annemasse (FR); Christophe Moinet, Montreal (CA)

(73) Assignee: Ipsen Pharma S.A.S., Boulogne-Billancourt (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/151,115

(22) Filed: May 2, 2008

(65) Prior Publication Data

US 2009/0149652 A1    Jun. 11, 2009

Related U.S. Application Data

(62) Division of application No. 11/122,293, filed on May 4, 2005, now Pat. No. 7,393,861, which is a division of application No. 10/130,924, filed as application No. PCT/FR00/03497 on Dec. 13, 2000, now Pat. No. 7,115,634.

(30) Foreign Application Priority Data

Dec. 14, 1999    (FR) .................................. 99 15724

(51) Int. Cl.
    *C07D 401/14*    (2006.01)
(52) U.S. Cl. ...................... 544/360; 546/186; 546/197
(58) Field of Classification Search .................. None
    See application file for complete search history.

(56) References Cited

U.S. PATENT DOCUMENTS 6,756,393 B2 *    6/2004    Andersson et al. ........... 514/352

FOREIGN PATENT DOCUMENTS

| GB | 1 425 354 | 2/1976 |
|----|-----------|--------|
| GB | 1 574 418 | 9/1980 |
| JP | 50-76076 | 6/1975 |
| JP | 53-87365 | 8/1978 |
| WO | WO 99/38514 | 8/1999 |
| WO | WO 00/72834 | 12/2000 |

OTHER PUBLICATIONS

Archibald et al., "Antihypertensive Ureidopiperidines," Journal of Medicinal Chemistry, vol. 23, pp. 857-861 (1980).
Harper et al., "The Chemistry and Pharmacology of Some 4-Aminopiperidines and Their Derivatives," Journal of Medicinal Chemistry, vol. 7, pp. 729-732 (1964).
Hungarian Patent Document No. HU 157325, dated Apr. 8, 1970.

* cited by examiner

*Primary Examiner*—Kamal A Saeed
(74) *Attorney, Agent, or Firm*—Hunton & Williams LLP

(57) ABSTRACT

A subject of the present application is new derivatives of 4-aminopiperidines of formula

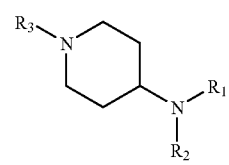

in which $R_1$, $R_2$ and $R_3$ represent various radical, and their preparation processes by synthetic methods in parallel in liquid and solid phase. These products having a good affinity with certain sub-types of somatostatin receptors, they are particularly useful for treating the pathological states or diseases in which one (or more) somatostatin receptors are involved.

1 Claim, No Drawings

DERIVATIVES OF 4-AMINOPIPERIDINE AND THEIR USE AS A MEDICAMENT

PRIOR APPLICATIONS

This application is a division of U.S. patent application Ser. No. 11/122,293 filed May 4, 2005, now U.S. Pat. No. 7,393,861 which is a division of U.S. patent application Ser. No. 10/130,924 filed May 23, 2002, now U.S. Pat. No. 7,115,634 which is a 371 of PCT/FR00/03497 filed Dec. 13, 2000.

A subject of the present application is new derivatives of 4-aminopiperidines and their preparation processes by synthetic methods in parallel in liquid and solid phase. These products having a good affinity with certain sub-types of somatostatin receptors, they are particularly useful for treating the pathological states or diseases in which one (or more) somatostatin receptors are involved.

Somatostatin (SST) is a cyclic tetradecapeptide which was isolated for the first time from the hypothalamus as a substance which inhibits the growth hormone (Brazeau P. et al., Science 1973, 179, 77-79). It also operates as a neurotransmitter in the brain (Reisine T. et al., Neuroscience 1995, 67, 777-790; Reisine T. et al., Endocrinology 1995, 16, 427-442). Molecular cloning has allowed it to be shown that the bioactivity of somatostatin depends directly on a family of five receptors linked to the membrane.

The heterogeneity of the biological functions of somatostatin has led to studies which try to identify the structure-activity relationships of peptide analogues on somatostatin receptors, which has led to the discovery of 5 sub-types of receptors (Yamada et al., Proc. Natl. Acad. Sci. U.S.A, 89, 251-255, 1992; Raynor, K. et al, Mol. Pharmacol., 44, 385-392, 1993). The functional roles of these receptors are currently being actively studied. The affinities with different sub-types of somatostatin receptors have been associated with the treatment of the following disorders/diseases. Activation of sub-types 2 and 5 has been associated with suppression of the growth hormone (GH) and more particularly with that of adenomas secreting GH (acromegalia) and those secreting hormone TSH. Activation of sub-type 2 but not sub-type 5 has been associated with the treatment of adenomas secreting prolactin. Other indications associated with the activation of sub-types of somatostatin receptors are the recurrence of stenosis, inhibition of the secretion of insulin and/or of glucagon and in particular diabetes mellitus, hyperlipidemia, insensibility to insulin, Syndrome X, angiopathy, proliferative retinopathy, Dawn phenomenon and nephropathy; inhibition of the secretion of gastric acid and in particular peptic ulcers, enterocutaneous and pancreaticocutaneous fistulae, irritable colon syndrome, dumping syndrome, aqueous diarrhea syndrome, diarrhea associated with AIDS, diarrhea induced by chemotherapy, acute or chronic pancreatitis and secretory gastrointestinal tumors; the treatment of cancer such as hepatomas; the inhibition of angiogenesis, the treatment of inflammatory disorders such as arthritis; chronic rejection of allografts; angioplasty; the prevention of bleeding of grafted vessels and gastrointestinal bleeding. The agonists of somatostatin can also be used to reduce the weight of a patient.

Among the pathological disorders associated with somatostatin (Moreau J. P. et al., Life Sciences 1987, 40, 419; Harris A. G. et al., The European Journal of Medicine, 1993, 2, 97-105), there can be mentioned for example: acromegalia, hypophyseal adenomas, Cushing's disease, gonadotrophinomas and prolactinomas, catabolic side-effects of glucocorticoids, insulin dependent diabetes, diabetic retinopathy, diabetic nephropathy, hyperthyroidism, gigantism, endocrinic gastroenteropancreatic tumors including carcinoid syndrome, VIPoma, insulinoma, nesidioblastoma, hyperinsulinemia, glucagonoma, gastrinoma and Zollinger-Ellison's syndrome, GRFoma as well as acute bleeding of the esophageal varices, gastroesophageal reflux, gastroduodenal reflux, pancreatitis, enterocutaneous and pancreatic fistulae but also diarrheas, refractory diarrheas of acquired immunodeficiency syndrome, chronic secretary diarrhea, diarrhea associated with irritable bowel syndrome, disorders linked with gastrin releasing peptide, secondary pathologies with intestinal grafts, portal hypertension as well as hemorrhages of the varices in patients with cirrhosis, gastro-intestinal hemorrhage, hemorrhage of the gastroduodenal ulcer, Crohn's disease, systemic scleroses, dumping syndrome, small intestine syndrome, hypotension, scleroderma and medullar thyroid carcinoma, illnesses linked with cell hyperproliferation such as cancers and more particularly breast cancer, prostate cancer, thyroid cancer as well as pancreatic cancer and colorectal cancer, fibroses and more particularly fibrosis of the kidney, fibrosis of the liver, fibrosis of the lung, fibrosis of the skin, also fibrosis of the central nervous system as well as that of the nose and fibrosis induced by chemotherapy, and other therapeutic fields such as, for example, cephaleas including cephalea associated with hypophyseal tumors, pain, panic attacks, chemotherapy, cicatrization of wounds, renal insufficiency resulting from delayed development, obesity and delayed development linked with obesity, delayed uterine development, dysplasia of the skeleton, Noonan's syndrome, sleep apnea syndrome, Graves' disease, polycystic disease of the ovaries, pancreatic pseudocysts and ascites, leukemia, meningioma, cancerous cachexia, inhibition of H pylori, psoriasis, as well as Alzheimer's disease. Osteoporosis can also be mentioned.

The applicants found that the compounds of general formula described hereafter have an affinity and a selectivity for the somatostatin receptors. As somatostatin and its peptide analogues often have a poor bioavailability by oral route and a low selectivity (Robinson, C., Drugs of the Future, 1994, 19, 992; Reubi, J. C. et al., TIPS, 1995, 16, 110), said compounds, non-peptide agonists or antagonists of somatostatin, can be advantageously used to treat pathological states or illnesses as presented above and in which one (or more) somatostatin receptors are involved. Preferably, said compounds can be used for the treatment of acromegalia, hypophyseal adenomas or endocrine gastroenteropancreatic tumors including carcinoid syndrome.

Therefore a subject of the present invention is the compounds of general formula

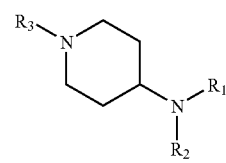

I in racemic, enantiomeric form or all combinations of these forms, in which:

$R_1$ represents a linear or branched $(C_1-C_{16})$alkyl, alkenyl, alkynyl, —$(CH_2)_m$—Y—$Z_{11}$ or —$(CH_2)_m$—$Z_{12}$ radical in which $Z_{11}$ represents a $(C_1-C_6)$alkyl or aryl optionally substituted, $Z_{12}$ represents cyano, cyclohexenyl, bis-phenyl, $(C_3-C_7)$ cycloalkyl, optionally substituted $(C_3-C_7)$ heterocycloalkyl, optionally substituted aryl or optionally substituted heteroaryl, or $Z_{12}$ represents a radical of formula

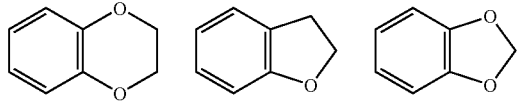

or $R_1$ represents a radical of formula

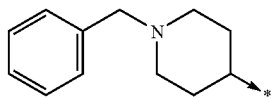

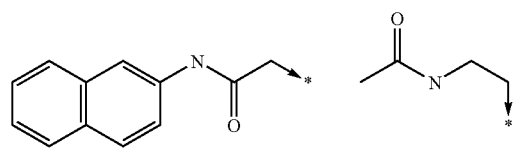

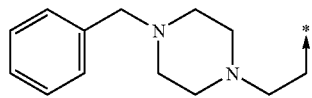

$R_2$ represents a radical of formula —C(Y)NHX$_1$, —C(O)X$_2$ or SO$_2$X$_3$;

$R_3$ represents the hydrogen atom, an optionally substituted alkyl, alkenyl, alkynyl, optionally substituted aralkyl, optionally substituted heteroarylalkyl radical, or a radical of formula —C(Y)—NHX$_1$, —(CH$_2$)$_n$—C(O)X$_2$, SO$_2$X$_3$ or

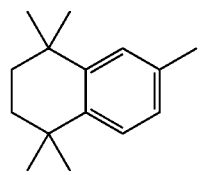

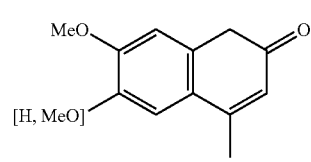

$X_1$ represents a linear or branched $(C_1-C_{15})$alkyl, alkenyl, alkynyl, —$(CH_2)_m$—Y—$Z_{21}$ or —$(CH_2)_p Z_{22}$ radical in which $Z_{21}$ represents a $(C_1-C_6)$alkyl $Z_{22}$ represents cyclohexenyl, indanyl, bis-phenyl, $(C_3-C_7)$ cycloalkyl, $(C_3-C_7)$heterocycloalkyl, mono- or di-alkylamino, —C(O)—O-alkyl, or aryl or heteroaryl optionally substituted, or $Z_{22}$ represents a radical of formula

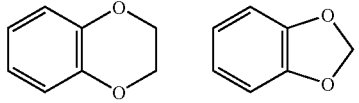

$X_2$ represents a linear or branched $(C_1-C_{10})$alkyl radical, an alkenyl radical optionally substituted by a phenyl radical (the phenyl radical being itself optionally substituted), an alkynyl radical, or a radical of formula —$(CH_2)_m$—W—$(CH_2)_q$—$Z_{23}$ or —$(CH_2)_p$—U—$Z_{24}$ in which $Z_{23}$ represents a $(C_1-C_6)$alkyl or aryl optionally substituted;

$Z_{24}$ represents alkyl, cyclohexenyl, bis-phenyl, $(C_3-C_7)$cycloalkyl optionally substituted, $(C_3-C_7)$heterocycloalkyl, cyano, amino, mono or di-alkylamino, or aryl or heteroaryl optionally substituted, or $Z_{24}$ represents a radical of formula

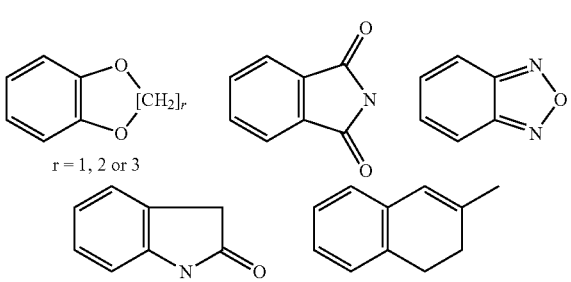

r = 1, 2 or 3 or $X_2$ represents a radical represented below:

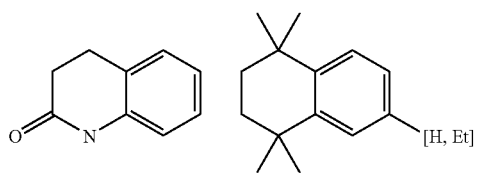

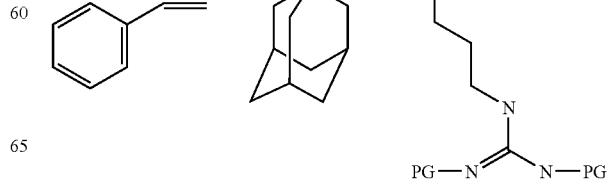

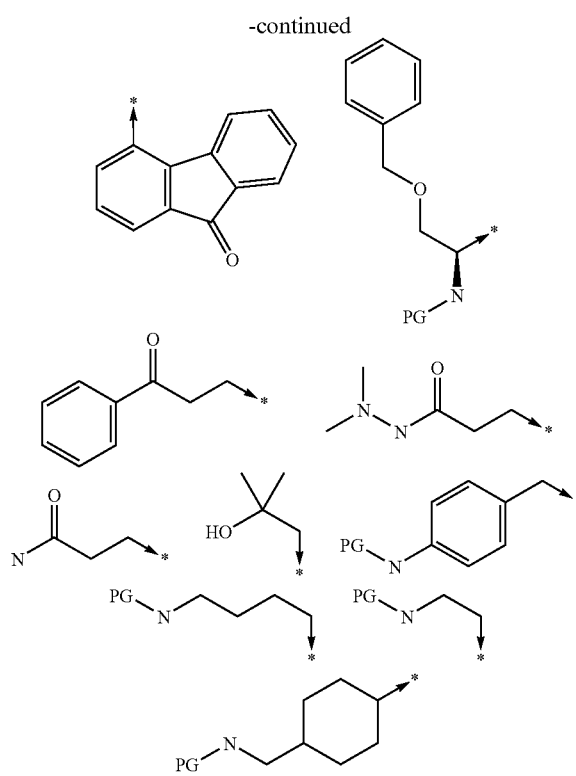

where the protective group (PG) represents H or tert-butyloxycarbonyl;

$X_3$ represents a linear or branched $(C_1-C_{10})$alkyl radical, an alkenyl radical optionally substituted by a phenyl radical (the phenyl radical being itself optionally substituted), $CF_3$, or $-(CH_2)_p Z_{25}$ in which $Z_{25}$ represents aryl or heteroaryl optionally substituted, or $X_3$ represents a radical of formula

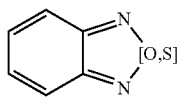

Optionally substituted by one or more halo radicals identical or different;

Y represents an oxygen or sulphur atom;

W represents an oxygen or sulphur atom, or $SO_2$;

U represents a covalent bond or the oxygen atom;

n is an integer from 0 to 4;

m is an integer from 1 to 6;

p is an integer from 0 to 6;

q is an integer from 0 to 2, or their addition salts with pharmaceutically acceptable mineral or organic acids, with the exclusion of compounds of general formula I wherein $R_1$ represents the radical alkyle, alkenyle or benzyle, $R_2$ an optionally substituted benzyloxy and $R_3$ aralkyle.

A more particularly subject of the invention is the products of general formula I as defined above, characterized in that i) the substituent or substituents which can be carried by the aryl radicals represented by $Z_{11}$ and $Z_{12}$ and heteroaryl represented by $Z_{12}$ are chosen independently from the fluoro, chloro, bromo, iodo, alkyl, alkoxy, alkylthio, $-CF_3$, $-OCF_3$, phenyl, phenoxy, aminosulphonyl radicals;

ii) the substituent or substituents which can be carried by the heterocycloalkyl radical represented by $Z_{12}$ are chosen independently from the oxy and alkyl radicals;

iii) the substituent or substituents which can be carried by the aryl and heteroaryl radicals represented by $Z_{22}$ are chosen independently from the fluoro, chloro, bromo, iodo, alkyl, alkenyl, alkoxy, alkylthio, $CF_3$, $OCF_3$, nitro, cyano, azido, aminosulphonyl, piperidinosulphonyl, mono- or di-alkylamino, $-C(O)-O$-alkyl, $-C(O)$-alkyl, or phenyl, phenoxy, phenylthio, benzyloxy radicals, the phenyl radical being able to be substituted;

iv) the substituent or substituents which can be carried by the aryl radicals represented by $Z_{23}$ and $Z_{24}$, cycloalkyl and heteroaryl represented by $Z_{24}$ are chosen independently from the fluoro, chloro, bromo, iodo, alkyl, alkoxy, alkylthio, $CF_3$, $OCF_3$, $OCHF_2$, $SCF_3$, nitro, cyano, azido, hydroxy, $-C(O)$ O-alkyl, $-O-C(O)$-alkyl, $-NH-C(O)$-alkyl, alkylsulphonyl, mono- or di-alkylamino, amino, aminoalkyl, pyrrolyl, pyrrolydinyl or the radicals phenyl, phenoxy, phenylthio, benzyl, benzyloxy radicals the aryl radical of which is optionally substituted by one or more alkyl, $CF_3$ or halo radicals;

v) the substituent or substituents which can be carried by the aryl and heteroaryl radicals represented by $Z_{25}$ are chosen independently from the fluoro, chloro, bromo, iodo, alkyl, alkoxy, $CF_3$, $OCF_3$, nitro, cyano, $-NH-C(O)$-alkyl, alkylsulphonyl, amino, mono- and di-alkylamino, phenyl, pyridino radicals;

vi) the substituent which can be carried by the alkyl radical represented by $R_3$ is the cyano radical;

vii) the substituent or substituents which can be carried by the aralkyl radical represented by $R_3$ are chosen independently from the fluoro, chloro, bromo, iodo, alkyl, alkoxy, $CF_3$, $OCF_3$, $OCHF_2$, $SCF_3$, $SCHF_2$, nitro, cyano, $-C(O)O$-alkyl, alkylsulphonyl, thiadiazolyl radicals, or the phenyl and phenoxy radicals the phenyl radical of which is optionally substituted by one or more halo radicals;

viii) the substituent or substituents which can be carried by the heteroarylalkyl radical represented by $R_3$ are chosen independently from the fluoro, chloro, bromo or nitro radicals.

In the definitions indicated above, the expression halo represents the fluoro, chloro, bromo or iodo radical, preferably chloro, fluoro or bromo. The expression alkyl (when it is not specified otherwise), preferably represents a linear or branched alkyl radical having 1 to 6 carbon atoms, such as the methyl, ethyl, propyl, isopropyl, butyl, isobutyl, sec-butyl and tert-butyl, pentyl or amyl, isopentyl, neopentyl, hexyl or isohexyl radicals. Among the alkyl radicals containing 1 to 15 carbon atoms, there can be mentioned the alkyls as defined above but also the heptyl, octyl, nonyl, decyl, dodecyl, tridecyl or pentadecyl radicals.

By alkenyl, when it is not specified otherwise, is understood a linear or branched alkyl radical containing 1 to 6 carbon atoms and having at least one unsaturation (double bond), such as for example vinyl, allyl, propenyl, butenyl or pentenyl. By alkynyl, when it is not specified otherwise, is understood a linear or branched alkyl radical containing 1 to 6 carbon atoms and having at least one double unsaturation (triple bond) such as for example an ethynyl, propargyl, butynyl or pentynyl radical.

The term cycloalkyl designates a monocyclic carbon system comprising 3 to 7 carbon atoms, and preferably the cyclopropyl, cyclobutyl, cyclopentyl or cyclohexyl rings. The expression heterocycloalkyl designates a saturated cycloalkyl containing 2 to 7 carbon atoms and at least one heteroatom. This radical can contain several identical or different heteroatoms. Preferably, the heteroatoms are chosen from oxygen, sulphur or nitrogen. As examples of a heterocycloalkyl, there can be mentioned the pyrrolidine, pyrrolidinone, imidazolidine, pyrazolidine, isothiazolidine, thiazolidine, isoxazolidine, piperidine, piperazine or morpholine ring.

The alkoxy radicals can correspond to the alkyl radicals indicated above such as for example the methoxy, ethoxy, propyloxy or isopropyloxy radicals but also linear, secondary or tertiary butoxy, pentyloxy. The term lower alkylthio preferably designates the radicals in which the alkyl radical is as defined above such as for example methylthio, ethylthio. The term alkylsulphonyl preferably designates the radicals in which the alkyl radical is as defined above.

The expression aryl represents an aromatic radical, constituted by a condensed ring or rings, such as for example the phenyl or naphthyl radical. The expression heteroaryl designates an aromatic radical, constituted by a ring or condensed rings, with at least one ring containing one or more identical or different heteroatoms chosen from sulphur, nitrogen or oxygen. As an example of a heteroaryl radical, there can be mentioned the thienyl, furyl, pyrrolyl, imidazolyl, pyrazolyl, isothiazolyl, thiazolyl, isoxazolyl, oxazolyl, triazolyl, pyridyl, pyrazinyl, pyrimidyl, quinolyl, isoquinolyl, quinoxalinyl, benzothienyl, benzofuryl, indolyl, benzoxadiazolyl radicals.

The terms mono- and di-alkylamino preferably designate the radicals in which the alkyl radicals are as defined above, such as for example methylamino, ethylamino, dimethylamino, diethylamino or (methyl)(ethyl)amino.

The symbol →* corresponds to the attachment point of the radical. When the attachment site is not specified on the radical, this signifies that the attachment is carried out on one of the sites which are available to this radical for such an attachment.

A more particular subject of the present invention is the compounds of general formula I as defined above in which:

$R_1$ represents a linear or branched $(C_1$-$C_6)$alkyl radical, the $—(CH_2)_m—Y—Z_{11}$ or $(CH_2)_m—Z_{12}$ radical in which
  $Z_{11}$ represents a $(C_1$-$C_6)$alkyl,
  $Z_{12}$ represents bis-phenyl, $(C_3$-$C_7)$cycloalkyl, $(C_3$-$C_7)$heterocycloalkyl optionally substituted, or aryl or heteroaryl optionally substituted by one or more substituents chosen independently from the fluoro, chloro, bromo, iodo, alkyl, alkoxy radicals,
  or $Z_{12}$ represents

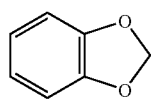

Y represents the oxygen atom,
or $R_1$ represents a radical of formula

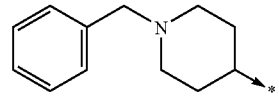

$R_2$ represents a radical of formula $—C(Y)NHX_1$, $—C(O)X_2$ or $SO_2X_3$ in which
  $X_1$ represents a linear or branched $(C_1$-$C_{15})$alkyl radical, or $—(CH_2)_pZ_{22}$ in which
    $Z_{22}$ represents cyclohexenyl, bis-phenyl, $(C_3$-$C_7)$cycloalkyl, $(C_3$-$C_7)$heterocycloalkyl, mono- or di-alkylamino, $—C(O)—O$-alkyl, or aryl or heteroaryl optionally substituted by one or more radicals chosen independently from the fluoro, chloro, bromo, iodo, alkyl, alkoxy, alkylthio, $CF_3$, $OCF_3$, nitro, cyano, azido, piperidinosulphonyl, $—C(O)—O$-alkyl, $—C(O)$-alkyl, or phenyl radicals,
    or $Z_{22}$ represents a radical of formula

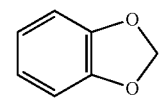

$X_2$ represents a linear or branched $(C_1$-$C_{10})$alkyl, alkynyl, $—(CH_2)_m—W—(CH_2)_q—Z_{23}$ or $—(CH_2)_p—U—Z_{24}$ radical in which
  W represents $SO_2$,
  U represents a covalent bond,
  $Z_{23}$ represents an aryl radical;
  $Z_{24}$ represents cyclohexenyl, bis-phenyl, $(C_3$-$C_7)$cycloalkyl optionally substituted by an aminoalkyl, or aryl or heteroaryl radical optionally substituted by one or more radicals chosen from fluoro, chloro, bromo, iodo, alkyl, alkoxy, $—CF_3$, $—OCF_3$, $SCF_3$, hydroxy, $—O—C(O)$-alkyl, mono- or di-alkylamino, amino
  or $Z_{24}$ represents a radical of formula

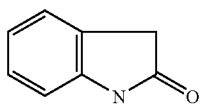 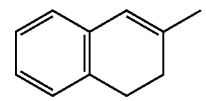

or $X_2$ represents

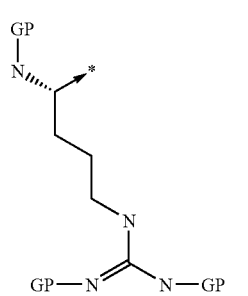 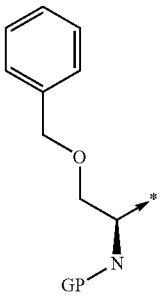

$X_3$ represents a -$(CH_2)_pZ_{25}$ radical in which $Z_{25}$ represents an aryl radical optionally substituted by one or more identical or different radicals chosen from alkoxy and $CF_3$, $R_3$ represents the hydrogen atom, an alkyl, alkenyl, heteroarylalkyl radical optionally substituted or a radical of formula —C(Y)—$NHX_1$, —C(O)$X_2$ or $SO_2X_3$ in which $X_1$ represents a —$(CH_2)_pZ_{22}$ radical in which $Z_{22}$ represents an aryl radical optionally substituted by one or more radicals chosen independently from the fluoro, chloro, bromo, iodo, alkyl, alkoxy, $CF_3$, nitro, phenoxy radicals;

$X_2$ represents the vinyl radical substituted by a phenyl, the phenyl radical being itself optionally substituted by one or more halo, or —$(CH_2)_p$—U—$Z_{24}$ radicals in which $Z_{24}$ represents alkyl, $(C_3$-$C_7)$cycloalkyl, $(C_3$-$C_7)$heterocycloalkyl, bis-phenyl, amino, mono or di-alkylamino, or aryl or heteroaryl optionally substituted by one or more radicals chosen from alkoxy, bromo, chloro, fluoro, hydroxy, $CF_3$, nitro, amino, mono- and di-alkylamino, pyrrolyl, or $X_2$ represents a radical of formula

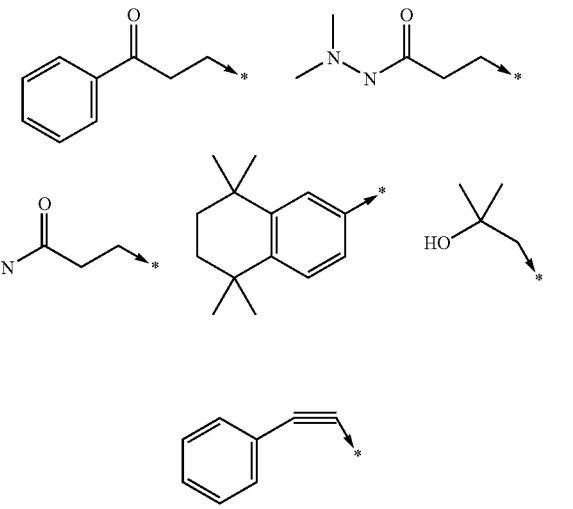

$X_3$ represents a linear or branched $(C_1$-$C_{10})$alkyl radical, the vinyl radical substituted by a radical (the phenyl radical being itself optionally substituted). $CF_3$, or —$(CH_2)_pZ_{25}$ in which $Z_{25}$ represents aryl or heteroaryl optionally substituted by one or more substituents chosen independently from the fluoro, chloro, bromo, iodo, alkyl, alkoxy, $CF_3$, nitro, —NH—C(O)-alkyl, mono- and di-alkylamino radicals.

Preferentially, $R_1$ represents a linear or branched $(C_1$-$C_6)$ alkyl radical, the $(CH_2)_m$—Y—$Z_{11}$ or —$(CH_2)_m$—$Z_{12}$ radical in which $Z_{11}$ represents a $(C_1$-$C_6)$alkyl, $Z_{12}$ represents naphthyl, morpholino, bis-phenyl, pyrrolidinyl substituted by the oxy radical, or the phenyl, piperazinyl, pyridinyl and indolyl radicals which are optionally substituted by one or more substituents chosen independently from the bromo, fluoro, chloro, alkyl, alkoxy, —$CF_3$, —$OCF_3$ radicals;

or $Z_{12}$ represents

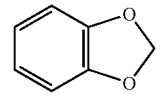

Y represents the oxygen atom, or $R_1$ represents a radical of formula given below:

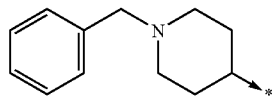

Preferentially, $R_2$ represents a radical of formula —C(Y) $NHX_1$, —C(O)$X_2$ or $SO_2X_3$ in which $X_1$ represents a linear or branched $(C_1$-$C_{10})$alkyl, or —$(CH_2)_pZ_{22}$ radical in which $Z_{22}$ represents cyclohexyl, cyclohexenyl, bis-phenyl, morpholino, piperidino, mono- or di-alkylamino, —C(O)—O-alkyl, or phenyl, naphthyl or furyl optionally substituted by one or more radicals chosen independently from the fluoro, chloro, bromo, iodo, alkyl, alkoxy, alkylthio, $CF_3$, $OCF_3$, nitro, cyano, azido, piperidinosulphonyl, —C(O)—O-alkyl, —C(O)-alkyl or phenyl radicals, or $Z_{22}$ represents a radical of formula

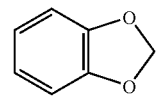

$X_2$ represents an alkyl, alkynyl, —$(CH_2)_m$—W—$(CH_2)_q$—$Z_{23}$ or —$(CH_2)_pZ_{24}$ radical in which W represents $SO_2$;

$Z_{23}$ represents the phenyl radical;

$Z_{24}$ represents cyclohexenyl, bis-phenyl, cyclohexyl optionally substituted by an aminoalkyl, or phenyl, naphthyl, benzothienyl, thienyl or indolyl radical optionally substituted by one or more radicals chosen from fluoro, chloro, bromo. Iodo, alkyl, alkyl, —$CF_3$, —$OCF_3$, $SCF_3$, hydroxy, —O—C(O)-alkyl, —NH—C(O)-alkyl, mono- or di-alkylamino, amino, or $Z_{24}$ represents a radical of formula

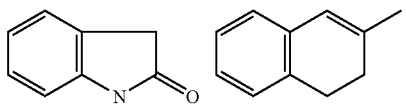

or $X_2$ represents

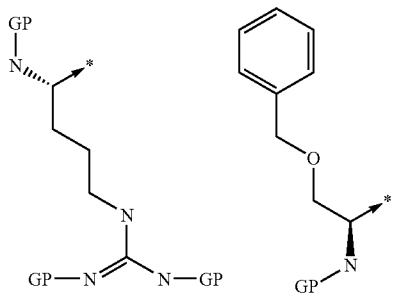

$X_3$ represents a —$(CH_2)_pZ_{25}$ radical in which $Z_{25}$ represents the phenyl radical optionally substituted by one or more identical or different radicals chosen from alkoxy and $CF_3$, Preferentially, $R_3$ represents the hydrogen atom, an alkyl, alkenyl or furyl-methyl radical substituted by one or more nitro radicals, or a radical of formula —C(Y)—$NHX_1$, —C(O)$X_2$ or $SO_2X_3$ in which $X_1$ represents a —$(CH_2)_pZ_{22}$ radical in which
$Z_{22}$ represents the phenyl or naphthyl radical optionally substituted by one or more radicals chosen independently from the fluoro, chloro, bromo, iodo, alkyl, alkoxy, $CF_3$, nitro, phenoxy radicals, $X_2$ represents the vinyl radical substituted by a phenyl radical itself optionally substituted by one or more halo, or —$(CH_2)_p$—U—$Z_{24}$ radicals in which
$Z_{24}$ represents alkyl, cyclohexyl, tetrahydrofuryl, bis-phenyl, amino, mono or di-alkylamino, or phenyl, indolyl, thienyl, pyridinyl, benzothienyl and furyl optionally substituted by one or more radicals chosen from alkoxy, bromo, chloro, fluoro, amino, mono- and di-alkylamino, nitro, hydroxy, pyrrolyl
or $X_2$ represents a radical of formula

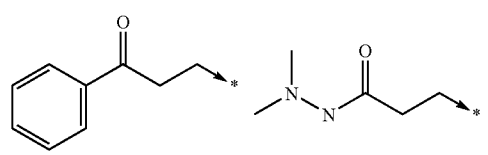

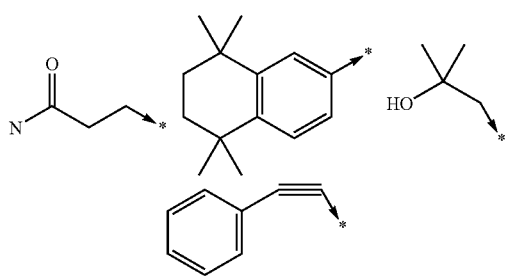

$X_3$ represents a linear or branched ($C_1$-$C_{10}$)alkyl radical, the vinyl radical substituted by a phenyl, $CF_3$, or —$(CH_2)_pZ_{25}$ radical in which
$Z_{25}$ represents a phenyl, naphthyl, thienyl, pyrazolyl or thiazolyl radical optionally substituted by one or more substituents chosen independently from the fluoro, chloro, bromo, iodo, alkyl, alkoxy, $CF_3$, nitro, —NH—C(O)-alkyl, mono- and di-alkylamino radicals;

Very preferentially, $R_1$ represents the —$(CH_2)_mZ_{12}$ radical in which m=2 and $Z_{12}$ represents bis-phenyl or the radical indolyl substituted by one or more substituents chosen independently from the alkyl and alkoxy radicals.

Very preferentially, $R_2$ represents the radicals of formula —C(Y)$NHX_1$ and —C(O)$X_2$ in which
Y represents S;
$X_1$ represents a phenyl radical optionally substituted by one or more azido radicals,
$X_2$ represents —$(CH_2)_pZ_{24}$ in which
p is equal to 1, 2 or 3,
$Z_{24}$ represents cyclohexyl, or phenyl or benzothienyl optionally substituted by one or more radicals chosen from fluoro, chloro, bromo, iodo or —$CF_3$.

Very preferentially, $R_3$ represents the hydrogen atom or the methyl radical.

The compounds according to the invention can be prepared in solid or liquid phase.

A) Syntheses in Liquid Phase Via the N-Substituted Piperidone

A1) Reducing Amination

It is carried out according to the following stage:

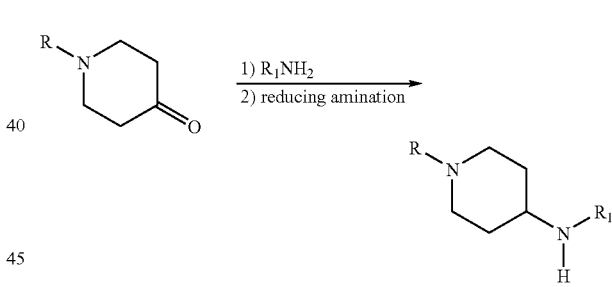

in which R represents methyl or Boc and $R_1$ has the meaning indicated above.

The general procedure is as follows: the reducing amination (Abdel-Magid. A. F.; Maryanoff, C. A.; Carson, K. G. *Tetrahedron Lett.* 1990, 31, 5595-5598; Abdel-Magid, A. F.; Carson, K. G.; Harris, B. D.; Maryanoff, C. A.; Shah, R. D., *J. Org. Chem.* 1996, 61, 3849-3862) of the N-substituted piperidone is carried out in anhydrous chlorinated solvents such as dichloroethane in the presence of a primary amine (1.1 to 1.5 eq.), a reducing agent such as sodium triacetoxyborohydride (1.1 to 1.5 eq.) and acetic acid (10% by mass relative to the N-substituted piperidone). The reaction mixture is agitated for 1 to 4 hours at ambient temperature. In certain cases, a solution of soda (0.1 M) is added and the mixture is agitated for 20 to 90 minutes. If not, the reaction mixture is washed with a saturated solution of sodium bicarbonate, with sodium chloride, dried over magnesium sulphate, filtered and concentrated. The desired product is purified by flash chromatography on silica gel.

Preparation 1: tert-butyl 4-[(3,3-diphenylpropyl)amino]-1-piperidine carboxylate($C_{25}H_{34}N_2O_2$, M=394.56)

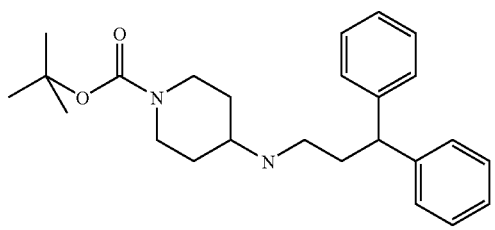

3,3-diphenylpropylamine (5.8 g, 27.5 mmol), sodium triacetoxyborohydride (6.36 g, 30 mmol) and 0.5 ml of acetic acid are added to 5 g (25 mmol) of N-Boc-piperidone in 100 ml of dry dichloroethane. The turbid yellow solution is agitated at ambient temperature 1 hour 1 hour. 50 ml of a soda solution (0.1 M) is then added and the mixture is agitated for 30 minutes. The organic phase is washed with a saturated solution of sodium bicarbonate, with sodium chloride, dried over magnesium sulphate, filtered and concentrated in order to produce 10 g of a yellow solid. This solid is purified by flash chromatography on silica gel eluting with a heptane/ethyl acetate mixture (4/1, 3/1, 2/1 then 1/1) then with pure ethyl acetate. The fractions are concentrated under vacuum in order to produce 5.6 g (yield=57%) of a pale yellow solid.

NMR $^1H(CD_3OD$, 400 MHz) δ: 7.27 (m, 8H); 7.16 (m, 2H); 4 (dd, J=6.4 and 14 Hz, 3H); 2.73 (m, 2H); 2.55 (m, 3H); 2.26 (q, J=7.6 Hz, 2H); 1.78 (d, J=12 Hz, 2H); 1.45 (s, 9H); 1.15 (qd, J=4.4 and 12.8 Hz, 2H). MS/LC: m/z=395.2 (M+H).

A series of 4-aminosubstituted-1-piperidine was prepared according to this procedure with the following other $R_1$ groups:

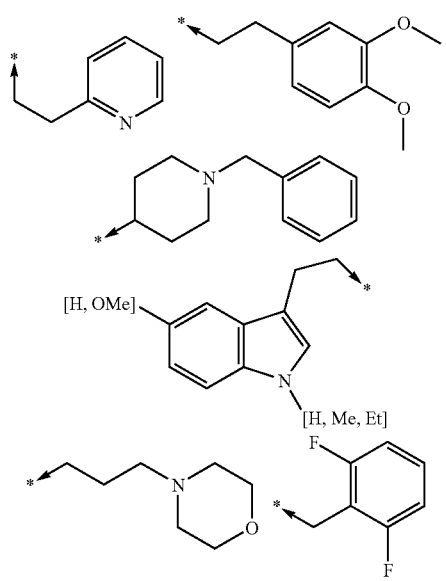

A2) Functionalization of Piperidines

A2a) Syntheses of Ureas and Thioureas

The syntheses of ureas and thioureas are implemented according to the procedure described in the literature (Kaldor, S. W.; Siegel, M. G.; Fritz, J. E.; Dressman, B. A.; Hahn, P. J. *Tetrahedron Lett.* 1996, 37, 7193-7196; Kaldor, S. W.; Fritz, J. E.; Tang, J.; McKinney, E. R. *Bioorg. Med. Chem. Lett.* 1996, 6, 3041-3044; Booth, R. J.; Hodges, J. C. *J. Am. Chem. Soc.* 1997, 119, 4882-4886; Flynn. D. L.; Crich, J. Z.; Devraj, R. V.; Hockerman, S. L.; Parlow, J. J.; South. M. S.; Woodard, S.; *J. Am. Chem. Soc.* 1997, 119, 4874-4881) following the following diagram:

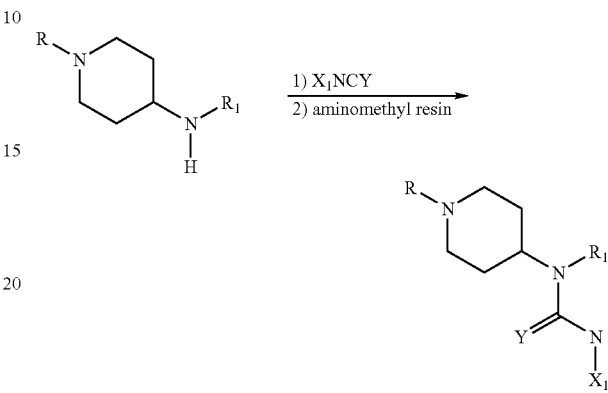

in which R represents methyl or Boc and $X_1$ and Y have the meaning indicated above. It should be noted that in the case where R represents Boc, the product thus obtained is a final product corresponding to formula I according to the invention but can also be used as a synthesis intermediate.

The general procedure is as follows: the isocyanate or the isothiocyanate (1.1 to 1.5 eq.) is added to the 4-aminosubstituted-1-piperidine in aprotic solvents such as dichloromethane, tetrahydrofuran or dimethylformamide and the mixture is agitated for 45 minutes to 18 hours at ambient temperature. The aminomethyl resin (Novabiochem, 1.33 mmol/g, 0.2 to 1 eq.) is added and the mixture is agitated for 45 minutes to 18 hours. In certain cases, the basic ion exchange resin such as IRA-68 (Gayo, L. M.; Suto, M. J. *Tetrahedron Lett.* 1997, 38, 513-516) can be added. The resins are filtered and the filtrate is concentrated. Other purifications on silica gel or basic alumina cartridges (500 mg, Interchim) can optionally be carried out.

EXAMPLE A2a tert-butyl-4-((3,3-diphenylpropyl) {[3-(trifluoromethyl)anilino]carbonyl}amino)-1-piperidine carboxylate ($C_{33}H_{38}F_3N_3O_3$, M=581.68)

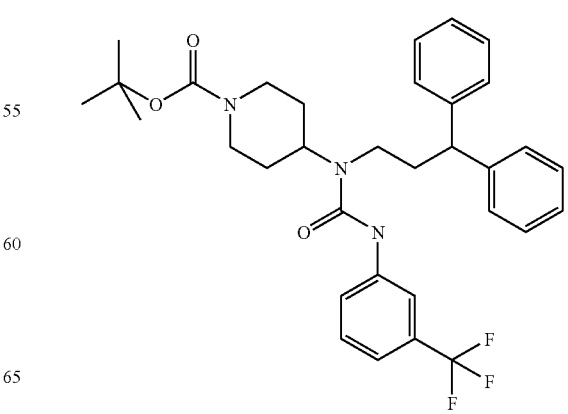

246 mg (1.32 mmol) of 3-(trifluoromethyl)phenyl isocyanate is added to a solution of tert-butyl 4-[(3,3-diphenylpropyl)amino]-1-piperidine carboxylate (470 mg, 1.2 mmol) in 5 ml of dichloromethane. The solution is agitated for 45 minutes, and the aminomethyl resin (180 mg, 0.36 mmol) is added and the reaction medium is again placed on an orbital shaker for 45 minutes. The resin is filtered and washed with dichloromethane. The filtrate is concentrated in vacuo in order to produce 610 mg (yield=87%) of a white foam.

NMR $^1$H(CD$_3$OD, 400 MHz) δ: 7.71 (s, 1H); 7.57 (d, 1H); 7.43 (t, 1H); 7.26 (m, 10H) 7.15 (m, 1H); 4.1 (m, 3H); 3.97 (dd, J=7.6 and 10 Hz, 1H); 3.17 (m, 2H); 2.75 (m, 2H); 2.35 (m, 2H); 1.65 (d, J=12 Hz, 2H); 1.46 (s, 9H, tbutyl group); 1.39 (dd. J=2.4 and 10.8 Hz, 2H); 1.29 (s, 1H). MS/LC: m/z=582 (M−H).

For the R$_1$ groups as illustrated in point A1 above, the X$_1$ groups which can be envisaged for the synthesis of ureas (Y=O) according to the above procedure, are the following:

For the $R_1$ groups as illustrated in point A1 above, the $X_1$ groups which can be envisaged for the synthesis of thioureas (Y=S) according to the above procedure, are the following:

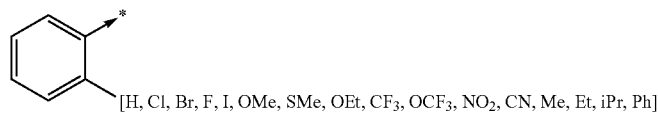
[H, Cl, Br, F, I, OMe, SMe, OEt, CF$_3$, OCF$_3$, NO$_2$, CN, Me, Et, iPr, Ph]

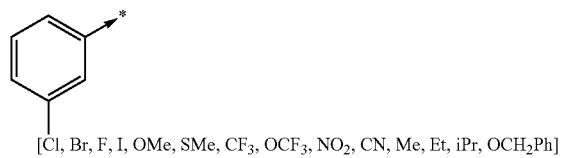
[Cl, Br, F, I, OMe, SMe, CF$_3$, OCF$_3$, NO$_2$, CN, Me, Et, iPr, OCH$_2$Ph]

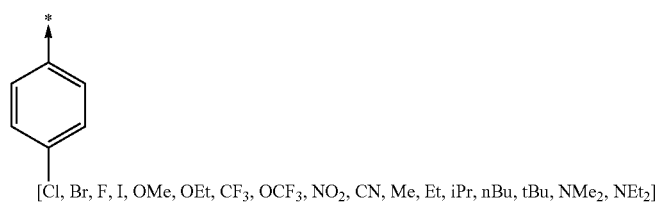
[Cl, Br, F, I, OMe, OEt, CF$_3$, OCF$_3$, NO$_2$, CN, Me, Et, iPr, nBu, tBu, NMe$_2$, NEt$_2$]

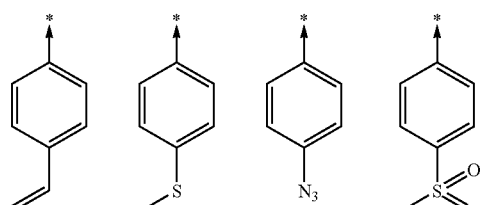

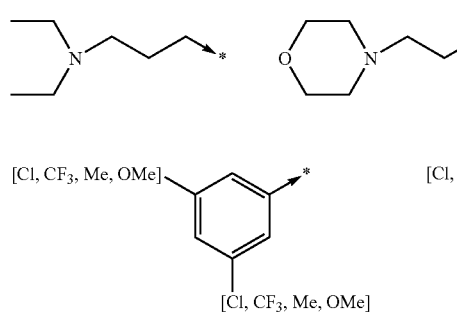

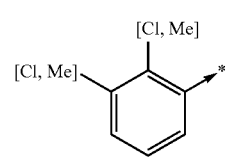

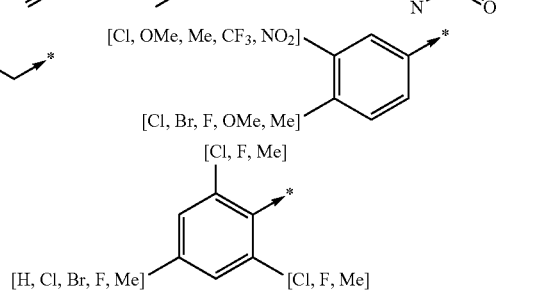
[Cl, OMe, Me, CF$_3$, NO$_2$]
[Cl, Br, F, OMe, Me]

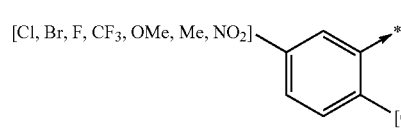
[Cl, CF$_3$, Me, OMe]
[Cl, CF$_3$, Me, OMe]

[Cl, Me]
[Cl, F, Me]

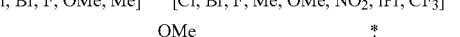
[H, Cl, Br, F, Me]  [Cl, F, Me]

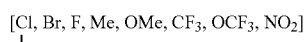

[Cl, Br, F, Me, OMe, CF$_3$, OCF$_3$, NO$_2$]

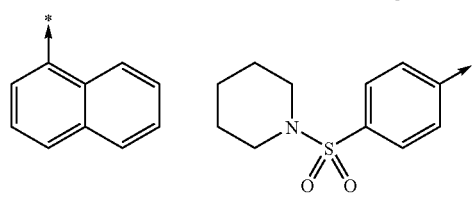
[Cl, Br, F, CF$_3$, OMe, Me, NO$_2$]
[Cl, Br, F, OMe, Me]   [Cl, Br, F, Me, OMe, NO$_2$, iPr, CF$_3$]

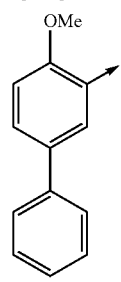

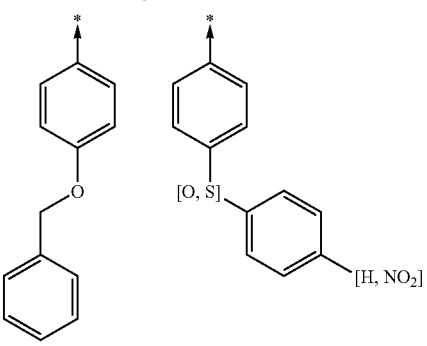
[O, S]
[H, NO$_2$]

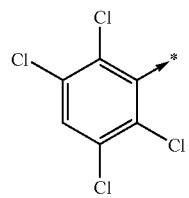

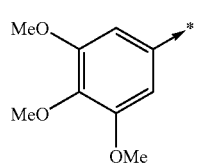

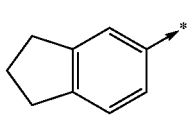

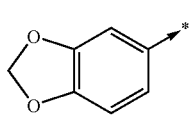

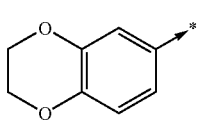

-continued
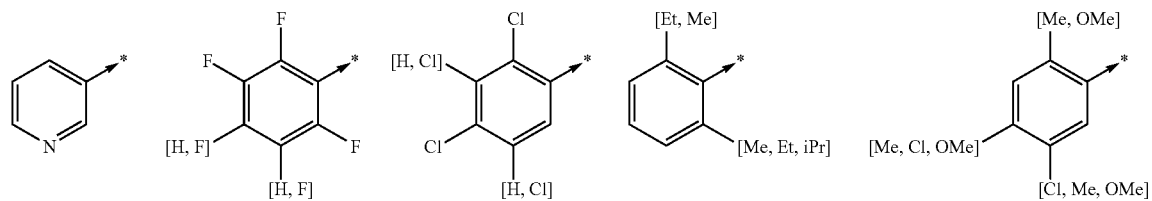
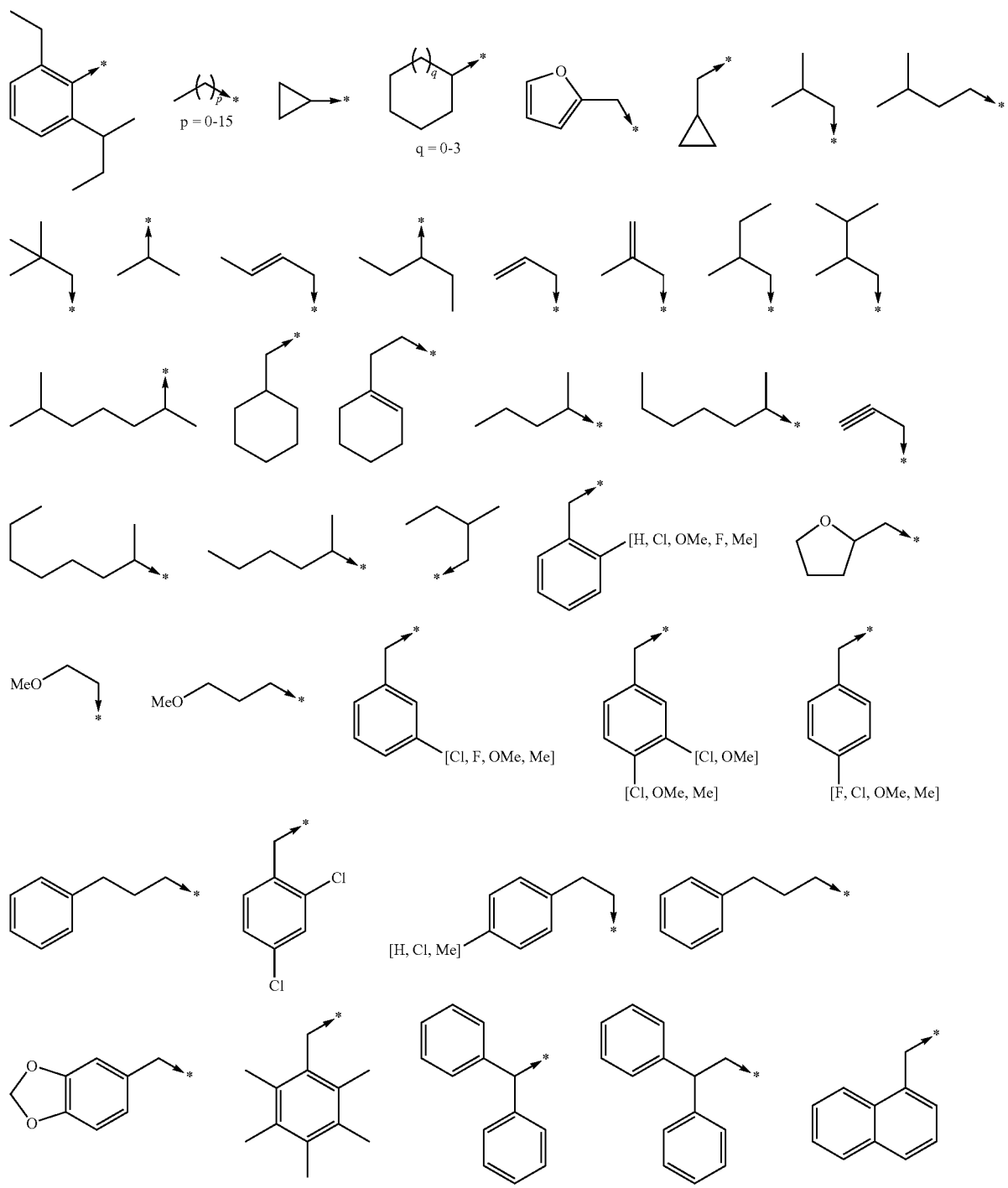

-continued

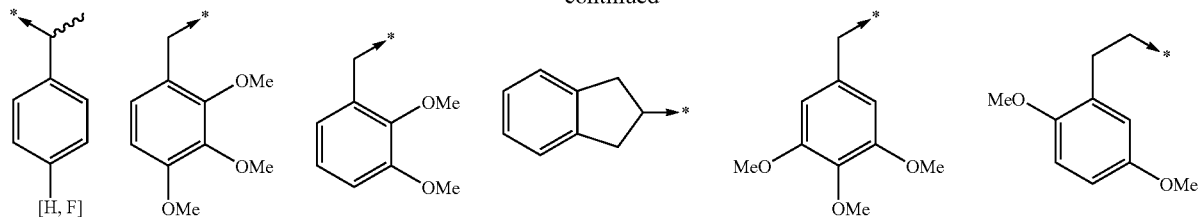

A2b) Synthesis of Amides from Carboxylic Acids

The syntheses of amides from carboxylic acids are implemented according to the following reaction diagram:

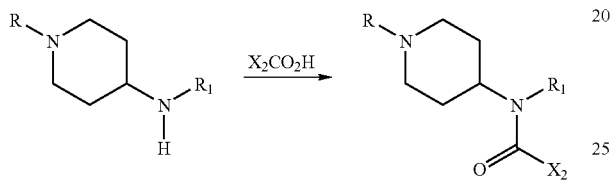

in which R represents methyl or Boc and $X_2$ has the meaning indicated above. It should be noted that in the case where R represents Boc, the product thus obtained is a final product corresponding to formula I according to the invention but can also be used such as a synthesis intermediate.

The general procedure is as follows: carboxylic acid (1.1 to 2.5 eq.) dissolved in an anhydrous aprotic solvent such as dichloromethane, dimethylformamide or tetrahydrofuran is activated with 1-ethyl-3-(3-dimethylaminopropyl) carbodiimide bonded on resin (P-EDC, Novabiochem, 2.33 mmol/g, 1.3 to 3 eq.) (Desai, M. C. Stephens Stramiello, L. M. *Tetrahedron Lett.* 1993, 34, 7685-7688). This mixture is agitated for 5 to 30 minutes at ambient temperature. 4-aminosubstituted-1-piperidine dissolved beforehand in an anhydrous aprotic solvent such as dichloromethane, dimethylformamide or tetrahydrofuran is then added and the reaction mixture is agitated at ambient temperature for 1 to 18 hours. In certain cases, basic ion exchange resin (IRA-68, SAX) is added and the mixture is again agitated at ambient temperature for 1 to 18 hours. The resins are filtered on frit or on a basic ion exchange resin cartridge (IRA-68, SAX) or on an alumina cartridge (500 mg, Interchim).

EXAMPLE A2b tert-butyl 4-{(3,4-dimethoxyphenethyl)[2-(1H-indol-3'-yl)acetyl]amino}-1-piperidine carboxylate ($C_{35}H_{41}N_3O_3$, M=551.74)

512 mg (1.12 mmol, 1.4 eq.) of P-EDC resin is preswollen in dichloromethane. 2-(1H-indol-3-yl)acetic acid (153 mg, 0.875 mmol, 1.1 eq.) is added and the mixture is agitated for 10 minutes. Tert-butyl 4-[(3,3-diphenylpropyl)amino]-1-piperidine carboxylate (292 mg, 0.8 mmol) in tetrahydrofuran is added and the reaction medium is agitated overnight. 2 spatulas of basic ion exchange resin IRA-68 are added and the reaction medium is again agitated overnight. The resins are filtered and the filtrate is concentrated under vacuum in order to produce 250 mg (yield=86%) of a pale yellow foam.

NMR $^1$H(CD$_3$OD, 400 MHz) δ: 7.63 (d, J=8 Hz, 1H); 7.44 (d, J=8 Hz, 1H); 7.36 (d, J=8 Hz, 1H); 7.26 (d, J=8 Hz, 1H); 7.2 (m, 6H); 7.13 (m, 3H); 7.1 (m, 2H); 6.68 (s, 1H); 4-3.75 (m, 4H); 3.65 (s, 1H); 3.2 (m, 1H); 3 (m, 1H); 2.75 (m, 1H); 2.26 (m, 3H); 1.6 (m, 2H); 1.44 (s, 9H); 1.13 (m, 2H). MS/LC: m/z=552.4 (M+H).

A series of amides was synthesized according to this procedure. The $X_2$ radicals which can be envisaged are the following:

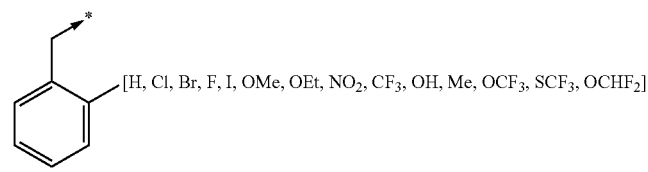

-continued
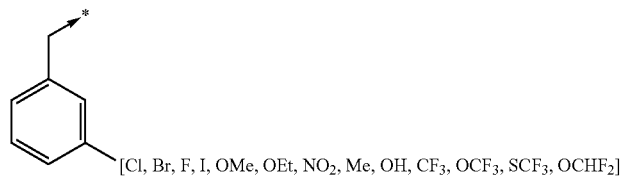
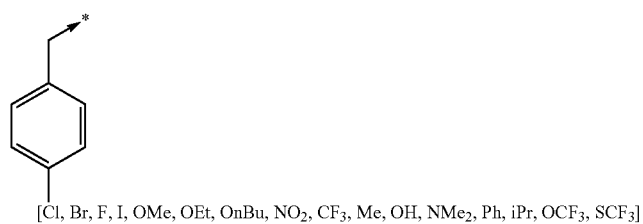
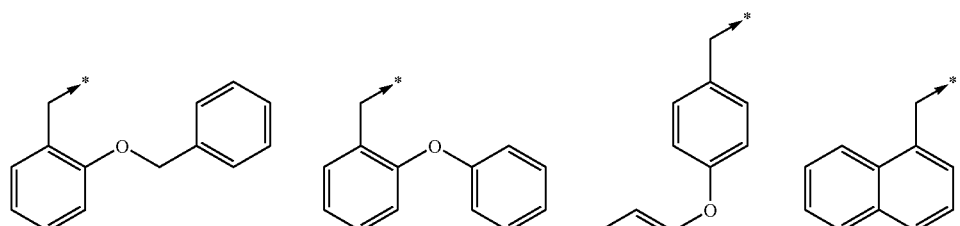
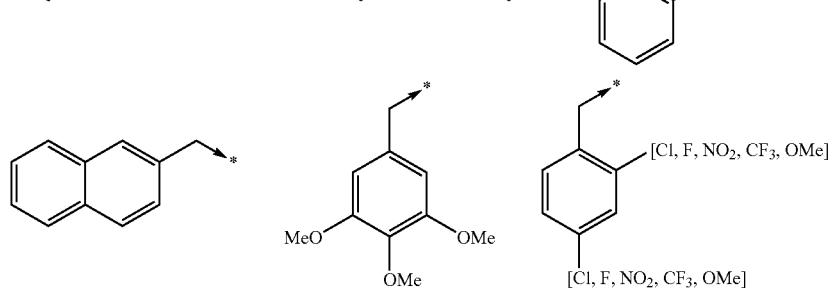
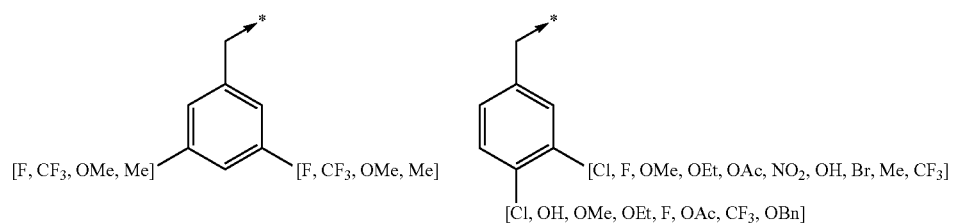
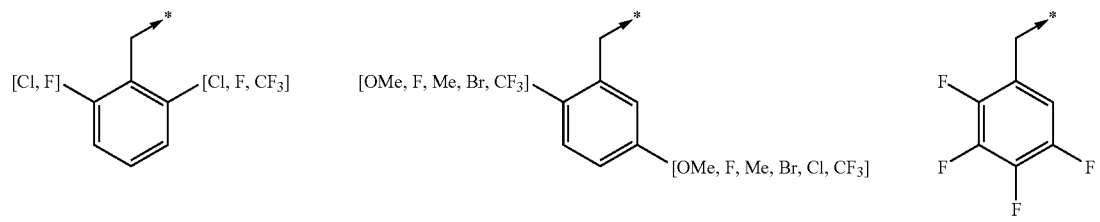
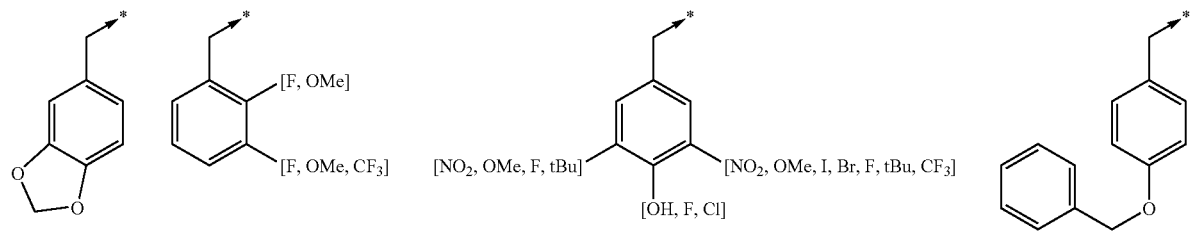

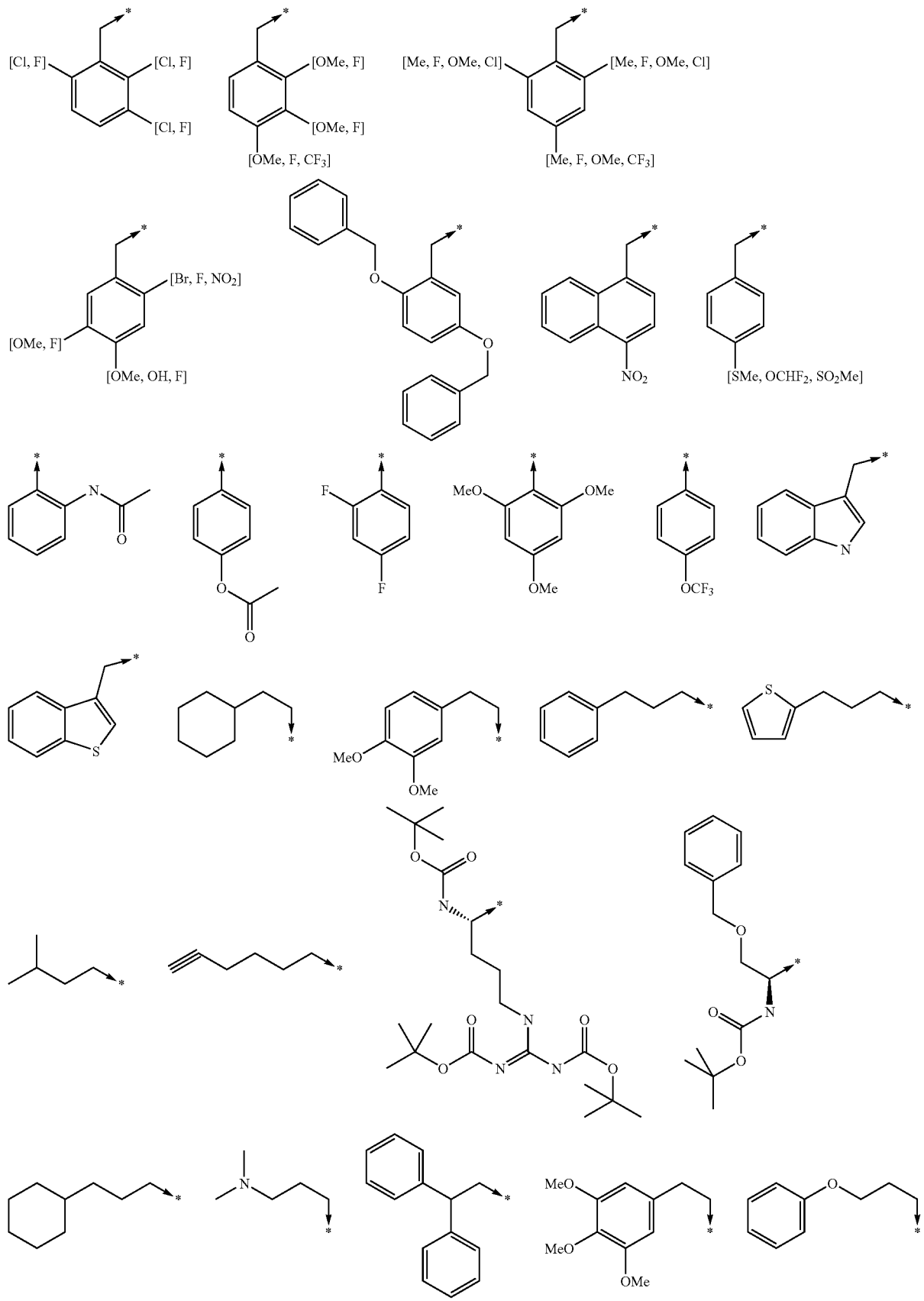

-continued

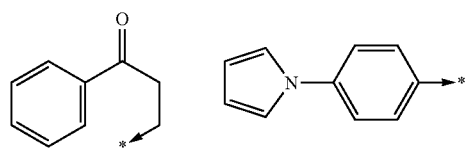
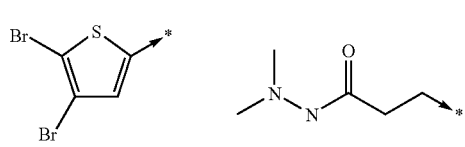
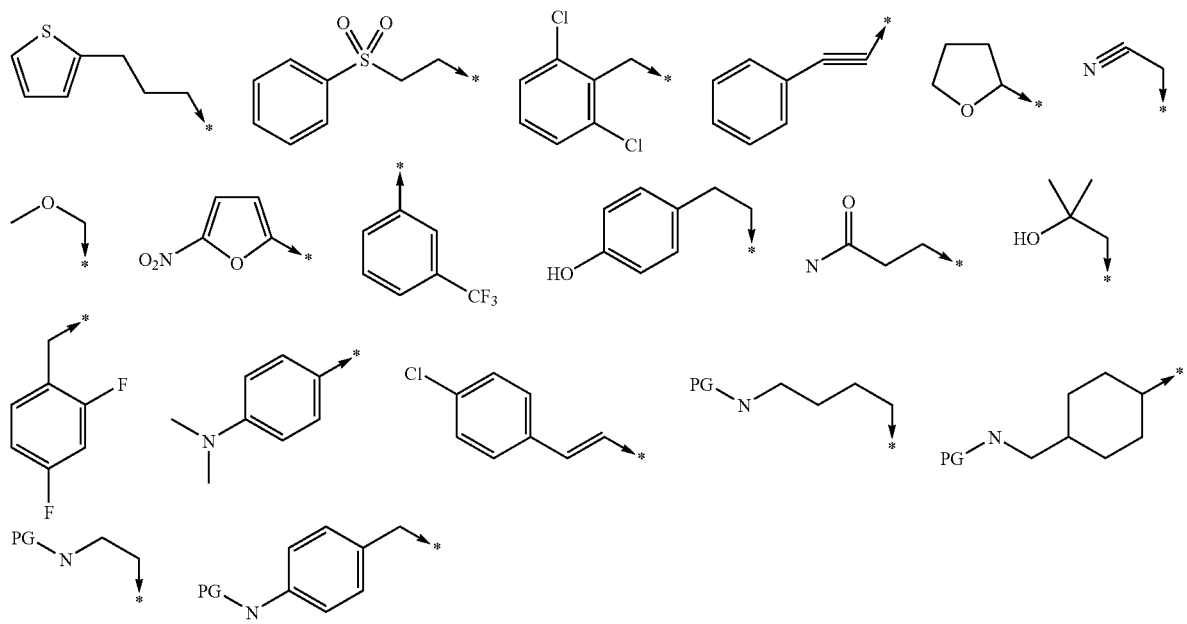

where the protective group (PG) represents H or tert-butyloxycarbonyl.

A3) Syntheses of 4-aminodisubstituted piperidines

The synthesis of 4-aminodisubstituted piperidines according to the invention, can be carried out by acid treatment of the N-Boc compounds described previously, following the following reaction diagram:

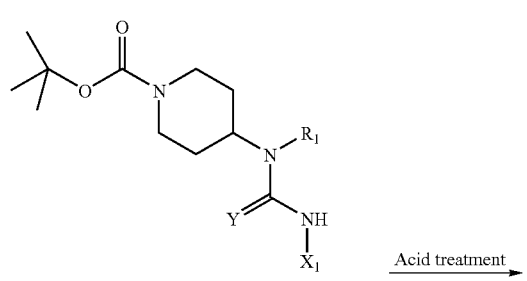

Acid treatment

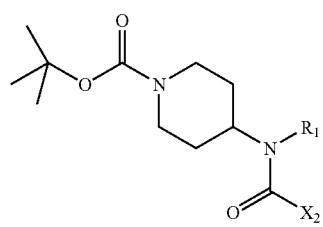

-continued

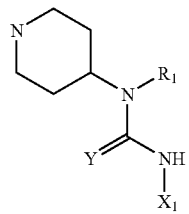

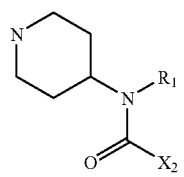

General procedure: two methods were used to carry out the deprotection in acid media of the ureas, thioureas and amides described previously. The first consists in dissolving the compound in dichloromethane and adding trifluoroacetic acid (5 to 20 eq.) whilst in the second a solution of dilute hydrochloric acid in solvents such as ethyl acetate, dioxane or diethylether (5 to 20 eq.) is used. The reaction medium is agitated for 1 to 4 hours at ambient temperature. In certain cases, dichloromethane is added and the organic phase is washed with a saturated solution of sodium bicarbonate, dried over magnesium sulphate, filtered and concentrated under vacuum in order to isolate the free base.

EXAMPLE A3

N-(3,3-diphenylpropyl)-N-(4-piperidinyl)-N'-[3-(trifluoromethyl)phenyl]urea ($C_{28}H_{30}F_3N_3O$, M=481.57)

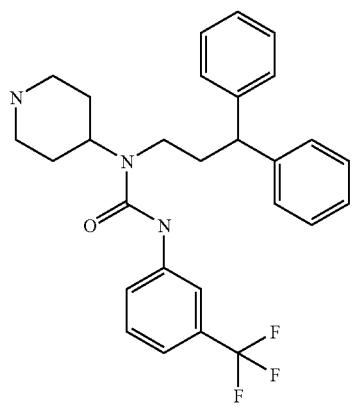

1.6 ml (21 mmol, 20 eq.) of trifluoroacetic acid is added to a solution of tert-butyl 4-((3,3-diphenylpropyl){[3-(trifluoromethyl)anilino]carbonyl}amino)-1-piperidine carboxylate (600 mg, 1.04 mmol) in dichloromethane. The reaction medium is agitated for 90 minutes then concentrated. Dichloromethane is added and the organic phase is washed with a saturated solution of sodium bicarbonate, dried over magnesium sulphate, filtered and concentrated under vacuum in order to isolate 490 mg (yield=98%) of a white foam.

NMR $^1H(CD_3OD, 400\ MHz)$ δ: 7.7 (s, 1H); 7.55 (d, 1H); 7.44 (t. H); 7.28 (m, 9H); 7.18 (m, 2H); 4.05 (m, 2H); 3.26 (m, 2H); 3.11 (d, J=10.8 Hz, 2H); 2.7 (td, J=2.4 and 12.4 Hz, 2H); 2.38 (q, J=8 Hz, 2H); 1.76 (d, J=10 Hz, 2H); 1.63 (qd, J=4 and 12.4 Hz, 2H). MS/LC: m/z=482.2 (M+H).

A series of 4-aminopiperidines was synthesized according to this procedure. The $R_1$, $X_1$ and $X_2$ radicals which can be envisaged are those already illustrated in points A1 and A2 above.

B) Synthesis in Solid Phase of 4-Aminopiperidines 4-aminopiperidines were prepared by synthesis in solid phase starting with Wang resin.

B1) Preparation of the Resin

B1a) Preparation of the P-Nitrophenyl Carbonate Wane Resin

It is carried out according to the following diagram

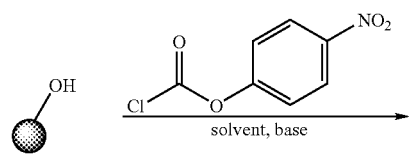

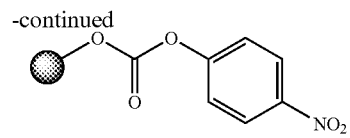

This resin was prepared from Wang resin (supplied by Bachem or Novabiochem) with a load rate greater than 0.89 mmol/g, following the procedure described in the literature (Bunin, B. A. *The Combinatorial Index*, Academic Press, 1998, p. 62-63; Dressman, B. A.; Spangle, L. A.; Kaldor, S. W. *Tetrahedron Lett.* 1996, 37, 937-940 Hauske, J. R.; Dorff, P. *Tetrahedron Lett.* 1995, 36, 1589-1592; Cao, J.; Cuny, G. D.; Hauske, J. R. *Molecular Diversity* 1998, 3, 173-179): N-methylmorpholine or pyridine and 4-nitrophenyl chloroformate are added successively to the Wang resin preswollen in dichloromethane or tetrahydrofuran at ambient temperature. The mixture is agitated overnight. The resin is washed with tetrahydrofuran, with diethylether and with dichloromethane then dried in vacuo at 50° C. overnight.

B1b) Preparation of the Piperidone Carbamate Resin

It is carried out according to the following diagram

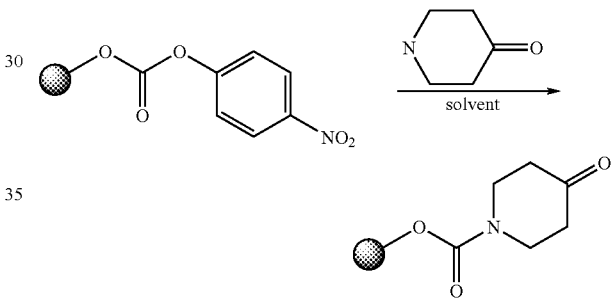

Triethylamine (1 eq.) and the molecular sieve are added to the hydrated piperidone hydrochloride diluted in dimethylformamide. The mixture is heated until complete dissolution of the ketone. This solution is added to the p-nitrophenyl carbonate Wang resin (0.05 eq.) preswollen in dimethylformamide. After agitation for 24 to 72 hours at ambient temperature, the resin is filtered then washed several times with dimethylformamide, tetrahydrofuran, diethylether and dichloromethane.

Preparation 2

2.5 g of p-nitrophenyl carbonate Wang resin (load rate of 0.88 mmol/g, 2.2 mmol) is preswollen in 100 ml of dimethylformamide. At the same time, 6.7 g (44 mmol, 20 eq.) of hydrated piperidone hydrochloride, 4.45 g (44 mmol, 20 eq.) of triethylamine and three spatulas of molecular sieve are heated in 100 ml of dimethylformamide until complete dissolution. The yellowish solution is poured warm onto the resin and the mixture is agitated for 40 hours at ambient temperature. The resin is filtered then washed with dimethylformamide, tetrahydrofuran, diethylether and dichloromethane (3 times with each solvent) then dried under vacuum. 2.4 g of pale yellow resin is isolated with a load rate of 0.88 mmol/g calculated after elementary analysis of the nitrogen.

B2) Reducing Amination on Solid Support

It is carried out according to the diagram

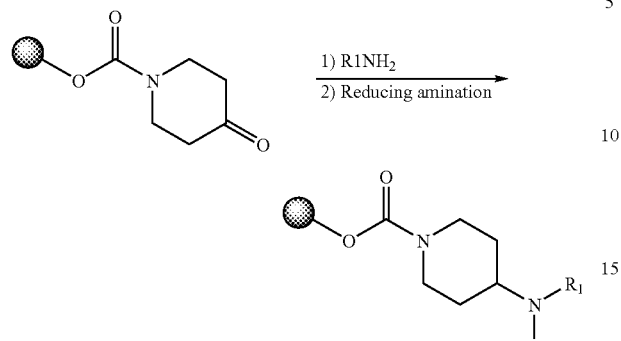

The general procedure is the following: the primary amine (5 to 10 eq.) is added to the ketonic resin preswollen in trimethylorthoformate (TMOF) then the mixture is sonicated. Then, the borane pyridine complex (8M, 5 to 10 eq.) is added and the mixture is agitated for 12 to 72 hours. The resin is filtered, washed with solvents such as dichloromethane, dimethylformamide and tetrahydrofuran then dried under vacuum (Pelter, A.; Rosser, R. M. *J. Chem. Soc. Perkin Trans I* 1984, 717-720; Bomann, M. D.; Guch, I. C.; DiMare, M. *J. Org. Chem.* 1995, 60, 5995-5996; Khan, N. M.; Arumugam, V.; Balasubramanian, S. *Tetrahedron Lett.* 1996, 37, 4819-4822).

Preparation 3

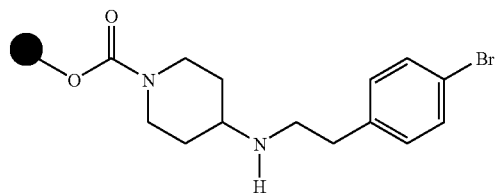

300 mg (load rate of 0.88 mmol/g, 0.27 mmol) of ketonic resin is preswollen in TMOF. Then 4-bromophenethylamine (540 mg, 420 µl, 2.7 mmol, 10 eq.) then the borane pyridine complex (8 M, 338 µl, 2.7 mmol, 10 eq.) are added. The mixture is agitated for 56 hours at ambient temperature. The resin is filtered, rinsed successively with dichloromethane, dimethylformamide, tetrahydrofuran and dichloromethane then dried under vacuum. 340 mg of pale yellow resin is thus obtained with load rate of 0.81 mmol/g calculated after elementary analysis of the nitrogen.

B3) Functionalization

B3a) Functionalization with Isocyanates or Isothiocyanates

It is carried out according to the diagram

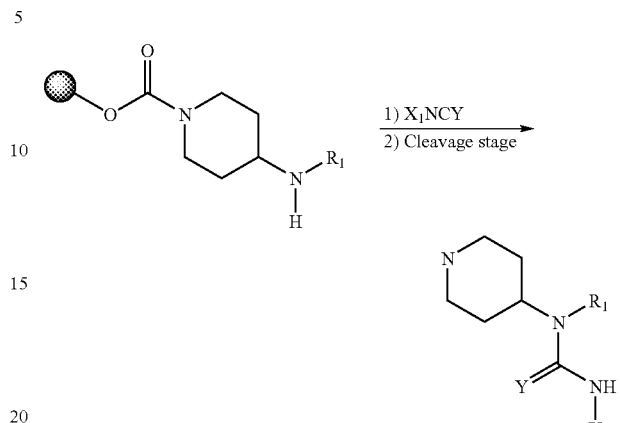

The general procedure is the following: the "secondary amine" resin is preswollen in a solvent such as dichloromethane or dimethylformamide before the addition of isocyanate or isothiocyanate (3 to 10 eq.). The mixture is agitated for 1 to 24 hours at ambient temperature. The resin is then filtered, washed with solvents such as dichloromethane, dimethylformamide and tetrahydrofuran then dried under vacuum. Cleavage of the resin is carried out in the presence of an equimolar mixture of dichloromethane and trifluoroacetic acid and agitation is carried out for 30 minutes to 4 hours. The resin is rinsed with dichloromethane then the filtrate is concentrated under vacuum. In certain cases the filtrate is redissolved in dichloromethane then desalified with a saturated solution of sodium carbonate. The organic phase is evaporated under vacuum in order to produce the free base.

EXAMPLE B3a

N-(4-bromophenethyl)-N-(4-piperidinyl)-N'-[4-(trifluoromethyl)phenyl]urea ($C_{21}H_{23}BrF_3N_3O$, M=470.3)

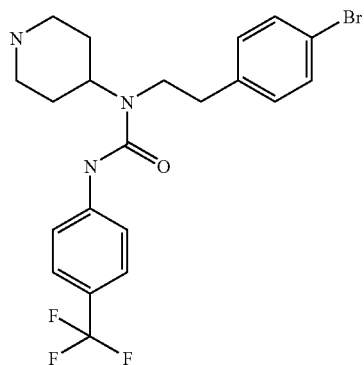

55 mg (50 µmol) of resin (see Preparation 3) is preswollen in anhydrous dichloromethane. Then 4-trifluorophenylisocyanate (28 mg, 150 µmol, 3 eq.) is added and the whole is agitated overnight. The resin is filtered, rinsed with tetrahydrofuran, with dimethylformamide, with tetrahydrofuran then with dichloromethane before being dried under vacuum.

Then agitation is carried out for 1.5 hour in the presence of 800 μl of an equimolar mixture of dichloromethane and trifluoroacetic acid. The resin is filtered and rinsed with dichloromethane, the filtrate is concentrated, rediluted in dichloromethane and washed with a saturated solution of sodium bicarbonate. 6 mg of a brown oil (yield=25%) is thus isolated.

NMR $^1$H(CD$_3$OD, 400 MHz) δ: 7.53 (m, 4H); 7.44 (d, J=6.8 Hz, 2H); 7.21 (d, J=8.4 Hz, 2H); 4.1 (m, 1H); 3.53 (t, J=7.2 Hz, 2H); 3.12 (d, J=12.8 Hz, 2H); 2.89 (t, J=8 Hz, 2H); 2.7 (m, 2H); 1.73 (m, 4H). MS/LC: m/z=472.2 (M+H).

A series of ureas (Y=O) and thioureas (Y=S) was synthesized according to this procedure. The R$_1$ radicals which can be envisaged are the following:

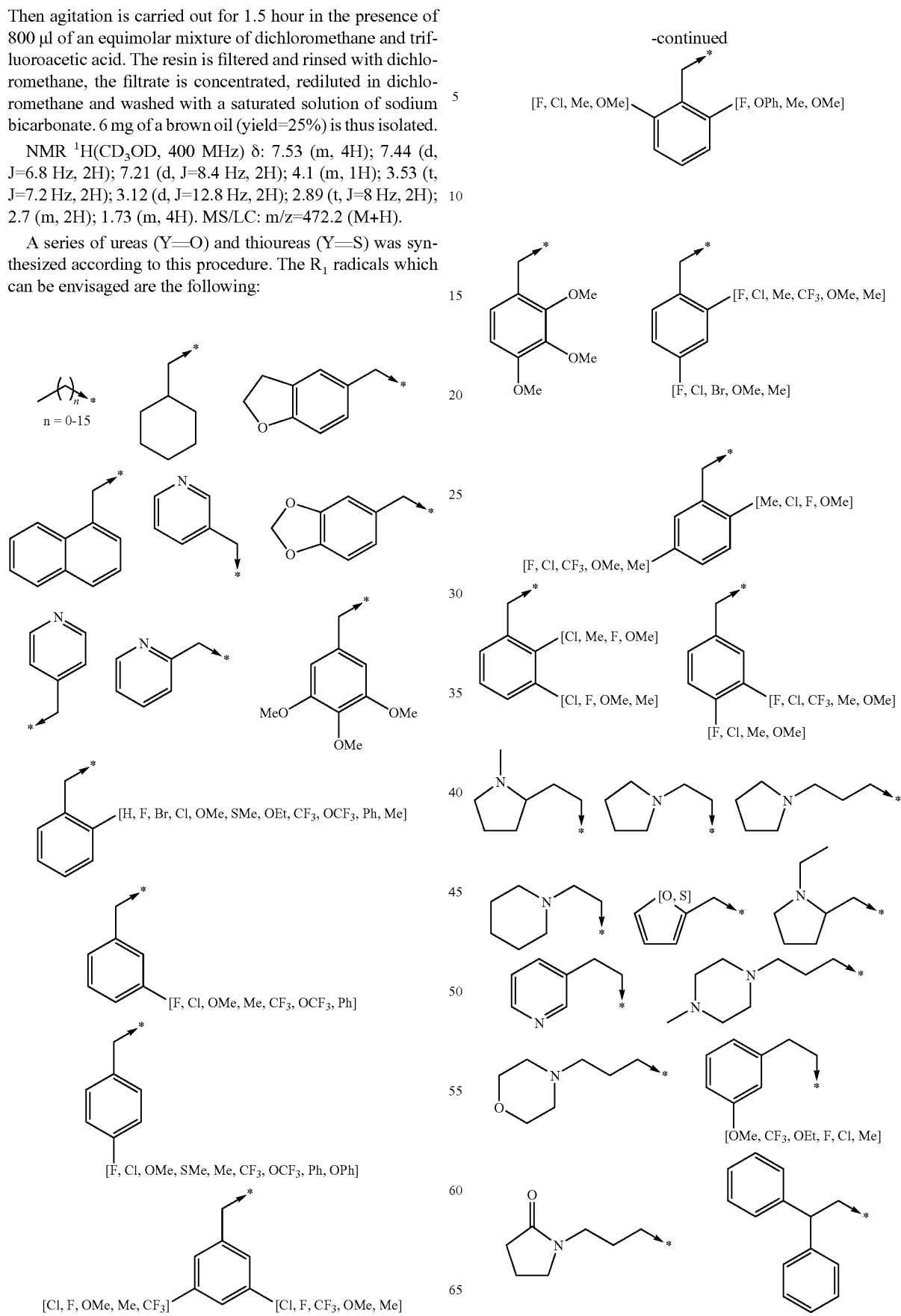

-continued

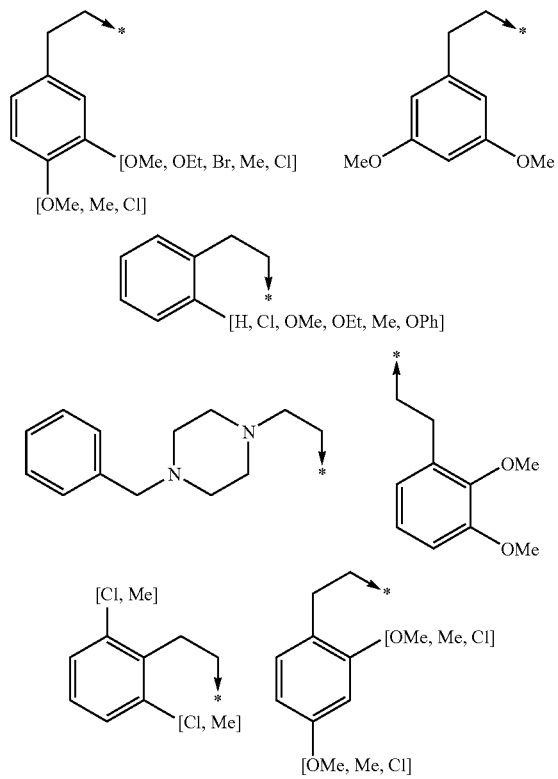

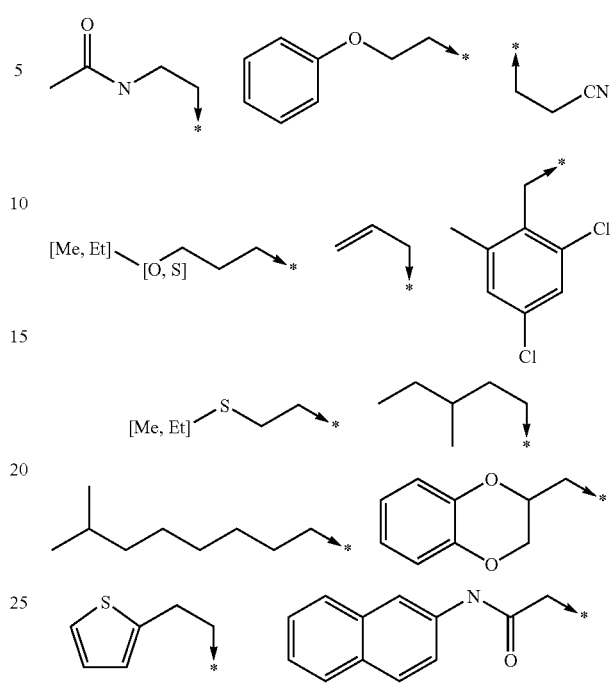

The X₁ radicals which can be envisaged are those illustrated in point A above.

B3b) Functionalization with Sulphonyl Chlorides

It is carried out according to the following diagram

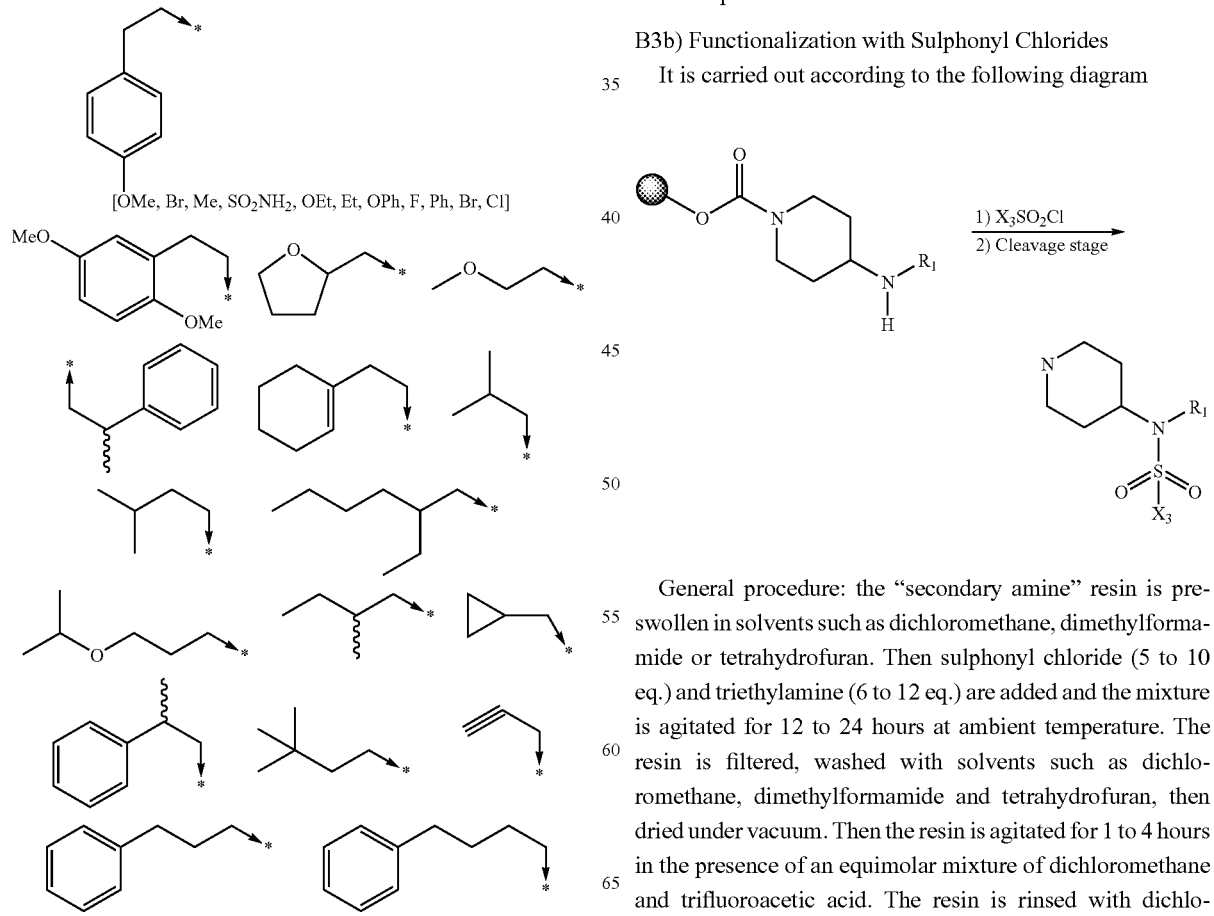

General procedure: the "secondary amine" resin is pre-swollen in solvents such as dichloromethane, dimethylformamide or tetrahydrofuran. Then sulphonyl chloride (5 to 10 eq.) and triethylamine (6 to 12 eq.) are added and the mixture is agitated for 12 to 24 hours at ambient temperature. The resin is filtered, washed with solvents such as dichloromethane, dimethylformamide and tetrahydrofuran, then dried under vacuum. Then the resin is agitated for 1 to 4 hours in the presence of an equimolar mixture of dichloromethane and trifluoroacetic acid. The resin is rinsed with dichloromethane then the filtrate is concentrated under vacuum. In certain cases the filtrate is redissolved in dichloromethane then desalified with a saturated solution of sodium carbonate. The organic phase is evaporated under vacuum in order to produce the free base.

EXAMPLE B3b

N-(4-bromophenethyl)-4-methoxy-N-(4-piperidinyl) phenyl sulphonamide ($C_{20}H_{25}BrN_2O_3S$, M=453.4)

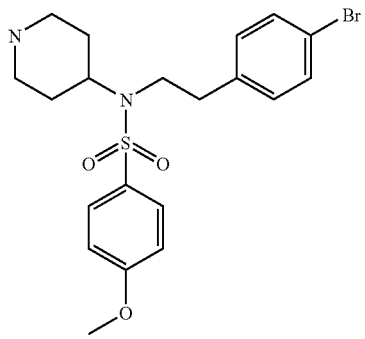

55 mg (50 µmol) of resin (see Preparation 3) is preswollen in anhydrous dichloromethane. Then triethylamine (42 µl, 300 µmol, 6 eq.) then 4-methoxybenzene sulphonyl chloride (51.5 mg, 250 µmol, 5 eq.) are added and the whole is agitated overnight. The resin is filtered, rinsed with tetrahydrofuran, with dimethylformamide, with tetrahydrofuran then with dichloromethane before being dried under vacuum. The reaction is repeated a second time in order to have a complete substitution. 800 µl of an equimolar mixture of dichloromethane and trifluoroacetic acid is added and agitation is carried out for 1.5 hour at ambient temperature. The resin is filtered and rinsed with dichloromethane. The filtrate is concentrated, rediluted in dichloromethane and washed with a saturated solution of sodium bicarbonate. 14 mg of a brown oil (yield=63%) were thus isolated.

NMR $^1$H(CD$_3$OD, 400 MHz) δ: 7.8 (dd, J=2.8 and 10 Hz, 2H); 7.44 (dd, J=1.2 and 6.8 Hz, 2H); 7.17 (d, J=8.4 Hz, 2H); 7.07 (dd, J=3.2 and 10 Hz, 2H); 3.87 (s, 3H, OCH$_3$); 3.72 (m, 1H); 3.3 (m, 2H); 3.04 (d, J=12.8 Hz, 2H); 2.92 (t, J=8.4 Hz, 2H); 2.6 (t, J=12.4 Hz, 2H); 1.58 (m, 2H); 1.47 (broad d, J=10 Hz, 2H). MS/LC: m/z=455 (M+H).

A series of sulphonamides was synthesized according to this procedure. The R$_1$ radicals which can be envisaged are those illustrated in points A and B3a above. The X$_3$ radicals which can be envisaged are the following:

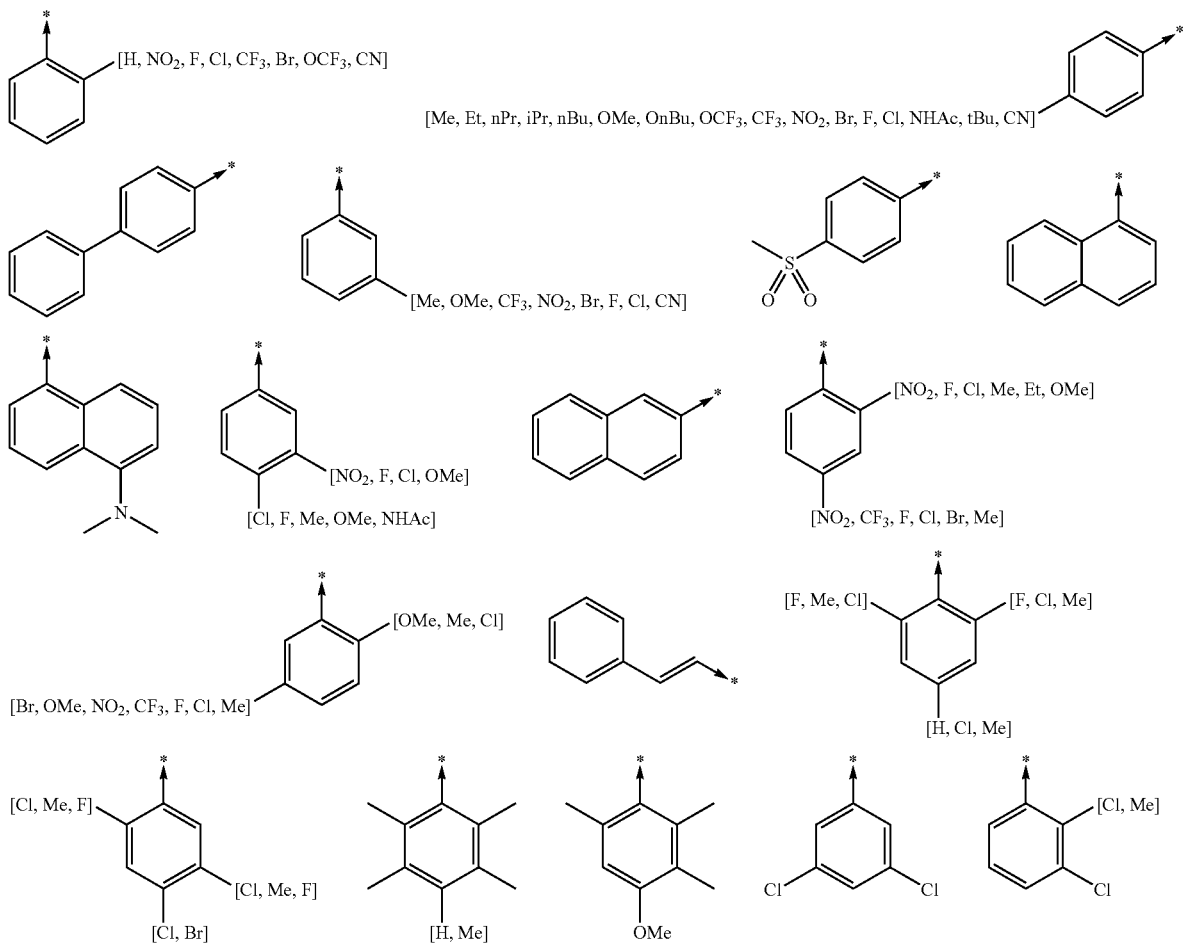

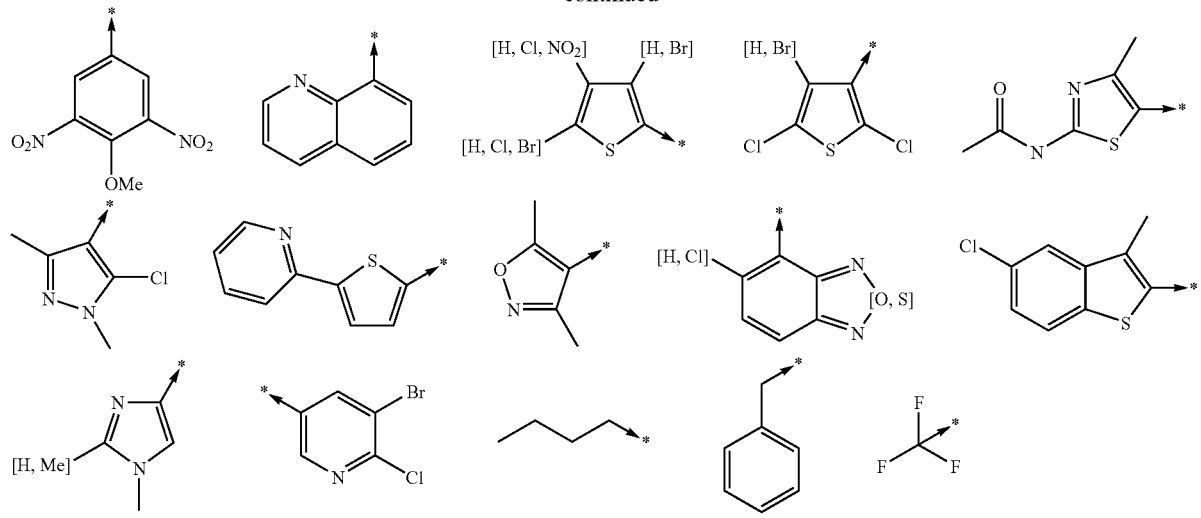

B3c) Functionalization with Acid Chlorides

It is carried out according to the following diagram.

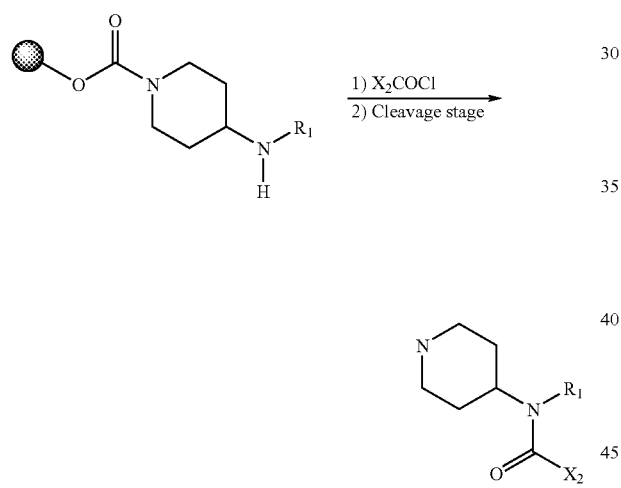

General procedure: the "secondary amine" resin is preswollen in solvents such as dichloromethane, dimethylformamide or tetrahydrofuran. Then the acid chloride (5 to 10 eq.) and triethylamine (6 to 12 eq.) are added and the mixture is agitated for 12 to 24 hours at ambient temperature. The resin is filtered, washed with solvents such as dichloromethane, dimethylformamide and tetrahydrofuran, then dried under vacuum. The resin is then agitated for 1 to 4 hours in the presence of an equimolar mixture of dichloromethane and trifluoroacetic acid. The resin is rinsed with dichloromethane then the filtrate is concentrated under vacuum. In certain cases the filtrate is redissolved in dichloromethane then desalified with a saturated solution of sodium carbonate. The organic phase is evaporated under vacuum in order to produce the free base.

EXAMPLE B3c

N-(4-bromophenethyl)-N-(4-piperidinyl)-2-thiophene carboxamide ($C_{18}H_{21}BrN_2OS$, M=393.3)

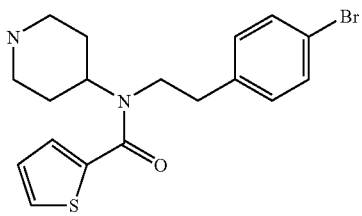

55 mg (50 µmol of resin (see Preparation 3) is preswollen in anhydrous tetrahydrofuran Then triethylamine (42 µl, 300 µmol, 6 eq.) then 2-thiophene carbonyl chloride (37 mg, 250 mmol, 5 eq.) are added and the whole is agitated overnight. The resin is filtered, rinsed with tetrahydrofuran, with dimethylformamide, with tetrahydrofuran then with dichloromethane before being dried under vacuum. 800 µl of an equimolar mixture of dichloromethane and trifluoroacetic acid is added and agitation is carried out for 1.5 hour at ambient temperature. The resin is filtered and rinsed with dichloromethane. The filtrate is concentrated, rediluted in dichloromethane and washed with a saturated solution of sodium bicarbonate in order to obtain 10 mg of a brown oil (yield=50%).

NMR $^1$H(CD$_3$OD, 400 MHz) δ: 7.64 (dd, J=0.8 and 4.8 Hz, 1H); 7.44 (d, J=8.4 Hz, 2H); 7.36 (d, J=3.6 Hz, 1H); 7.14 (m, 3H); 4.11 (m, 1H); 3.61 (t, J=8 Hz, 2H); 3.09 (d, J=12 Hz, 2H); 2.92 (m, 2H); 2.54 (m, 2H); 1.82 (m, 2H); 1.7 (m, 2H). MS/LC: m/z=393.1 (M+H).

A series of amides was synthesized according to this procedure. The $R_1$ groups envisaged are those illustrated in points A and B3 above. The $X_2$ groups are illustrated below.

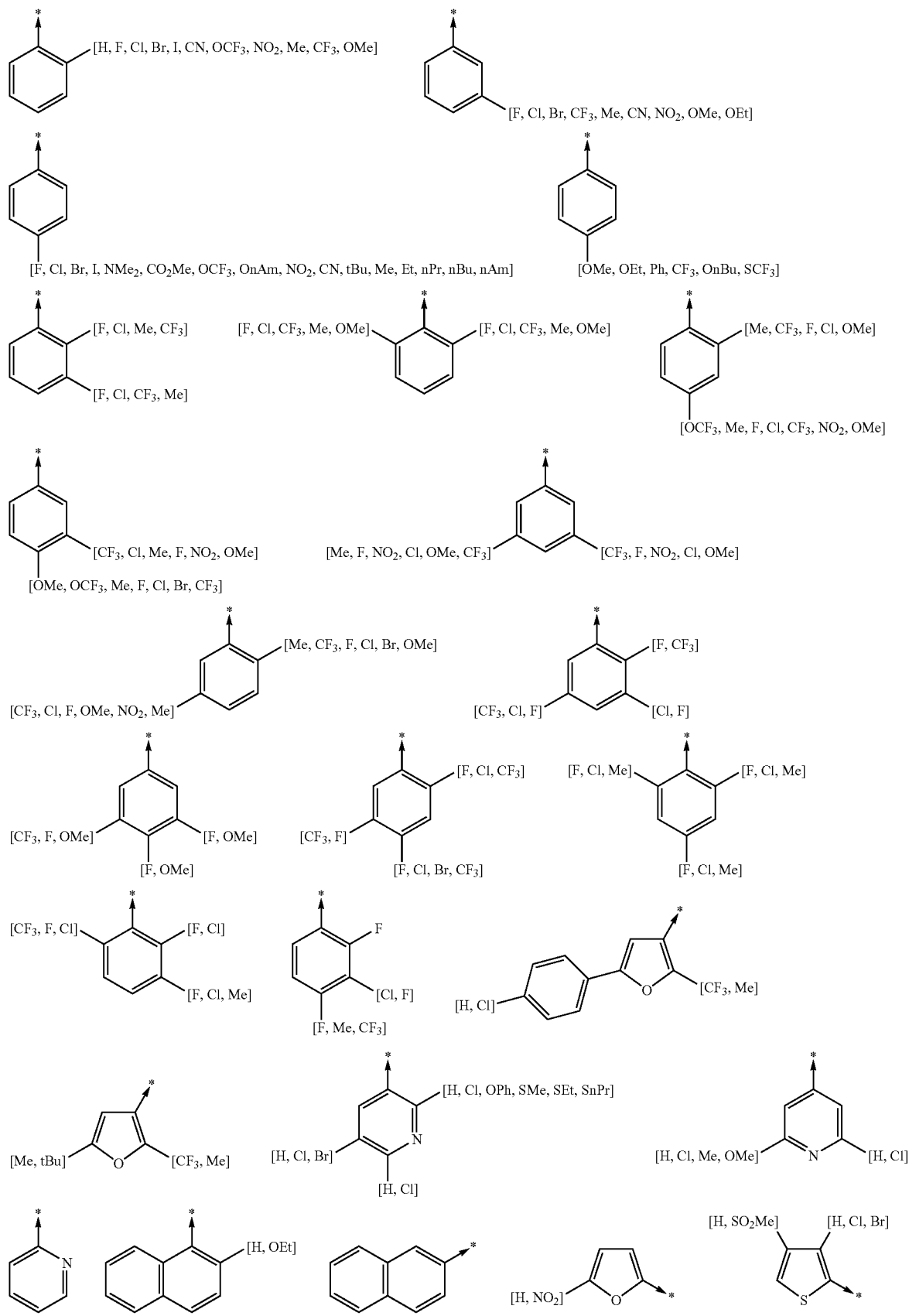

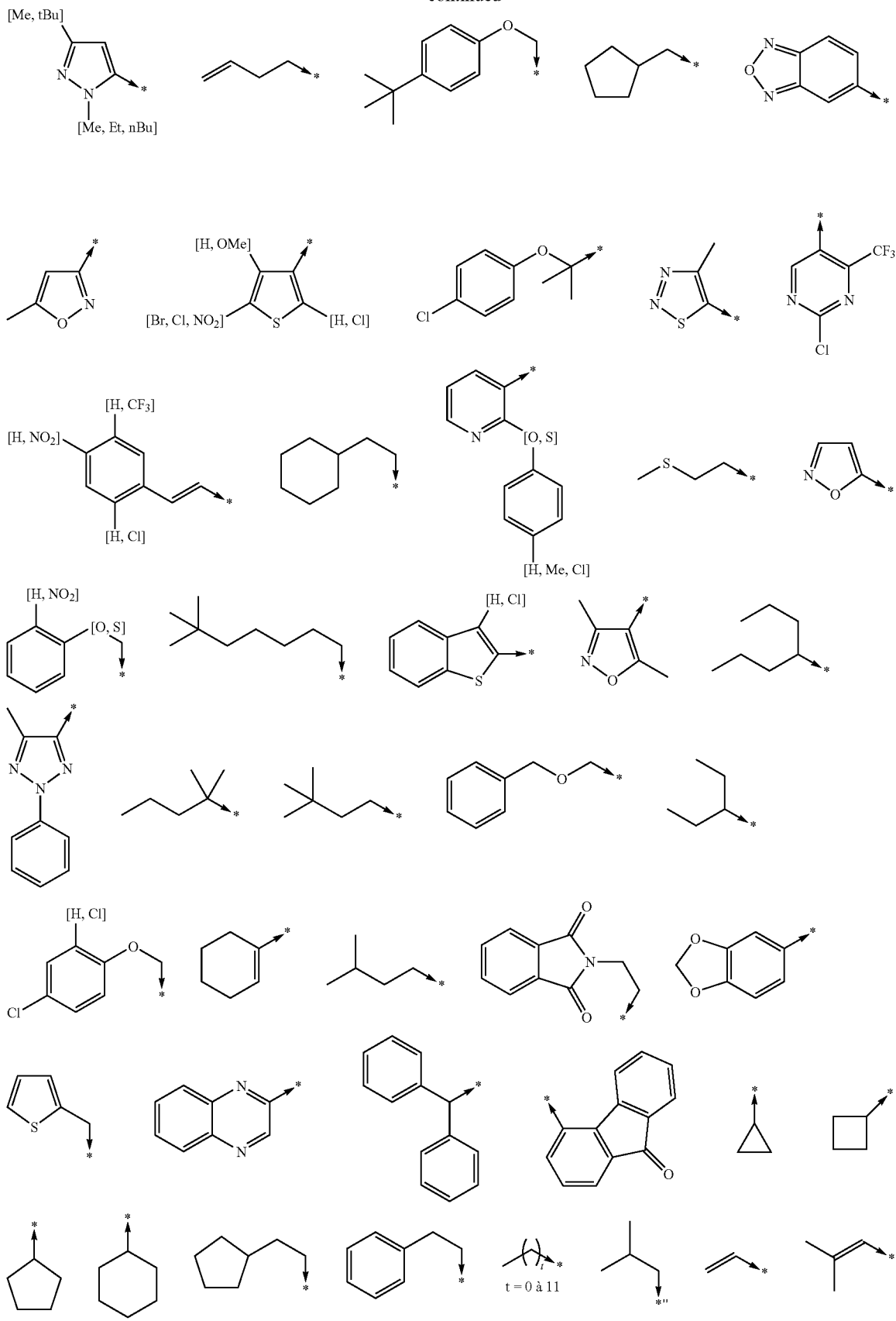

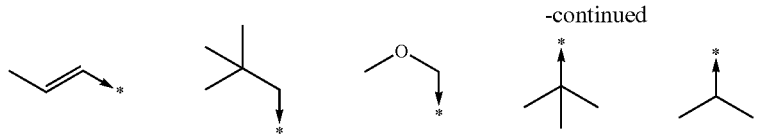

B3d) Functionalization with Carboxylic Acids

It is carried out according to the procedure described in the literature (Kobayashi, S Aoki, Y., *J. Comb. Chem.* 1999, 1, 371-372) following the diagram.

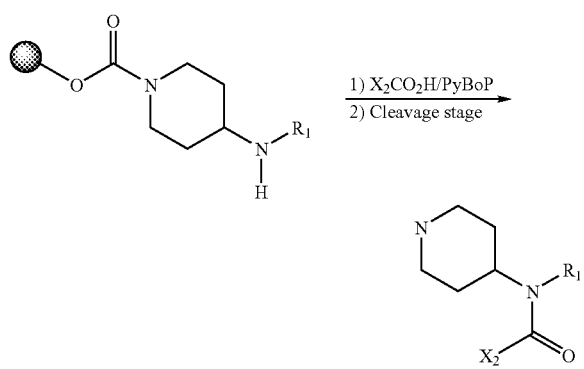

General procedure: the "secondary amine" resin is preswollen in solvents such as dichloromethane, dimethylformamide or tetrahydrofuran. Then the carboxylic acid (3 to 5 eq.), benzo-triazol-1-yl-oxy-tris-pyrrolidino phosphonium hexafluorophosphate (PyBoP, 3 to 5 eq.) and diisopropylethylamine (6 to 10 eq.) are added and the mixture is agitated for 24 hours at ambient temperature. The resin is filtered, washed with solvents such as dichloromethane, dimethylformamide and tetrahydrofuran, then dried under vacuum. Then the resin is agitated for 1 to 4 hours in the presence of an equimolar mixture of dichloromethane and trifluoroacetic acid. The resin is rinsed with dichloromethane then the filtrate is concentrated under vacuum. In certain cases the filtrate is redissolved in dichloromethane then desalified with a saturated solution of sodium carbonate. The organic phase is evaporated under vacuum in order to produce the free base.

EXAMPLE B3d

N-[2-(4-bromophenyl)ethyl]-N-(4-piperidinyl)acetamide ($C_{15}H_{21}BrN_2O$, M=325.25)

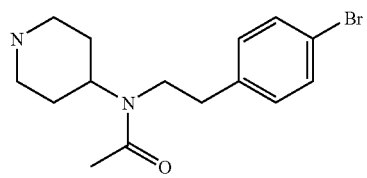

55 mg (50 µmol) of resin (see Preparation 3) is preswollen in anhydrous dimethylformamide. Then acetic acid (8.8 mg, 150 µmol, 3 eq.) PyBoP (76 mg, 150 µmol, 3 eq.) then diisopropylethylamine (38 mg, 300 µmol, 6 eq.) are added and the whole is agitated overnight. The resin is filtered, rinsed with dimethylformamide, with tetrahydrofuran then with dichloromethane before being dried under vacuum. 800 µl of an equimolar mixture of dichloromethane and trifluoroacetic acid is added and agitation is carried out for 1.5 hour at ambient temperature. The resin is filtered and rinsed with dichloromethane. The filtrate is concentrated, rediluted in dichloromethane and washed with a saturated solution of sodium bicarbonate in order to obtain 11 mg of a brown oil (yield=68%).

NMR $^1$H(CD$_3$OD, 400 MHz) δ: 7.44 (m, 2H); 7.20 (m, 2H); 4.05 (m, 1H); 3.45 (m, 2H); 3.10 (m, 2H); 2.83 (m, 2H); 2.64 (m, 2H); 2.13 (s, 3H); 1.73 (m, 4H). MS/LC: m/z=325.2 (M+H).

A series of amides was synthesized according to this procedure. The $R_1$ groups envisaged are those illustrated in points A and B3a above. The $X_2$ groups are illustrated in point A above.

C) Functionalization of the Piperidine Part in Solution

C1) Obtaining Piperidine with $R_3$=—C(Y)NHX$_1$

It is carried out according to the diagram

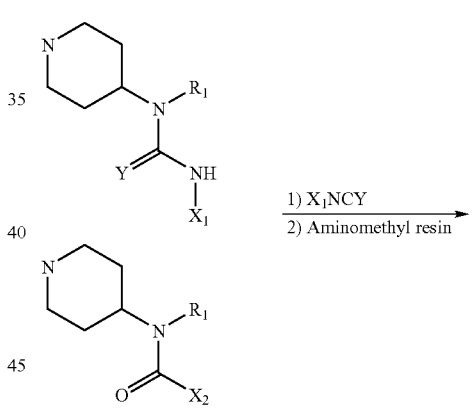

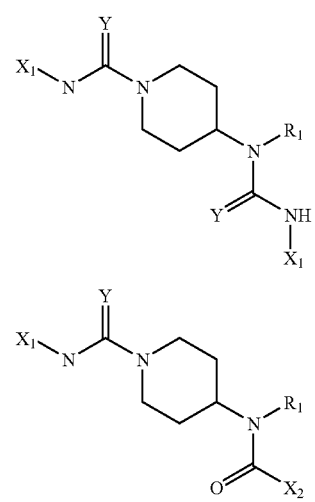

General procedure: an isocyanate or isothiocyanate (1.1 to 1.5 eq.) is added to piperidine in the form of the free base diluted in dichloromethane. The mixture is agitated for one to 18 hours at ambient temperature. The aminomethyl resin (0.2 to 1 eq.) is added and the mixture is again agitated for 2 to 18 hours. In certain cases, ion exchange resin such as IRA68 or SAX is added. The resins are filtered and the filtrate is concentrated. In certain cases, the product is dissolved in dichloromethane or ethyl acetate then filtered on a silica gel or basic alumina cartridge (500 mg, Interchim).

EXAMPLE C1

4-((3,3-diphenylpropyl){[3-(trifluoromethyl)anilino]carbonyl}amino)-N-phenyl-1-piperidine carboxamide ($C_{35}H_{35}F_3N_4O_2$, M=600.68)

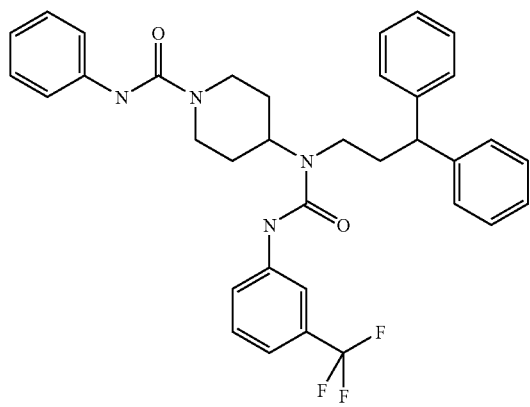

N-(3,3-diphenylpropyl)-N-(4-piperidinyl)-N'-[3-(trifluoromethyl)phenyl]urea (24 mg, 0.05 mmol) is dissolved in dichloromethane. Phenylisocyanate (9 mg, 0.075 mmol, 1.5 eq.) is added and the mixture is agitated for 2.5 hours. The aminomethyl resin (0.02 mmol) is added and the reaction is again agitated overnight. The resin is filtered, rinsed with dichloromethane and the filtrate is concentrated. The oil obtained is passed through a silica gel cartridge eluting with an equimolar mixture of heptane and ethyl acetate in order to obtain 12 mg (yield=40%) of a yellow oil after concentration.

NMR $^1$H(CD$_3$OD, 400 MHz) δ: 7.72 (s, 1H); 7.58 (d, 1H); 7.44 (m, 1H); 7.38 (m, 2H); 7.29 (m, 12H); 7.12 (m, 2H); 7.07 (m, 1H); 4.2 (d, J=12.4 Hz, 3H); 3.21 (t, J=8 Hz, 2H); 2.9 (t, J=12.4 Hz, 2H); 2.38 (q, J=8 Hz, 2H); 1.73 (d, J=10 Hz, 2H); 1.54 (qd, J=3.6 and 12 Hz, 2H). MS/LC: m/z=601.4 (M+H).

A series of ureas (Y=O) and thioureas (Y=S) was synthesized according to this procedure. The $R_1$, $X_1$ and $X_2$ groups which can be envisaged, are those illustrated in the above points (A and B3a), A, and (A and B3c) respectively.

C2) Functionalization with Carboxylic Acids

It is carried out according to the following diagram

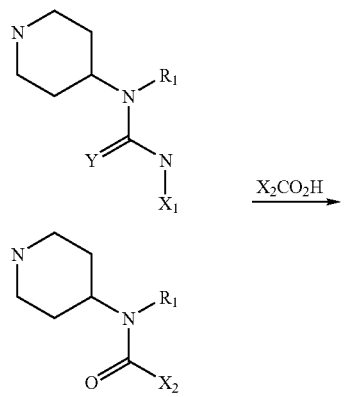

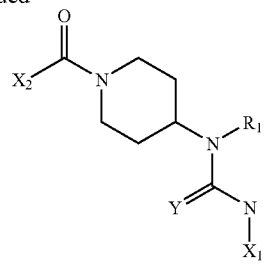

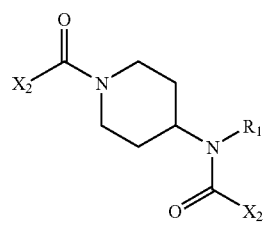

General procedure: the P-EDC resin (1.3 to 3 eq.) is pre-swollen in anhydrous dichloromethane. Carboxylic acid (1.1 to 2.5 eq.) is dissolved in an anhydrous solvent such as dichloromethane, dimethylformamide or tetrahydrofuran and is added to the resin. This mixture is agitated for 5 to 30 minutes at ambient temperature. The 4-aminodisubstituted piperidine, in the form of the free base, in solution in an anhydrous solvent such as dichloromethane, dimethylformamide or tetrahydrofuran is then added to this mixture and the whole is agitated for 1 to 18 hours at ambient temperature. In certain cases, ion exchange resin such as IRA68 or SAX is added and the mixture is again agitated at ambient temperature for 1 to 18 hours. The resins are filtered on frit, on a SAX ion exchange resin cartridge (500 mg, Interchim) or on a basic alumina cartridge (500 mg, Interchim).

EXAMPLE C2

N-(1-acetyl-4-piperidinyl)-N-(3,3-diphenylpropyl)-N'-[3-(trifluoromethyl)phenyl]urea ($C_{30}H_{32}F_3N_3O_2$, M=523.60)

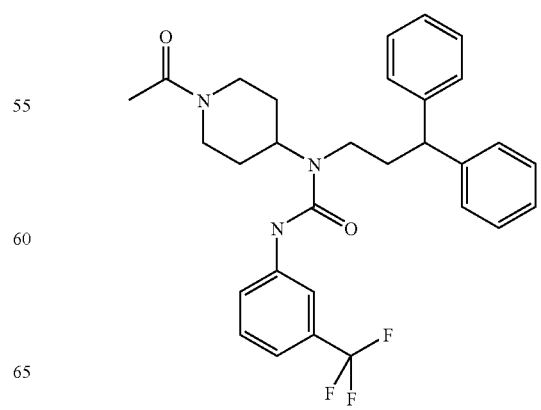

117 mg (175 µmol, 3.5 eq.) of P-EDC resin is preswollen in 1.5 ml of anhydrous dichloromethane. Acetic acid (7.5 mg, 125 µmol, 2.5 eq.) is added and the mixture is agitated for 10 minutes. Then N-(3,3-diphenylpropyl)-N-(4-piperidinyl)-N'-[3-(trifluoromethyl)phenyl]urea (24.3 mg, 50 µmol) is added in its turn and the mixture is agitated overnight. The resin is filtered and the filtrate is concentrated. The oil obtained is passed through a silica gel cartridge eluting with an equimolar mixture of heptane and ethyl acetate in order to obtain 16 mg (yield=62%) of a white foam after concentration.

NMR $^1$H(CD$_3$OD, 400 MHz) δ: 7.71 (s, 1H); 7.58 (d, J=8.4 Hz, 1H); 7.43 (t, J=8 Hz, 1H); 7.28 (m, 9H); 7.17 (m, 2H); 4.56 (dd, J=2 and 11.2 Hz, H); 4.17 (m, 1H); 3.96 (t, J=7.6 Hz, 1H); 3.88 (d, J=12 Hz, 1H); 3.19 (q, J=4 and 8 Hz, 2H), 3.1 (t, J=12 Hz, 1H); 2.58 (t, J=12 Hz, 1H); 2.37 (m, 2H); 2.06 (s, 3H, CH$_3$); 1.72 (t, J=14.4 Hz, 2H); 1.43 (qd, J=4 and 12.4 Hz, 2H). MS/LC: m/z=524.3 (M+H).

A series of amides was synthesized according to this procedure. The R$_1$, X$_1$ and X$_2$ groups which can be envisaged, are those illustrated in points (A and B3a), A, (A and B3c) respectively.

C3) Functionalization with Sulphonyl Chlorides

It is carried out according to the following diagram

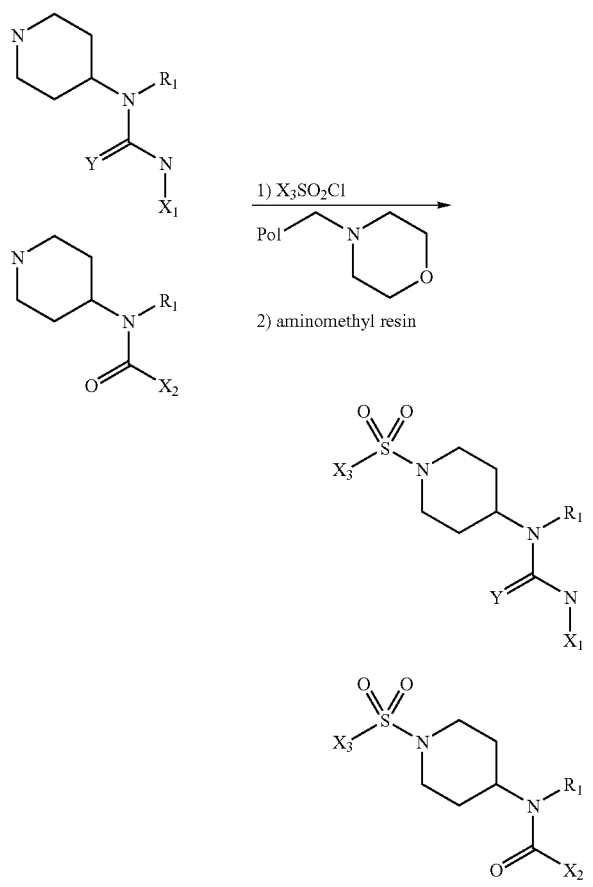

General procedure: the morpholinomethyl resin (Novabiochem, 2 to 3 eq.) is preswollen in anhydrous solvents such as dichloromethane, dimethylformamide or tetrahydrofuran. Sulphonyl chloride (1.1 to 2 eq.) dissolved in anhydrous solvents such as dichloromethane, dimethylformamide or tetrahydrofuran is added, followed by 4-aminodisubstituted piperidine. The mixture is agitated for 16 to 48 hours. The aminomethyl resin (0.1 to 1.5 eq.) is added and the reaction medium is agitated overnight. In certain cases, ion exchange resin such as IRA68 or SAX is added and the mixture is agitated at ambient temperature for 1 to 18 hours. The resins are filtered on frit, on a SAX ion exchange resin cartridge (500 mg, Interchim) or on a basic alumina cartridge (500 mg, Interchim).

EXAMPLE C3

N-(3,3-diphenylpropyl)-N-{1-[(4-methoxyphenyl)sulphonyl]-4-piperidinyl}-N'-[3-(trifluoromethyl)phenyl]urea (C$_{35}$H$_{36}$F$_3$N$_3$N$_3$O$_4$S, M=651.75)

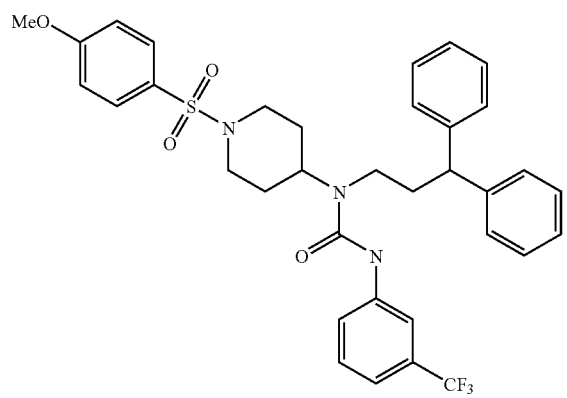

27.5 mg (100 µmol, 2 eq.) of morpholinomethyl resin is preswollen in anhydrous tetrahydrofuran, then 4-methoxyphenylsulphonyl chloride (15.5 mg, 0.075 mmol, 1.5 eq.) then N-(3,3-diphenylpropyl)-N-(4-piperidinyl)-N'-[3-(trifluoromethyl)phenyl]urea (24.3 mg, 0.05 mmol) are added. The mixture is agitated overnight. The aminomethyl (20 mg) and SAX ion exchange resins are added and the mixture is agitated overnight. The resins are filtered and rinsed with dichloromethane. The oil obtained after evaporation is passed through a silica gel cartridge (500 mg, Interchim) eluting with ethyl acetate in order to obtain 18 mg (yield=56%) of a white solid after concentration.

NMR $^1$H(CD$_3$OD, 400 MHz) δ: 7.71 (d, J=9.2 Hz, 2H); 7.65 (s, 1H); 7.51 (d, 1H); 7.41 (t, J=7.6 Hz, 1H); 7.29 (m, 9H); 7.20 (m, 2H); 7.11 (dd, J=1.6 and 6.8 Hz, 2H); 3.88 (s, 3H, OCH$_3$); 3.77 (d, J=12.4 Hz, 2H); 3.16 (t, J=8 Hz, 2H); 2.33 (m, 4H) 1.71 (d. J=10 Hz, 2H); 1.62 (qd, J=4 and 12 Hz, 2H); 1.3 (m, 2H). MS/LC: m/z=652.4 (M+H).

A series of sulphonamides was synthesized according to this procedure. The R$_1$, X$_1$, X$_2$ and X$_3$ group, which can be envisaged are those illustrated in points (A and B3a), A, (A and B3c) and B3b respectively.

D) Synthesis of Tri-Substituted Piperidines in Solid Phase

It is carried out starting from vinyl sulphone resin (Kroll, F. E. K.; Morphy, R.; Rees, D.: Giani. D. *Tetrahedron Lett.* 1997, 38, 8573-8576; Brown, A. R. *J. Comb. Chem.* 1999, 1, 283-285) according to the following diagram D1) Preparation of the Resin It is carried out according to the following diagram:

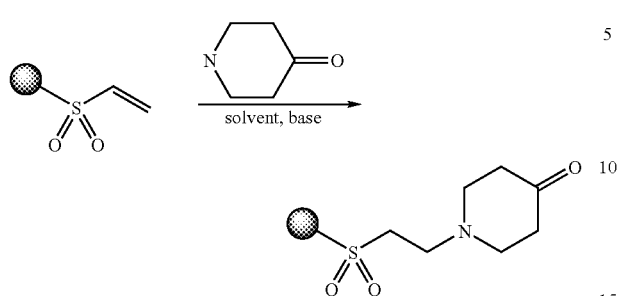

Triethylamine (1 eq.) is added to hydrated piperidone hydrochloride diluted in dimethylformamide. The mixture is heated until complete dissolution of the ketone. This solution is added to the vinyl sulphone resin (0.05 eq.) preswollen in dimethylformamide. After agitation for 24 to 72 hours at ambient temperature, the resin is filtered then washed several times with dimethylformamide, tetrahydrofuran, diethylether and dichloromethane.

Preparation 4

1.5 g of vinyl sulphone resin (Novabiochem, load rate of 1 mmol/g, 1.5 mmol) is preswollen in 50 ml of dimethylformamide. At the same time, 2.3 g (15 mmol, 10 eq.) of hydrated piperidone hydrochloride and 1.8 g (15 mmol, 10 eq.) of triethylamine are heated in 100 ml of dimethylformamide until complete dissolution. The yellowish solution is poured warm onto the resin and the mixture is agitated for 24 hours at ambient temperature. The resin is filtered then washed with dimethylformamide, tetrahydrofuran, diethylether and dichloromethane (3 times with each solvent) then dried under vacuum. 1.7 g of pale yellow resin is isolated with a load rate of 1 mmol/g calculated after elementary analysis of the nitrogen.

D2) Reducing Amination on Solid Support

It is carried out according to the procedure described in the literature (Pelter, A.; Rosser, R. M.; *J. Chem. Soc. Perkin Trans I* 1984, 717-720; Bomann, M. D.; Guch, I. C.; DiMare, M.; *J. Org. Chem.* 1995, 60, 5995-5996; Khan, N. M.; Arumugam, V.; Balasubramanian, S.; *Tetrahedron Lett.* 1996, 37, 4819-4822) following the diagram:

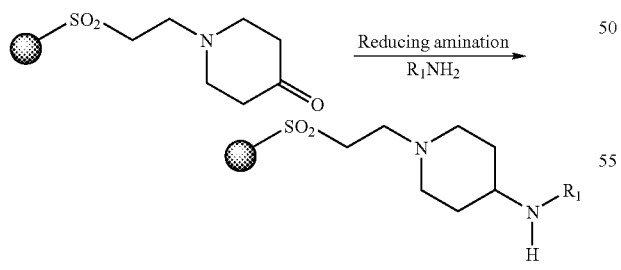

General procedure: The primary amine (5 to 10 eq.) is added to the ketonic resin preswollen in trimethylorthoformate (TMOF) then the mixture is sonicated. Then the borane pyridine complex (8 M, 5 to 10 eq.) is added and the mixture is agitated for 12 to 72 hours. The resin is filtered, washed with solvents such as dichloromethane, dimethylformamide, methanol and tetrahydrofuran then dried under vacuum.

Preparation 5

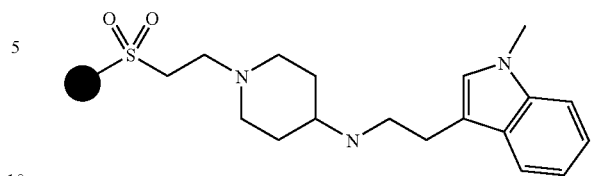

1 g (load rate of 1 mmol/g, 1 mmol) of ketonic resin is preswollen in TMOF. Then 2-(1-methyl-1H-indol-3-yl)ethylamine (1.01 g, 10 mmol, 10 eq.) then the borane pyridine complex (8M, 1.25 ml, 10 mmol, 10 eq.) are added. The mixture is agitated for 48 hours at ambient temperature. The resin is filtered, rinsed successively with dichloromethane, dimethylformamide, methanol, tetrahydrofuran and dichloromethane then dried under vacuum. 1.05 g of pale yellow resin is thus obtained with a load rate of 0.91 mmol/g calculated after elementary analysis of the nitrogen.

D3) Functionalization of the Secondary Amine

D3a) Functionalization with Isocyanates

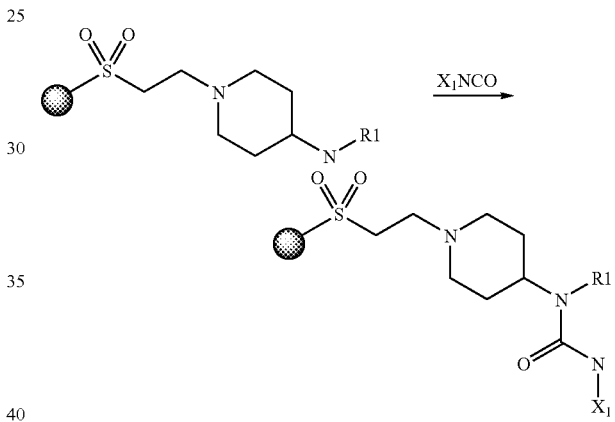

General procedure: the "secondary amine" resin is preswollen in a solvent such as dichloromethane or dimethylformamide before the addition of isocyanate (3 to 10 eq.). The mixture is agitated for 1 to 24 hours at ambient temperature. The resin is then filtered, washed with solvents such as dichloromethane, dimethylformamide and tetrahydrofuran then dried under vacuum.

Preparation 6

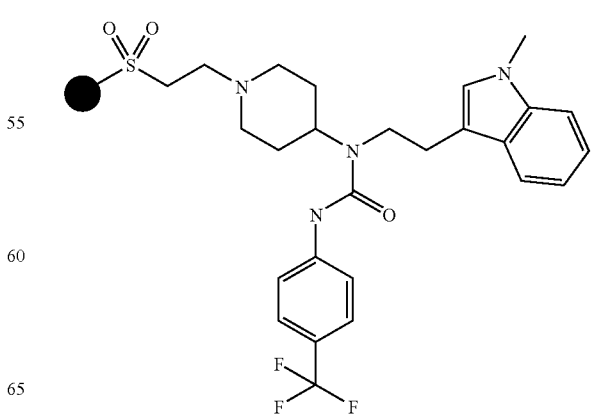

55 mg (50 μmol) of resin (see Preparation 5) is preswollen in anhydrous dichloromethane. Then 4-trifluorophenylisocyanate (28 mg, 150 μmol, 3 eq.) is added and the whole is agitated for 2 hours at ambient temperature. The resin is filtered, rinsed with tetrahydrofuran, with dimethylformamide, with tetrahydrofuran then with dichloromethane before being dried under vacuum.

D3 b) Functionalization with Sulphonyl Chlorides

The functionalization operating method is identical to that stated in point B3b.

D3c) Functionalization with Acid Chlorides

The functionalization operating method is identical to that stated in point B3c.

D3d) Functionalization with Carboxylic Acids

The functionalization operating method is identical to that stated in point B3d.

D4) Cleavage Stage

The cleavage stage described below is valid whatever the functionalization carried out beforehand on the secondary amine:

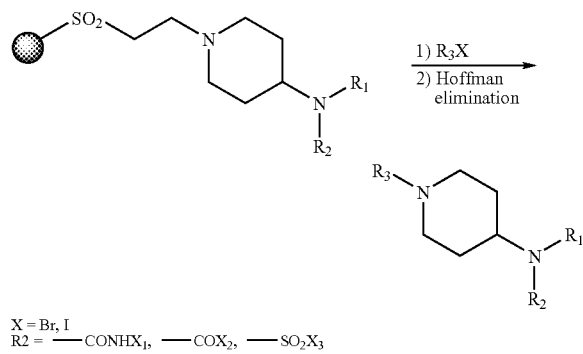

X = Br, I
R2 = —CONHX₁, —COX₂, —SO₂X₃

General procedure: The disubstituted resin is swollen in solvents such as dichloromethane, dimethylformamide or tetrahydrofuran then the halide R₃X is added in which R₃ has the meaning indicated previously and X represents a halogen atom (5 eq.) and the mixture agitated overnight at a temperature comprised between 20 and 60° C. The resin is filtered, rinsed with solvents such as dimethylformamide, tetrahydrofuran, methanol and dichloromethane then dried under vacuum. The resin is swollen again in dichloromethane and basic ion exchange resin (Ouyang, X.; Armstrong, R. W.; Murphy, M. M. *J. Org. Chem.* 1998, 63, 1027-1032) is added. The whole is agitated for 48 hours at ambient temperature. The resins are filtered, rinsed with dichloromethane and the filtrate is concentrated under vacuum.

EXAMPLE D4

N-[2-(1-methyl-1H-indol-3-yl)ethyl]-N-(1-methyl-4-piperidinyl)-N'-[4-(trifluoromethyl)phenyl]urea
($C_{25}H_{29}F_3N_4O$, M=458.5)

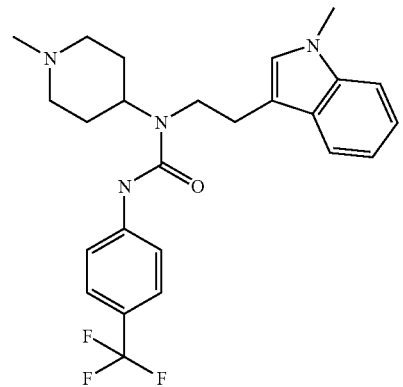

55 mg (50 mmol) of the urea resin is swollen in dimethylformamide then 35 mg (250 μmol, 5 eq.) of iodomethane is added and the mixture is agitated for 18 hours at ambient temperature. The resin is filtered, rinsed with dimethylformamide, tetrahydrofuran, methanol and dichloromethane then dried under vacuum. The resin is swollen again in dichloromethane then approximately 100 mg of amberlite IRA68 resin is added and the mixture is agitated for 48 hours. The resins are filtered, rinsed with dichloromethane and the filtrate is concentrated in order to produce 18 mg (yield=78%) of a colourless oil.

NMR $^1$H(CD₃OD, 400 MHz) δ: 7.65 (m, 2H); 7.40 (m, 2H) 7.31 (m, 1H); 7.20 (t, 1H); 7.10 (m, 1H); 7.06 (m, 2H); 4.04 (m, 1H); 3.68 (s, 3H); 3.60 (t, 9H); 3.04 (t, 2H); 2.94 (m, 2H); 2.29 (s, 3H); 2.14 (m, 2H); 1.91 (m, 2H); 1.76 (m, 2H). MS/LC: m/z=459.3 (M+H).

For the R₁, X₁, X₂ and X₃ groups as illustrated in points A and B above, the R₃ groups which can be envisaged for the synthesis of trisubstituted 4-aminopiperidines according to the above procedure, are the following:

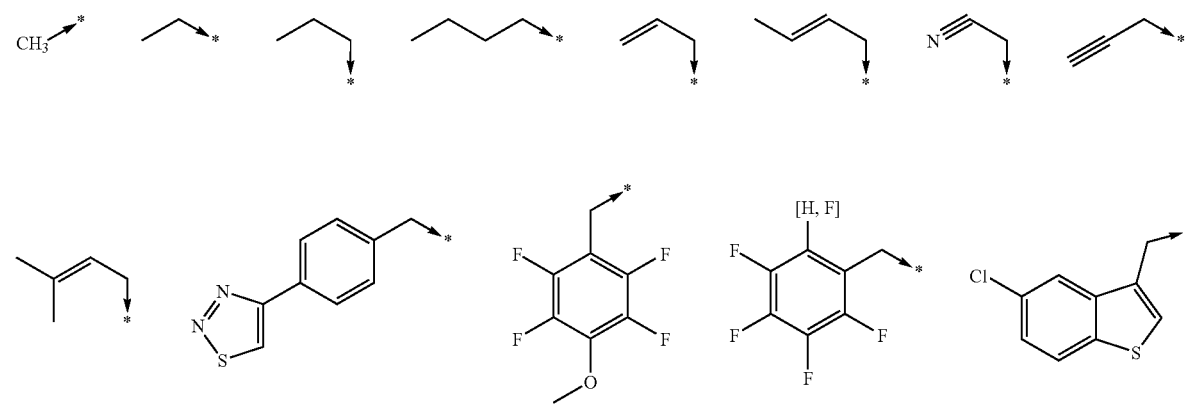

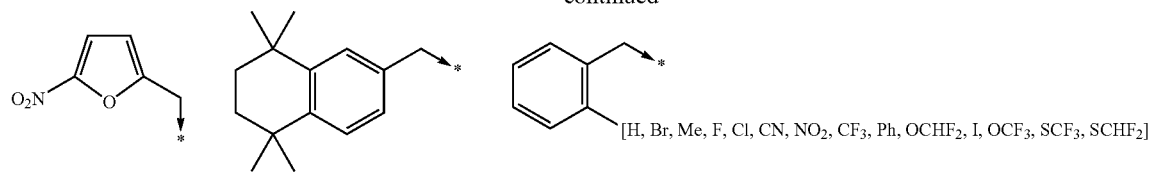
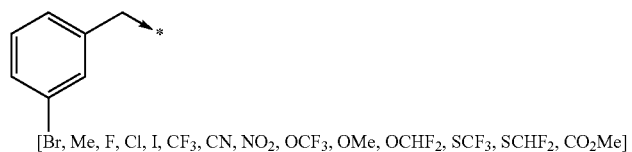
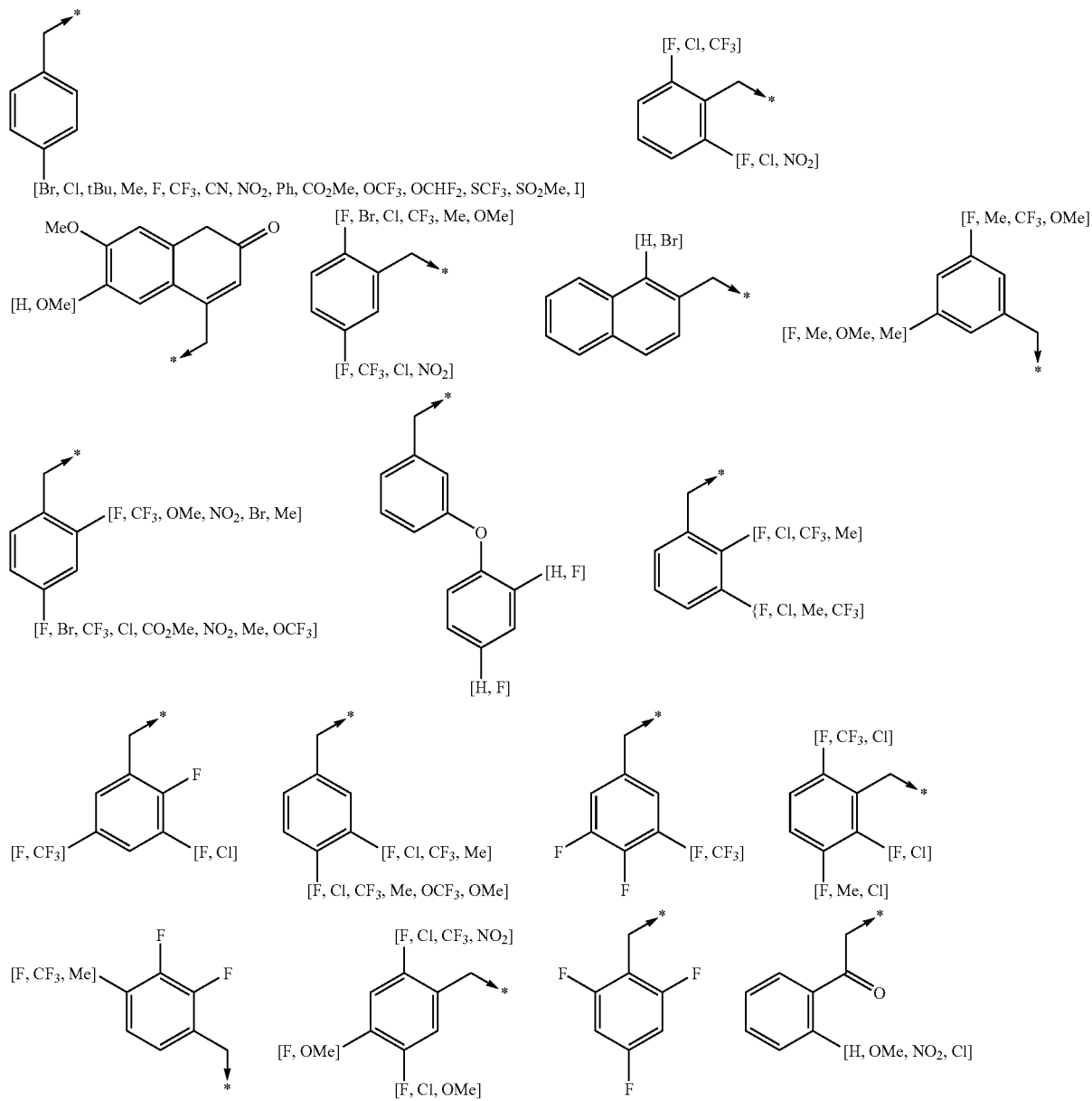

-continued
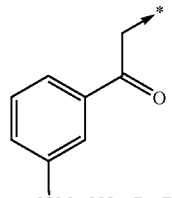
[OMe, NO2, Br, F, Cl, CN]
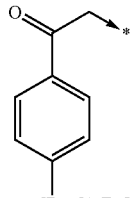
[Br, Cl, F, OMe, Ph, Me, NO2, N3, OCF3, CN, CF3, NEt2, nC4H9, nC5H11, OCH2Ph]
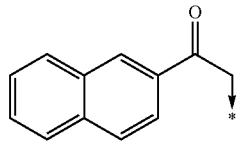
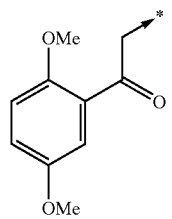
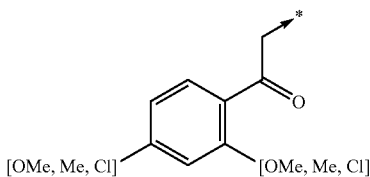
[OMe, Me, Cl]  [OMe, Me, Cl]
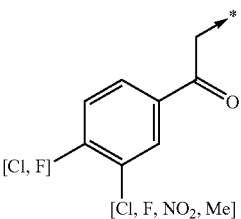
[Cl, F]  [Cl, F, NO2, Me]
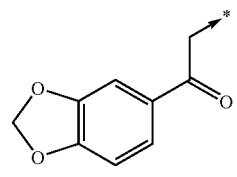
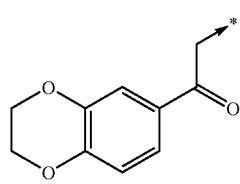
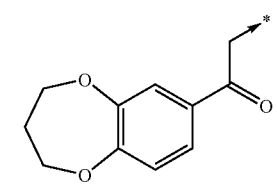
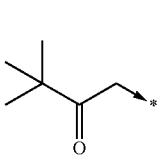
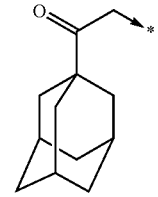
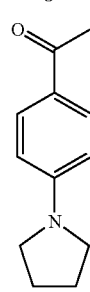
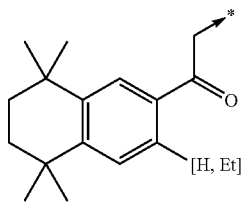
[H, Et]
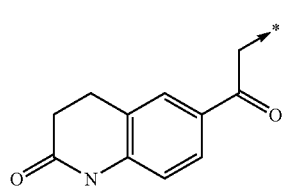
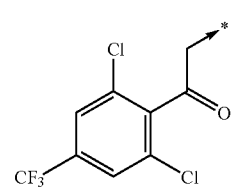
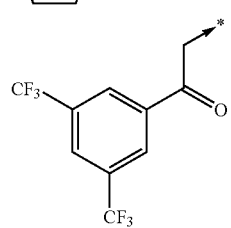
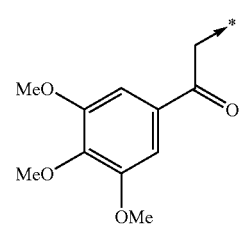
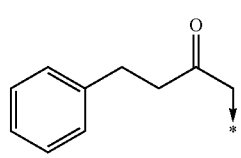
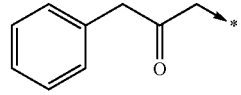
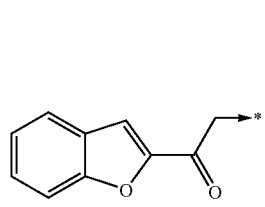
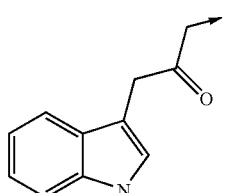
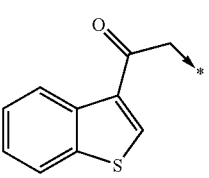
[H, Cl]
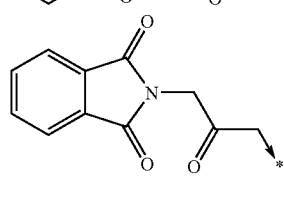
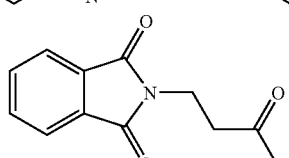
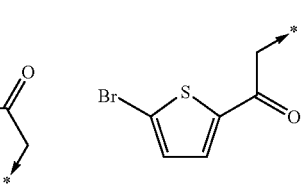

A subject of the invention is also the process for the preparation of compounds I according to the invention, in solid or liquid phase, as described previously.

A more particular subject of the invention is a process for the preparation, in liquid phase, of compounds of formula I as defined above, characterized in that it comprises the reducing amination of the following N-substituted piperidone

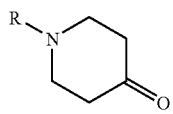

in which R represents the methyl or Boc radical, in the presence of an amine of formula $R_1NH_2$ in which $R_1$ has the meaning indicated above, in order to obtain the compound of formula 1

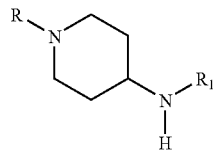
(1)

which compound of formula (1) is reacted with

A) either a compound of formula $X_1NC(Y)$ in which $X_1$ and Y have the meaning indicated above, in order to obtain a compound of formula (2)

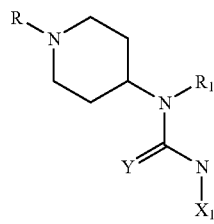
(2)

which compound of formula (2) represents the corresponding compound of formula (I) in which $R_3$ represents Me or Boc and which, when $R_3$ represents Boc, can be subjected to an acid treatment in order to obtain the corresponding compound of formula (I) in which $R_3$ represents the hydrogen atom, which compound of formula (I) thus obtained can be reacted with a compound of formula —$X_1NC(Y)$, $X_2CO_2H$ or $X_3SO_2Cl$ in which $X_1$, Y, $X_2$ and $X_3$ have the meaning indicated above, in order to obtain the corresponding compound of formula I in which $R_2$ represents a radical of formula —C(Y)$NHX_1$ and $R_3$ the —C(Y)—$NHX_1$, —C(O)$X_2$ or $SO_2X_3$ radical respectively;

B) or a compound of formula $X_2CO_2H$ in which $X_2$ has the meaning indicated above, in order to obtain a compound of formula (3)

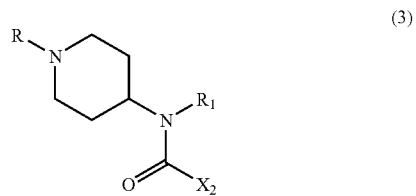
(3)

which compound of formula (3) represents the corresponding compound of formula (I) in which $R_3$ represents Me or Boc and which, when $R_3$ represents Boc, can be subjected to an acid treatment in order to obtain the corresponding compound of formula (I) in which $R_3$ represents the hydrogen atom, which compound of formula (I) thus obtained can be reacted with a compound of formula $X_1NC(Y)$, $X_2CO_2H$ or $X_3SO_2Cl$ in which $X_1$, Y, $X_2$ and $X_3$ have the meaning indicated above, in order to obtain the corresponding compound of formula I in which $R_2$ represents a radical of formula —C(O)$X_2$ and $R_3$ the —C(Y)—$NHX_1$, —C(O)$X_2$ or $SO_2X_3$ radical respectively.

A more particular subject of the invention is also a preparation process, in solid phase, for compounds of formula I as defined above, characterized in that it comprises the reducing amination of the ketonic resin

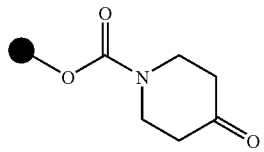

in the presence of an amine of formula $R_1NH_2$ in which $R_1$ has the meaning indicated above, in order to obtain the compound of formula (4)

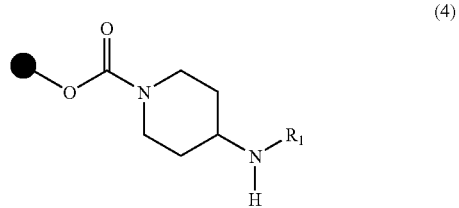
(4)

which compound of formula (4) is reacted with

A) either a compound of formula $X_1NC(Y)$ in which $X_1$ and Y have the meaning indicated above, in order to obtain a compound of formula (5)

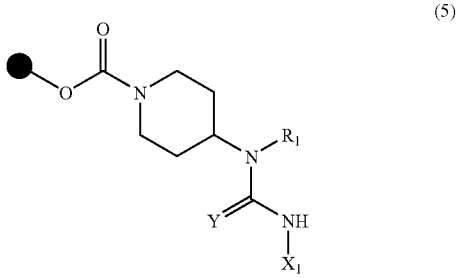
(5)

followed by cleavage of the resin in order to obtain the corresponding compound of formula (I) in which $R_3$ represents the hydrogen atom, B) or a compound of formula $X_3SO_2Cl$ in which $X_3$ has the meaning indicated above, in order to obtain a compound of formula (6)

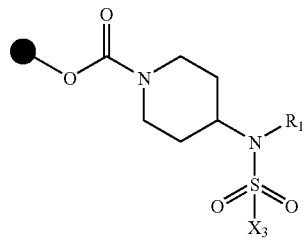

(6)

followed by cleavage of the resin in order to obtain the corresponding compound of formula (I) in which $R_3$ represents the hydrogen atom, C) or a compound of formula $X_2CO_2Cl$ in which $X_2$ has the meaning indicated above, in order to obtain a compound of formula (7)

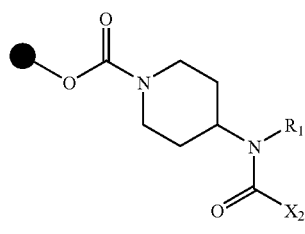

(7)

followed by cleavage of the resin in order to obtain the corresponding compound of formula (I) in which $R_3$ represents the hydrogen atom;

D) or a compound of formula $X_2CO_2H$ in which $X_2$ has the meaning indicated above, in order to obtain a compound of formula (7) as defined above, followed by cleavage of the resin in order to obtain the corresponding compound of formula (I) in which $R_3$ represents the hydrogen atom.

Finally a more particular subject of the invention is a preparation process, in solid phase, for compounds of formula I as defined above, characterized in that it comprises the reducing amination of the ketonic resin

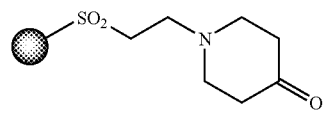

in the presence of an amine of formula $R_1NH_2$ in which $R_1$ has the meaning indicated above, in order to obtain the compound of formula (8)

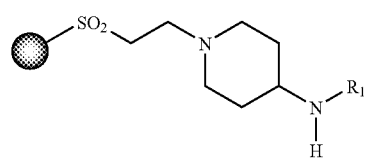

(8)

which compound of formula (8) is reacted with

A) either a compound of formula $X_1NC(O)$ in which $X_1$ has the meaning indicated above, in order to obtain a compound of formula (9)

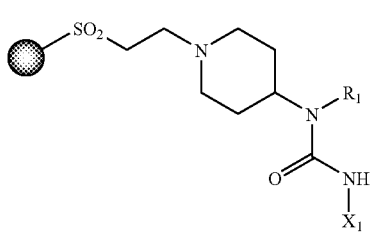

(9)

which compound (9) thus formed is reacted with a compound of formula $R_3X$ in which $R_3$ is as defined above and X represents Br or I, followed by cleavage of the resin in order to obtain the corresponding compound of formula (I);

B) or a compound of formula $X_3SO_2Cl$ in which $X_3$ has the meaning indicated above, in order to obtain a compound of formula (10)

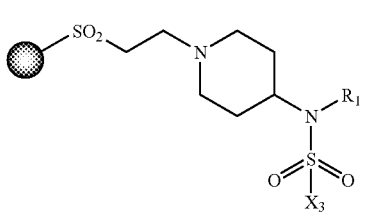

(10)

which compound (10) thus formed is reacted with a compound of formula $R_3X$ in which $R_3$ is as defined above and X represents Br or I, followed by cleavage of the resin in order to obtain the corresponding compound of formula (I);

C) or a compound of formula $X_2CO_2Cl$ in which $X_2$ has the meaning indicated above, in order to obtain a compound of formula (11)

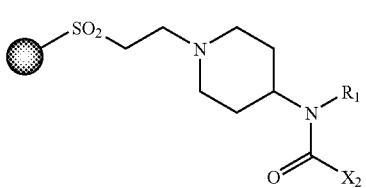

(11)

which compound (11) thus formed is reacted with a compound of formula $R_3X$ in which $R_3$ is as defined above and X represents Br or I, followed by cleavage of the resin in order to obtain the corresponding compound of formula (I);

D) or a compound of formula $X_2CO_2H$ in which $X_2$ has the meaning indicated above, in order to obtain a compound of formula (11) as defined above, which compound (11) thus formed is reacted with a compound of formula $R_3X$ in which $R_3$ is as defined above and X represents Br or I, followed by cleavage of the resin in order to obtain the corresponding compound of formula (I).

Compounds I of the present invention have useful pharmacological properties. Thus it has been discovered that compounds I of the present invention have a high affinity for one (or more) of the somatostatin receptors. They can be used as non-peptide agonists or antagonists of somatostatin in a selective or non-selective manner.

The compounds of the present invention can therefore be used in different therapeutic applications. They can advantageously be used to treat the pathological states or the diseases as presented above and in which one (or more) of the somatostatin receptors are involved.

An illustration of the pharmacological properties of the compounds of the invention will be found hereafter in the experimental part.

A subject of the present Application is also, as medicaments, the products of formula I as defined above, as well as the addition salts with pharmaceutically acceptable mineral or organic acids of said products of formula I, as well as the pharmaceutical compositions containing, as active ingredient, at least one of the medicaments as defined above, in combination with a pharmaceutically acceptable support.

The pharmaceutical composition can be in the form of a solid, for example, powders, granules, tablets, gelatin capsules or suppositories. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax.

The pharmaceutical compositions containing a compound of the invention can also be presented in liquid form, for example, solutions, emulsions, suspensions or syrups. Appropriate liquid supports can be, for example, water, organic solvents such as glycerol or glycols, similarly their mixtures, in varying proportions, in water, with added pharmaceutically acceptable oils or fats. The sterile liquid compositions can be used for intramuscular, intraperitoneal or subcutaneous injections and the sterile compositions can also be administered intravenously.

Some compounds of the general formula I as defined above, are covered by the patent application DE 2751138. This DE patent application described compounds which antagonise the effects of dopamine and endogenous or exogenous dopaminergic agents, and stimulate serotoninergic mechanism, activity which is far different from the activity of the compounds of the present invention.

A subject of the present invention is also the use of compounds of general formula $I_a$

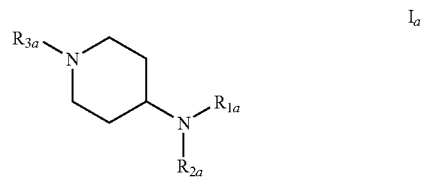

in racemic, enantiomeric form or all combinations of these forms, in which:

$R_{1a}$ represents a linear or branched $(C_1-C_{16})$alkyl, alkenyl, alkynyl, $—(CH_2)_m—Y—Z_{11}$ or $—(CH_2)_m—Z_{12}$ radical in which $Z_{11}$ represents a $(C_1-C_6)$alkyl or aryl optionally substituted, $Z_{12}$ represents cyano, cyclohexenyl, bis-phenyl, $(C_3-C_7)$ cycloalkyl, optionally substituted $(C_3-C_7)$ heterocycloalkyl, optionally substituted aryl or optionally substituted heteroaryl, or $Z_{12}$ represents a radical of formula

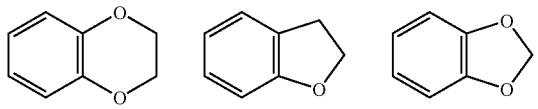

or $R_{1a}$ represents a radical of formula

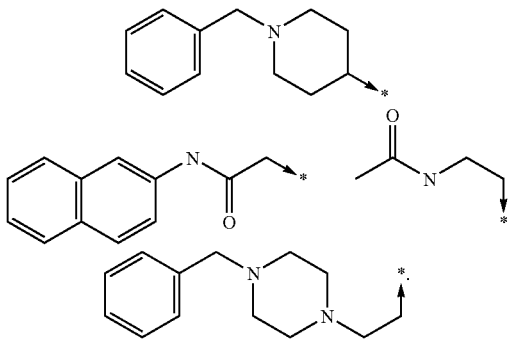

$R_{2a}$ represents a radical of formula $—C(Y)NHX_1, —C(O)X_2$ or $SO_2X_3$;

$R_{3a}$ represents the hydrogen atom, an optionally substituted alkyl, alkenyl, alkynyl, optionally substituted aralkyl, optionally substituted heteroarylalkyl radical, or a radical of formula $—C(Y)—NHX_1, —(CH_2)_n—C(O)X_2, SO_2X_3$ or

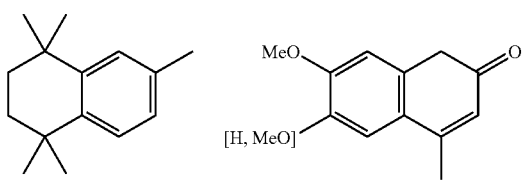

$X_1$ represents a linear or branched $(C_1-C_{15})$alkyl, alkenyl, alkynyl, $-(CH_2)_m-Y-Z_{21}$ or $-(CH_2)_p Z_{22}$ radical in which $Z_{21}$ represents a $(C_1-C_6)$alkyl $Z_{22}$ represents cyclohexenyl, indanyl, bis-phenyl, $(C_3-C_7)$cycloalkyl, $(C_3-C_7)$heterocycloalkyl, mono- or di-alkylamino, $-C(O)-O$-alkyl, or aryl or heteroaryl optionally substituted, or $Z_{22}$ represents a radical of formula

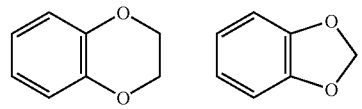

$X_2$ represents a linear or branched $(C_1-C_{10})$alkyl radical, an alkenyl radical optionally substituted by a phenyl radical (the phenyl radical being itself optionally substituted), an alkynyl radical, or a radical of formula $-(CH_2)_m-W-(CH_2)_q-Z_{23}$ or $-(CH_2)_p-U-Z_{24}$ in which $Z_{23}$ represents a $(C_1-C_6)$alkyl or aryl optionally substituted;

$Z_{24}$ represents alkyl, cyclohexenyl, bis-phenyl, $(C_3-C_7)$cycloalkyl optionally substituted, $(C_3-C_7)$heterocycloalkyl, cyano, amino, mono or di-alkylamino, or aryl or heteroaryl optionally substituted, or $Z_{24}$ represents a radical of formula

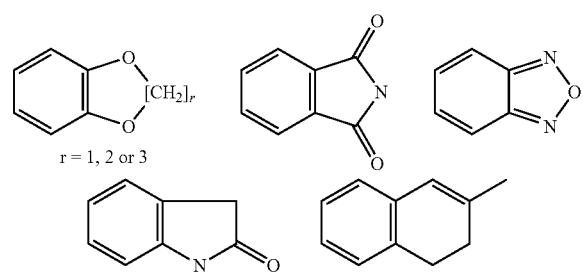

r = 1, 2 or 3 or $X_2$ represents a radical represented below:

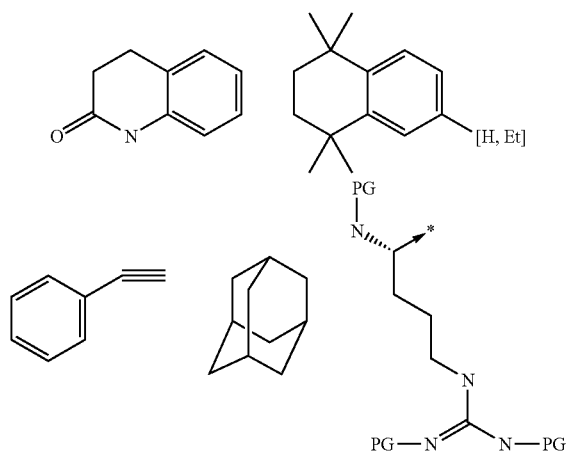

-continued

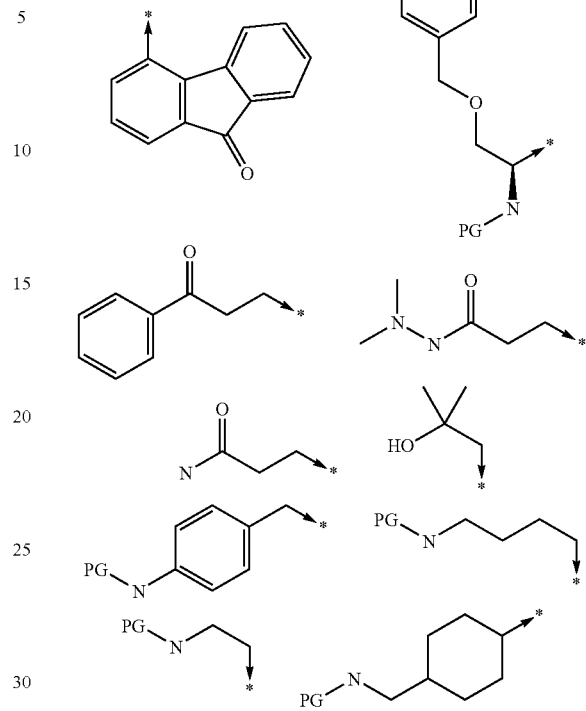

where the protective group (PG) represents H or tert-butyloxycarbonyl;

$X_3$ represents a linear or branched $(C_1-C_{10})$alkyl radical, an alkenyl radical optionally substituted by a phenyl radical (the phenyl radical being itself optionally substituted), $CF_3$, or $-(CH_2)_p Z_{25}$ in which $Z_{25}$ represents aryl or heteroaryl optionally substituted, or $X_3$ represents a radical of formula

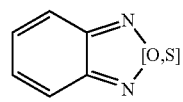

optionally substituted by one or more halo radicals identical or different;

Y represents an oxygen or sulphur atom;

W represents an oxygen or sulphur atom, or $SO_2$;

U represents a covalent bond or the oxygen atom;

n is an integer from 0 to 4;

m is an integer from 1 to 6;

p is an integer from 0 to 6;

q is an integer from 0 to 2, or their addition salts with pharmaceutically acceptable mineral or organic acids, for the preparation of a medicament intended to treat pathological states or diseases in which one (or more) receptor(s) of somatostatin is (are) involved.

A more particularly subject of the invention is the use of products of general formula $I_a$ as defined above, characterized in that i) the substituent or substituents which can be carried by the aryl radicals represented by $Z_{11}$ and $Z_{12}$ and heteroaryl represented by $Z_{12}$ are chosen independently from the fluoro, chloro, bromo, iodo, alkyl, alkoxy, alkylthio, —$CF_3$, —$OCF_3$, phenyl, phenoxy, aminosulphonyl radicals;

ii) the substituent or substituents which can be carried by the heterocycloalkyl radical represented by $Z_{12}$ are chosen independently from the oxy and alkyl radicals;

iii) the substituent or substituents which can be carried by the aryl and heteroaryl radicals represented by $Z_{22}$ are chosen independently from the fluoro, chloro, bromo, iodo, alkyl, alkenyl, alkoxy, alkylthio, $CF_3$, $OCF_3$, nitro, cyano, azido, aminosulphonyl, piperidinosulphonyl, mono- or di-alkylamino, —C(O)—O-alkyl, —C(O)-alkyl, or phenyl, phenoxy, phenylthio, benzyloxy radicals, the phenyl radical being able to be substituted;

iv) the substituent or substituents which can be carried by the aryl radicals represented by $Z_{23}$ and $Z_{24}$, cycloalkyl and heteroaryl represented by $Z_{24}$ are chosen independently from the fluoro, chloro, bromo, iodo, alkyl, alkoxy, alkylthio, $CF_3$, $OCF_3$, $OCHF_2$, $SCF_3$, nitro, cyano, azido, hydroxy, —C(O)O-alkyl, —O—C(O)-alkyl, —NH—C(O)-alkyl, alkylsulphonyl, mono- or di-alkylamino, amino, aminoalkyl, pyrrolyl, pyrrolydinyl or the radicals phenyl, phenoxy, phenylthio, benzyl, benzyloxy radicals the aryl radical of which is optionally substituted by one or more alkyl, $CF_3$ or halo radicals;

v) the substituent or substituents which can be carried by the aryl and heteroaryl radicals represented by $Z_{25}$ are chosen independently from the fluoro, chloro, bromo, iodo, alkyl, alkoxy, $CF_3$, $OCF_3$, nitro, cyano, —NH—C(O)-alkyl, alkylsulphonyl, amino, mono- and di-alkylamino, phenyl, pyridino radicals;

vi) the substituent which can be carried by the alkyl radical represented by $R_3$ is the cyano radical.

vii) the substituent or substituents which can be carried by the aralkyl radical represented by $R_3$ are chosen independently from the fluoro, chloro, bromo, iodo, alkyl, alkoxy, $CF_3$, $OCF_3$, $OCHF_2$, $SCF_3$, $SCHF_2$, nitro, cyano, —C(O)O-alkyl, alkylsulphonyl, thiadiazolyl radicals, or the phenyl and phenoxy radicals the phenyl radical of which is optionally substituted by one or more halo radicals.

viii) the substituent or substituents which can be carried by the heteroarylalkyl radical represented by $R_3$ are chosen independently from the fluoro, chloro, bromo or nitro radicals.

A more particular subject of the present invention is the use of compounds of general formula $I_a$ as defined above in which $R_{1a}$ represents a linear or branched ($C_1$-$C_6$)alkyl radical, the —$(CH_2)_m$—Y—$Z_{11}$ or —$(CH_2)_m$—$Z_{12}$ radical in which $Z_{11}$ represents a ($C_1$-$C_6$)alkyl, $Z_{12}$ represents bis-phenyl, ($C_3$-$C_7$)cycloalkyl, ($C_3$-$C_7$)heterocycloalkyl optionally substituted, or aryl or heteroaryl optionally substituted by one or more substituents chosen independently from the fluoro, chloro, bromo, iodo, alkyl, alkoxy radicals, or $Z_{12}$ represents

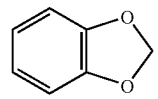

Y represents the oxygen atom, or $R_{1a}$ represents a radical of formula

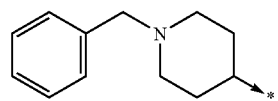

A more particular subject of the present invention is the use of compounds of general formula $I_a$ as defined above in which $R_{2a}$ represents a radical of formula —C(Y)NHX$_1$, —C(O)X$_2$ or SO$_2$X$_3$ in which $X_1$ represents a linear or branched ($C_1$-$C_{15}$)alkyl radical, or —$(CH_2)_p Z_{22}$ in which $Z_{22}$ represents cyclohexenyl, bis-phenyl, ($C_3$-$C_7$)cycloalkyl, ($C_3$-$C_7$)heterocycloalkyl, mono- or di-alkylamino, —C(O)—O-alkyl, or aryl or heteroaryl optionally substituted by one or more radicals chosen independently from the fluoro, chloro, bromo, iodo, alkyl, alkoxy, alkylthio, $CF_3$, $OCF_3$, nitro, cyano, azido, piperidinosulphonyl, —C(O)—O-alkyl, —C(O)-alkyl, or phenyl radicals, or $Z_{22}$ represents a radical of formula

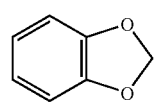

$X_2$ represents a linear or branched ($C_1$-$C_{10}$)alkyl, alkynyl, —$(CH_2)_m$—W—$(CH_2)_q$—$Z_{23}$ or —$(CH_2)_p$—U—$Z_{24}$ radical in which W represents $SO_2$, U represents a covalent bond, $Z_{23}$ represents an aryl radical;

$Z_{24}$ represents cyclohexenyl, bis-phenyl, ($C_3$-$C_7$)cycloalkyl optionally substituted by an aminoalkyl, or aryl or heteroaryl radical optionally substituted by one or more radicals chosen from fluoro, chloro, bromo, iodo, alkyl, alkoxy, —$CF_3$, —$OCF_3$, $SCF_3$, hydroxy, —O—C(O)-alkyl, mono- or di-alkylamino, amino or $Z_{24}$ represents a radical of formula

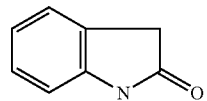 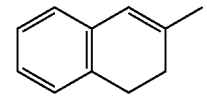

or $X_2$ represents

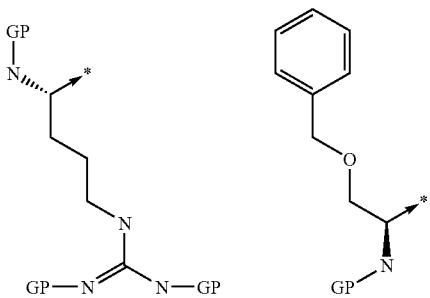

$X_3$ represents a —$(CH_2)_p Z_{25}$ radical in which $Z_{25}$ represents an aryl radical optionally substituted by one or more identical or different radicals chosen from alkoxy and $CF_3$.

A more particular subject of the present invention is the use of compounds of general formula $I_a$ as defined above in which $R_{3a}$ represents the hydrogen atom, an alkyl alkenyl, heteroarylalkyl radical optionally substituted or a radical of formula —$C(Y)$—$NHX_1$, —$C(O)X_2$ or $SO_2X_3$ in which $X_1$ represents a —$(CH_2)_p Z_{22}$ radical in which $Z_{22}$ represents an aryl radical optionally substituted by one or more radicals chosen independently from the fluoro, chloro, bromo, iodo, alkyl, alkoxy $CF_3$, nitro, phenoxy radicals;

$X_2$ represents the vinyl radical substituted by a phenyl, the phenyl radical being itself optionally substituted by one or more halo, or —$(CH_2)_p$—U—$Z_{24}$ radicals in which $Z_{24}$ represents alkyl, $(C_3-C_7)$cycloalkyl, $(C_3-C_7)$heterocycloalkyl, bis-phenyl, amino, mono or di-alkylamino, or aryl or heteroaryl optionally substituted by one or more radicals chosen from alkoxy, bromo, chloro, fluoro, hydroxy, $CF_3$, nitro, amino, mono- and di-alkylamino, pyrrolyl, or $X_2$ represents a radical of formula

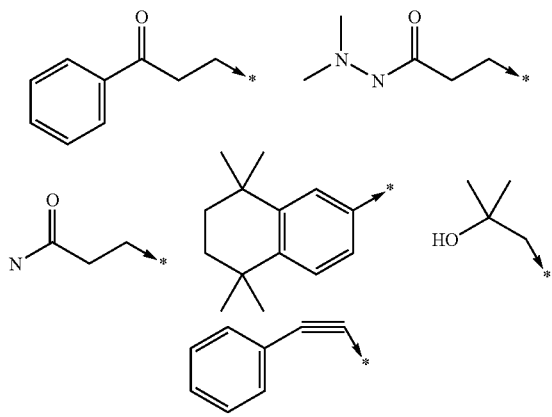

$X_3$ represents a linear or branched $(C_1-C_{10})$alkyl radical, the vinyl radical substituted by a radical (the phenyl radical being itself optionally substituted), $CF_3$, or —$(CH_2)_p Z_{25}$ in which $Z_{25}$ represents aryl or heteroaryl optionally substituted by one or more substituents chosen independently from the fluoro, chloro, bromo, iodo, alkyl, alkoxy, $CF_3$, nitro, —NH—C(O)-alkyl, mono- and di-alkylamino radicals.

Preferentially, $R_{1a}$ represents a linear or branched $(C_1-C_6)$ alkyl radical, the —$(CH_2)_n$—Y—$Z_{11}$ or —$(CH_2)_m$—$Z_{12}$ radical in which $Z_{11}$ represents a $(C_1-C_6)$alkyl, $Z_{12}$ represents naphthyl, morpholino, bis-phenyl, pyrrolidinyl substituted by the oxy radical, or the phenyl, piperazinyl, pyridinyl and indolyl radicals which are optionally substituted by one or more substituents chosen independently from the bromo, fluoro, chloro, alkyl, alkoxy, —$CF_3$, —$OCF_3$ radicals;

or $Z_{12}$ represents

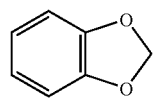

Y represents the oxygen atom, or $R_{1a}$ represents a radical of formula given below:

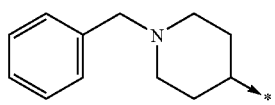

Preferentially, $R_{2a}$ represents a radical of formula —$C(Y)$ $NHX_1$, —$C(O)X_2$ or $SO_2X_3$ in which $X_1$ represents a linear or branched $(C_1-C_{10})$alkyl, or —$(CH_2)_p Z_{22}$ radical in which $Z_{22}$ represents cyclohexyl, cyclohexenyl, bis-phenyl, morpholino, piperidino, mono- or di-alkylamino, —C(O)—O-alkyl, or phenyl, naphthyl or furyl optionally substituted by one or more radicals chosen independently from the fluoro, chloro, bromo, iodo, alkyl, alkoxy, alkylthio, $CF_3$, $OCF_3$, nitro, cyano, azido, piperidinosulphonyl, —C(O)—O— alkyl, —C(O)-alkyl or phenyl radicals, or $Z_{22}$ represents a radical of formula

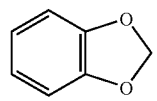

$X_2$ represents an alkyl, alkynyl, —$(CH_2)_m$—W—$(CH_2)_q$—$Z_{23}$ or —$(CH_2)_p Z_{24}$ radical in which W represents $SO_2$;

$Z_{23}$ represents the phenyl radical;

$Z_{24}$ represents cyclohexenyl, bis-phenyl, cyclohexyl optionally substituted by an aminoalkyl, or phenyl, naphthyl, benzothienyl, thienyl or indolyl radical optionally substituted by one or more radicals chosen from fluoro, chloro, bromo, iodo, alkyl, alkoxy, —$CF_3$, —$OCF_3$, $SCF_3$, hydroxy, —O—C(O)-alkyl, —NH—C(O)-alkyl, mono- or di-alkylamino, amino, or $Z_{24}$ represents a radical of formula or $X_2$ represents $X_3$ represents a —$(CH_2)_pZ_{25}$ radical in which $Z_{25}$ represents the phenyl radical optionally substituted by one or more identical or different radicals chosen from alkoxy and $CF_3$, Preferentially, $R_{3a}$ represents the hydrogen atom, an alkyl, alkenyl or furyl-methyl radical substituted by one or more nitro radicals, or a radical of formula —C(Y)—NHX$_1$, —C(O)X$_2$ or SO$_2$X$_3$ in which $X_1$ represents a —$(CH_2)_pZ_{22}$ radical in which
$Z_{22}$ represents the phenyl or naphthyl radical optionally substituted by one or more radicals chosen independently from the fluoro, chloro, bromo, iodo, alkyl, alkoxy, $CF_3$, nitro, phenoxy radicals, $X_2$ represents the vinyl radical substituted by a phenyl radical itself optionally substituted by one or more halo, or —$(CH_2)_p$—U—$Z_{24}$ radicals in which
$Z_{24}$ represents alkyl, cyclohexyl, tetrahydrofuryl, bis-phenyl, amino, mono or di-alkylamino, or phenyl, indolyl, thienyl, pyridinyl, benzothienyl and furyl optionally substituted by one or more radicals chosen from alkoxy, bromo, chloro, fluoro, amino, mono- and di-alkylamino, nitro, hydroxy, pyrrolyl or $X_2$ represents a radical of formula $X_3$ represents a linear or branched $(C_1$-$C_{10})$alkyl radical, the vinyl radical substituted by a phenyl, $CF_3$, or —$(CH_2)_pZ_{25}$ radical in which
$Z_{25}$ represents a phenyl, naphtyl, thienyl, pyrazolyl or thiazolyl radical optionally substituted by one or more substituents chosen independently from the fluoro, chloro, bromo, iodo, alkyl, alkoxy, $CF_3$, nitro, —NH—C(O)-alkyl, mono- and di-alkylamino radicals;

Very preferentially, $R_{1a}$ represents the —$(CH_2)_mZ_{12}$ radical in which m=2 and $Z_{12}$ represents bis-phenyl or the radical indolyl substituted by one or more substituents chosen independently from the alkyl and alkoxy radicals.

Very preferentially, $R_{2a}$ represents the radicals of formula —C(Y)NHX$_1$ and —C(O)X$_2$ in which
Y represents S;
$X_1$ represents a phenyl radical optionally substituted by one or more azido radicals,
$X_2$ represents —$(CH_2)_pZ_{24}$ in which
p is equal to 1, 2 or 3,
$Z_{24}$ represents cyclohexyl, or phenyl or benzothienyl optionally substituted by one or more radicals chosen from fluoro, chloro, bromo, iodo or —CF$_3$.

Very preferentially, $R_{3a}$ represents the hydrogen atom or the methyl radical.

All the technical and scientific terms used in the present text have the meaning known to a person skilled in the art. Furthermore, all patents (or patent applications) as well as other bibliographical references are incorporated by way of reference.

Experimental Part:

Other compounds according to the invention obtained according to the procedures of Examples A, B, C and D described previously, are set out in the table below.

The compounds are characterized by their retention time (rt), expressed in minutes, and their molecular peak (M+H+) determined by mass spectroscopy (MS).

For the mass spectroscopy, a single quadripole mass spectrometer (Micromass, Platform model) equipped with an electrospray source is used with a resolution of 0.8 Da at 50% valley. The conditions for Examples 1 to 778 below, are as follows:

Conditions C1 and C2
Eluent: A: Water+0.02% trifluoracetic acid; B: acetonitrile

| T (min) | A % | B % |
| --- | --- | --- |
| 0 | 100 | 0 |
| 1 | 100 | 0 |
| 10 | 15 | 85 |
| 12 | 15 | 85 |

| Condition C1 | Condition C2 |
| --- | --- |
| Flow rate: 1.1 ml/min | Flow rate: 1.1 ml/min |
| Injection: 5 µl | Injection: 20 µl |
| Temp: 40° C | Temp: 40° C |
| Wavelength (% UV): 210 nm | Wavelength (% UV): 210 nm |
| Column: Uptisphere ODS 3 µm | Column: Kromasyl ODS 3.5 µm |
| 33 * 4.6 mm i.d | 50 * 4.6 mm i.d |

Conditions C3
Eluent: A: Water+0.02% trifluoracetic acid; B: acetonitrile

| T (min) | A % | B % |
|---------|-----|-----|
| 0       | 90  | 10  |
| 6       | 15  | 85  |
| 10      | 15  | 85  |

Flow rate: 1 ml/min
Injection: 5 μl
Column: Uptisphere ODS 3 μm 50*4.6 mm i.d
Temp: 40° C.
Wavelength (% UV): 220 nm The conditions depending on the examples, are as follows:

| Examples   | Conditions |
|------------|------------|
| 1 to 29    | C2         |
| 30 to 263  | C1         |
| 264 to 425 | C3         |
| 426 to 456 | C2         |
| 457 to 503 | C3         |
| 504 to 586 | C1         |
| 587 to 778 | C3         |

These examples are presented to illustrate the above procedures and should in no way be considered as limiting the scope of the invention.

| Ex | R₁ | R₂ | R₃ | Purity (%) | rt | M + H+ |
|----|----|----|----|------------|-----|--------|
| 1 | 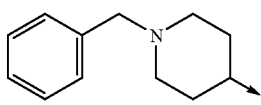 | 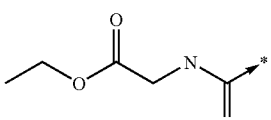 | 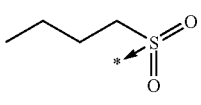 | 66 | 7.6 | 523.3 |
| 2 | " | " | 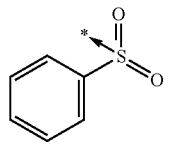 | 94 | 7.7 | 543.2 |
| 3 | " | " | 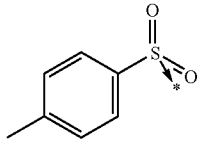 | 96 | 8.1 | 557.2 |
| 4 | " | " | 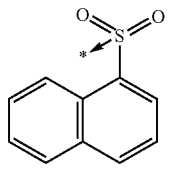 | 98 | 8.5 | 593.2 |
| 5 | " | " | 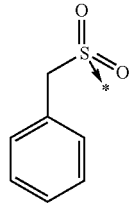 | 95 | 7.8 | 557.2 |
| 6 | " | " |  | 97 | 8.1 | 623.1 |

-continued
| Ex | R₁ | R₂ | R₃ | Purity (%) | rt | M + H+ |
|---|---|---|---|---|---|---|
| 7 | " | " | 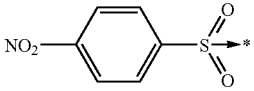 | 95 | 8.1 | 588.2 |
| 8 | " | " | 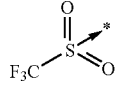 | 19 | 8.1 | 535.2 |
| 9 | " | " | 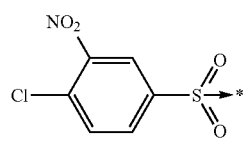 | 99 | 8.5 | 622.2 |
| 10 | " | " | 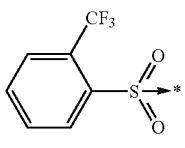 | 80 | 8.4 | 611.2 |
| 11 | " | " | 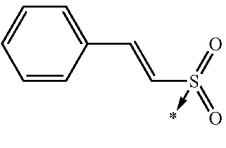 | 99 | 8.2 | 569.2 |
| 12 | " | " | 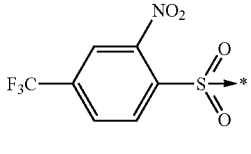 | 93 | 8.9 | 656.2 |
| 13 | " | " | 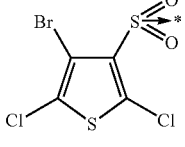 | 85 | 9.1 | 697.0 |
| 14 | " | " | 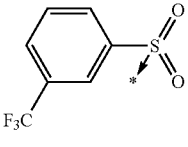 | 95 | 8.7 | 611.2 |
| 15 | " | " | 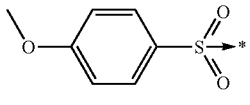 | 87 | 7.8 | 573.2 |
| 16 | " | " | 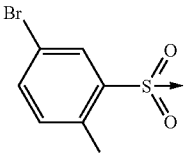 | 100 | 8.4 | 653.2 |

-continued
| Ex | R₁ | R₂ | R₃ | Purity (%) | rt | M + H+ |
|---|---|---|---|---|---|---|
| 17 | " | " | 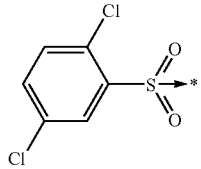 | 97 | 8.6 | 611.1 |
| 18 | " | " | 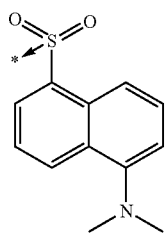 | 99 | 8.7 | 636.3 |
| 19 | " | " | 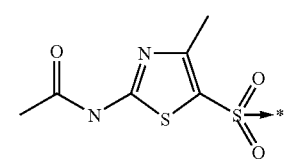 | 83 | 7.2 | 621.2 |
| 20 | " | " | 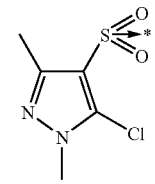 | 98 | 7.4 | 595.2 |
| 21 | " | " | 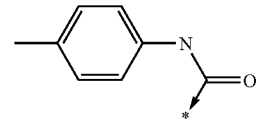 | 84 | 7.4 | 536.3 |
| 22 | " | " | 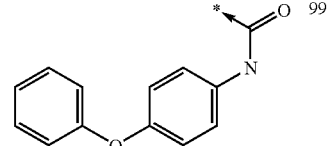 | 99 | 8.4 | 614.3 |
| 23 | " | " | 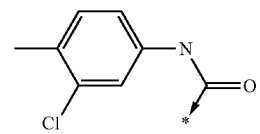 | 63 | 8.2 | 570.2 |
| 24 | " | " | 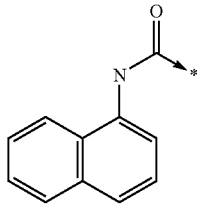 | 92 | 7.5 | 572.3 |

-continued
| Ex | R₁ | R₂ | R₃ | Purity (%) | rt | M + H+ |
|---|---|---|---|---|---|---|
| 25 | " | " | 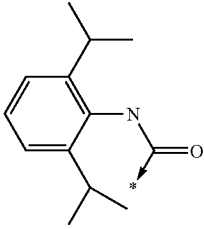 | 93 | 8.4 | 606.4 |
| 26 | " | " | 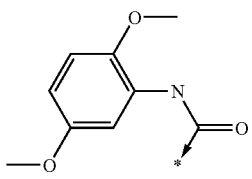 | 96 | 7.4 | 582.3 |
| 27 | " | " | 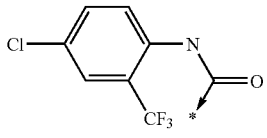 | 93 | 8.1 | 624.2 |
| 28 | " | " | 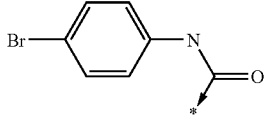 | 93 | 7.8 | 602.2 |
| 29 | " | " | 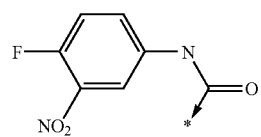 | 95 | 7.4 | 585.2 |
| 30 | " | " | 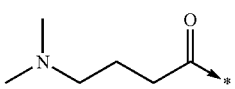 | 87.39 | 4.0 | 516.4 |
| 31 | " | " | 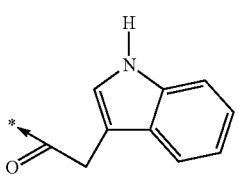 | 92 | 5.5 | 560.3 |
| 32 | " | " | 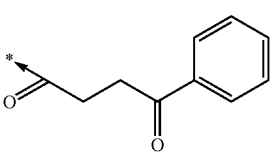 | 90 | 5.7 | 563.3 |
| 33 | " | " | 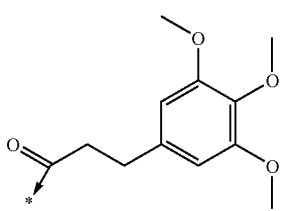 | 87.73 | 5.6 | 625.4 |

-continued

| Ex | R₁ | R₂ | R₃ | Purity (%) | rt | M + H+ |
|---|---|---|---|---|---|---|
| 34 | " | " | 4-phenoxybutanoyl | 85.41 | 6.0 | 565.4 |
| 35 | " | " | 4,5-dibromothiophene-2-carbonyl | 98.4 | 6.4 | 671.1 |
| 36 | " | " | 2-chloropyridine-3-carbonyl | 86 | 4.9 | 542.3 |
| 37 | " | " | 4-(1H-pyrrol-1-yl)benzoyl | 89 | 6.1 | 572.3 |
| 38 | " | " | 4-cyclohexylbutanoyl | 77.61 | 6.8 | 555.4 |
| 39 | " | " | 4-(2,2-dimethylhydrazinyl)-4-oxobutanoyl | 89.16 | 4.2 | 545.4 |
| 40 | " | " | 3-(phenylsulfonyl)propanoyl | 92.32 | 5.3 | 599.3 |
| 41 | " | " | 2-(2,6-dichlorophenyl)acetyl | 83 | 6.0 | 589.2 |
| 42 | " | " | 3-phenylpropioloyl | 36.3 | 5.9 | 531.2 |
| 43 | " | " | 4-(thiophen-2-yl)butanoyl | 83.27 | 5.9 | 555.3 |
| 44 | " | " | 2-(4-(dimethylamino)phenyl)acetyl | 82 | 4.5 | 564.4 |

-continued

| Ex | R₁ | R₂ | R₃ | Purity (%) | rt | M + H+ |
|---|---|---|---|---|---|---|
| 45 | " | " | benzothiophen-3-yl-CH₂-C(O)-* | 86.75 | 6.0 | 577.3 |
| 46 | " | " | tetrahydrofuran-2-yl-C(O)-* | 91.95 | 4.7 | 501.4 |
| 47 | " | " | CH₃O-CH₂-C(O)-* | 88.94 | 4.5 | 475.3 |
| 48 | " | " | 5-nitrofuran-2-yl-C(O)-* | 73 | 5.3 | 542.3 |
| 49 | " | butyl-NH-C(O)-* | (CH₃)₂N-(CH₂)₃-C(O)-* | 90.96 | 4.4 | 486.4 |
| 50 | " | " | 1H-indol-3-yl-CH₂-C(O)-* | 95.5 | 5.9 | 530.4 |
| 51 | " | " | Ph-C(O)-CH₂-CH₂-C(O)-* | 94.51 | 6.1 | 533.4 |
| 52 | " | " | 3,4,5-trimethoxyphenyl-CH₂-CH₂-C(O)-* | 93.64 | 6.0 | 595.4 |
| 53 | " | " | PhO-(CH₂)₃-C(O)-* | 96.05 | 6.5 | 535.4 |
| 54 | " | " | 4,5-dibromothiophen-2-yl-C(O)-* | 84.68 | 6.9 | 641.1 |

-continued
| Ex | R₁ | R₂ | R₃ | Purity (%) | rt | M + H+ |
|---|---|---|---|---|---|---|
| 55 | " | " | 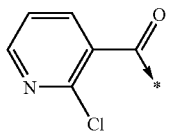 | 86 | 5.5 | 512.3 |
| 56 | " | " | 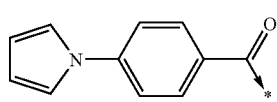 | 92 | 6.5 | 542.4 |
| 57 | " | " | 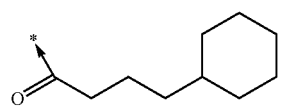 | 91.29 | 7.2 | 525.5 |
| 58 | " | " | 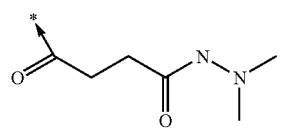 | 94.7 | 4.7 | 515.4 |
| 59 | " | " | 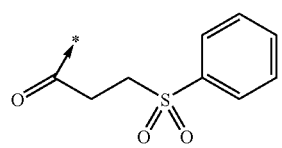 | 94 | 5.8 | 569.3 |
| 60 | " | " | 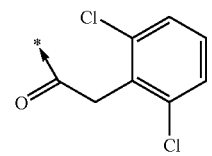 | 89.43 | 6.6 | 559.3 |
| 61 | " | " | 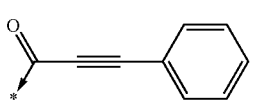 | 32 | 6.9 | 501.5 |
| 62 | " | " | 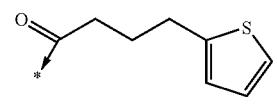 | 93.53 | 6.4 | 525.4 |
| 63 | " | " | 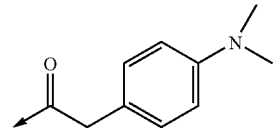 | 94.7 | 4.9 | 534.4 |
| 64 | " | " | 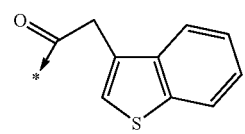 | 94.32 | 6.4 | 547.3 |
| 65 | " | " | 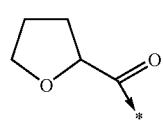 | 91.71 | 5.2 | 471.4 |

-continued

| Ex | R₁ | R₂ | R₃ | Purity (%) | rt | M + H+ |
|---|---|---|---|---|---|---|
| 66 | " | " | methoxyacetyl | 92.47 | 5.0 | 445.4 |
| 67 | " | " | 5-nitro-furan-2-carbonyl | 58 | 5.9 | 512.3 |
| 68 | " | morpholinoethyl-thiourea | 4-(dimethylamino)butanoyl | 84.55 | 3.6 | 559.4 |
| 69 | " | " | 1H-indol-3-yl-acetyl | 87.7 | 4.7 | 603.4 |
| 70 | " | " | 4-oxo-4-phenylbutanoyl | 90.77 | 4.8 | 606.4 |
| 71 | " | " | 3-(3,4,5-trimethoxyphenyl)propanoyl | 72.34 | 4.8 | 668.4 |
| 72 | " | " | 4-phenoxybutanoyl | 87.18 | 5.1 | 608.4 |
| 73 | " | " | 4,5-dibromothiophene-2-carbonyl | 69.52 | 5.4 | 714.1 |
| 74 | " | " | 2-chloropyridine-3-carbonyl | 63.39 | 4.2 | 585.3 |
| 75 | " | " | 4-(1H-pyrrol-1-yl)benzoyl | 54.46 | 5.1 | 615.4 |

-continued
| Ex | R₁ | R₂ | R₃ | Purity (%) | rt | M + H+ |
|---|---|---|---|---|---|---|
| 76 | " | " | 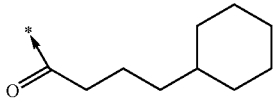 | 87.3 | 5.7 | 598.4 |
| 77 | " | " | 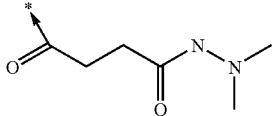 | 96.1 | 3.8 | 588.4 |
| 78 | " | " | 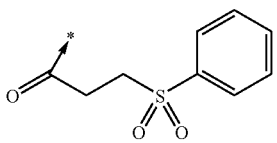 | 89.9 | 4.5 | 642.3 |
| 79 | " | " | 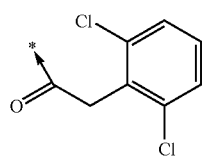 | 61.5 | 5.1 | 632.3 |
| 80 | " | " | 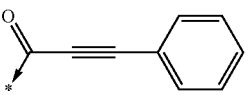 | 43.65 | 5.0 | 574.3 |
| 81 | " | " | 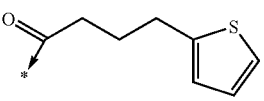 | 88.18 | 5.0 | 598.3 |
| 82 | " | " | 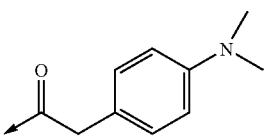 | 88.6 | 4.0 | 607.4 |
| 83 | " | " | 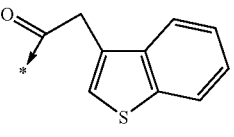 | 90.08 | 5.1 | 620.3 |
| 84 | " | " | 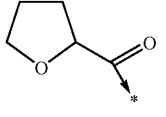 | 85.57 | 4.0 | 544.3 |
| 85 | " | " | 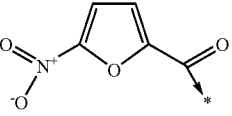 | 48.41 | 4.5 | 585.3 |
| 86 | " | 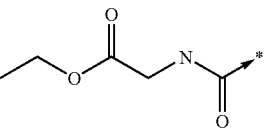 | 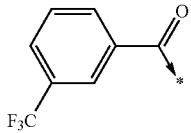 | 82.68 | 6.1 | 589.3 |

-continued

| Ex | R₁ | R₂ | R₃ | Purity (%) | rt | M + H+ |
|---|---|---|---|---|---|---|
| 87 | " | " | 3,3-diphenylpropanoyl | 79.99 | 6.5 | 611.4 |
| 88 | " | " | 3-hydroxy-3-methylbutanoyl | 86.07 | 4.8 | 503.4 |
| 89 | " | " | 3-(4-hydroxyphenyl)propanoyl | 82 | 5.1 | 551.4 |
| 90 | " | " | 4-amino-4-oxobutanoyl | 19.44 | 4.4 | 502.4 |
| 91 | " | " | 3-(dimethylamino)benzoyl | 86.48 | 5.1 | 550.4 |
| 92 | " | " | (E)-3-(4-chlorophenyl)acryloyl | 80 | 6.3 | 567.3 |
| 93 | " | butyl-NHC(O)-* | 3-(trifluoromethyl)benzoyl | 94.62 | 6.6 | 559.3 |
| 94 | " | " | 3,3-diphenylpropanoyl | 57.01 | 6.9 | 581.4 |
| 95 | " | " | 3-hydroxy-3-methylbutanoyl | 92 | 5.2 | 473.4 |
| 96 | " | " | 3-(4-hydroxyphenyl)propanoyl | 87.4 | 5.6 | 521.4 |

-continued

| Ex | R₁ | R₂ | R₃ | Purity (%) | rt | M + H+ |
|---|---|---|---|---|---|---|
| 97 | " | " | *-C(O)-CH₂CH₂-C(O)NH₂ | 20.99 | 5.0 | 472.4 |
| 98 | " | " | 3-(dimethylamino)benzoyl* | 88.63 | 5.7 | 520.4 |
| 99 | " | " | (E)-3-(4-chlorophenyl)acryloyl* | 84 | 6.7 | 537.3 |
| 100 | " | 2-morpholinoethyl-NH-C(=S)-* | 3-(trifluoromethyl)benzoyl* | 89.71 | 5.2 | 632.3 |
| 101 | " | " | *-C(O)-CH₂-CH(Ph)₂ | 90.25 | 5.5 | 654.4 |
| 102 | " | " | *-C(O)-CH₂-C(CH₃)₂-OH | 90.09 | 4.0 | 546.4 |
| 103 | " | " | *-C(O)-CH₂CH₂-(4-hydroxyphenyl) | 71 | 4.4 | 594.3 |
| 104 | " | " | *-C(O)-CH₂CH₂-C(O)NH₂ | 37.19 | 3.8 | 545.3 |
| 105 | " | " | 3-(dimethylamino)benzoyl* | 76.55 | 4.5 | 593.4 |
| 106 | *-CH₂CH₂-(2-pyridyl) | n-butyl-NH-C(O)-* | *-C(O)-O-C(CH₃)₃ | 69.62 | 5.9 | 405.2 |

-continued
| Ex | R₁ | R₂ | R₃ | Purity (%) | rt | M + H+ |
|---|---|---|---|---|---|---|
| 107 | 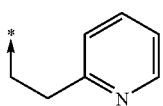 | 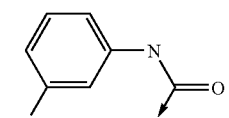 | " | 98 | 7.1 | 493.2 |
| 108 | 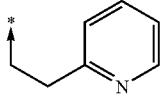 | 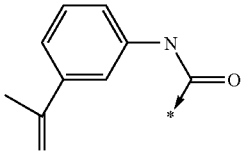 | " | 80 | 6.0 | 467.3 |
| 109 | 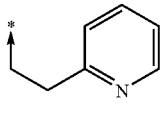 | 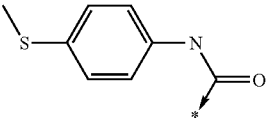 | " | 88 | 6.5 | 471.2 |
| 110 | 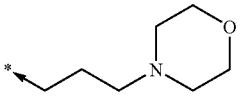 | 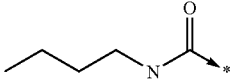 | " | 60.04 | 5.7 | 427.3 |
| 111 | 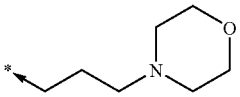 | 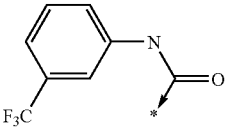 | " | 78 | 6.5 | 515.2 |
| 112 | 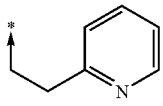 | 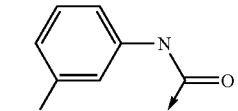 | " | 97 | 6.2 | 455.2 |
| 113 | 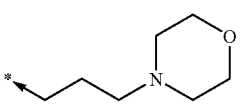 | 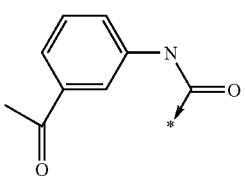 | " | 70 | 5.7 | 489.3 |
| 114 | 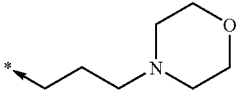 | 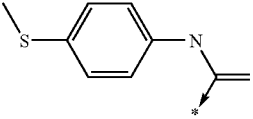 | " | 90 | 6.2 | 493.3 |
| 115 | 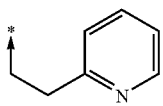 | 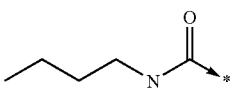 | 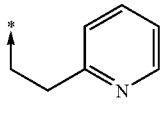 | 62.88 | 3.6 | 305.3 |
| 116 | 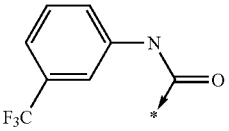 | | " | 82.99 | 4.7 | 393.2 |

-continued
| Ex | R₁ | R₂ | R₃ | Purity (%) | rt | M + H+ |
|---|---|---|---|---|---|---|
| 117 | 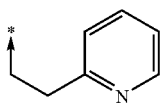 | 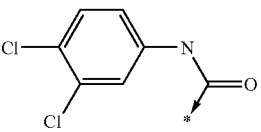 | " | 74.42 | 5.0 | 393.1 |
| 118 | 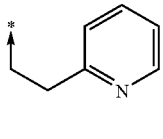 | 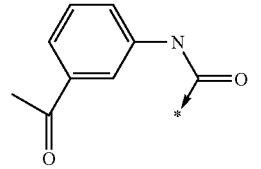 | " | 10.53 | 5.4 | 367.3 |
| 119 | 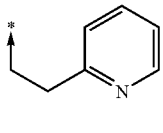 | 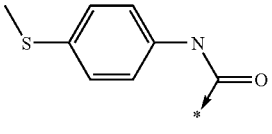 | " | 74.79 | 4.3 | 371.2 |
| 120 | 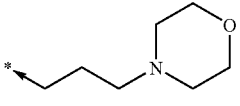 | 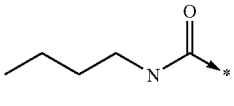 | " | 50.14 | 3.4 | 327.3 |
| 121 | 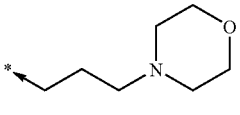 | 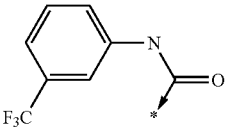 | " | 70 | 4.3 | 415.2 |
| 122 | 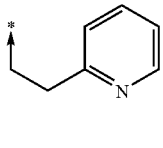 | 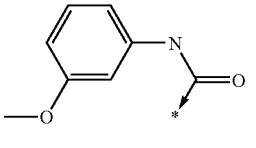 | " | 84 | 3.9 | 355.3 |
| 123 | 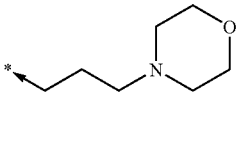 | 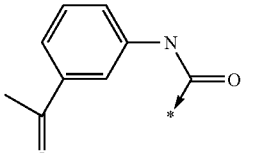 | " | 66 | 3.5 | 389.3 |
| 124 | 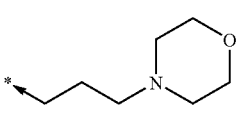 | 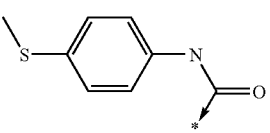 | " | 94.61 | 3.9 | 393.2 |
| 125 | 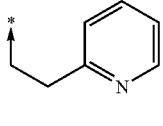 | 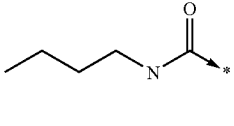 | 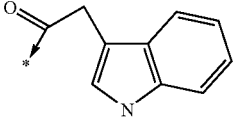 | 71 | 5.5 | 462.3 |
| 126 | 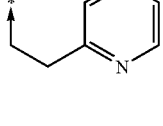 | 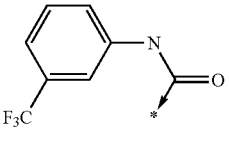 | " | 52 | 6.6 | 550.2 |

-continued
| Ex | R₁ | R₂ | R₃ | Purity (%) | rt | M + H+ |
|---|---|---|---|---|---|---|
| 127 | 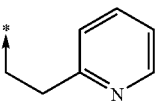 | 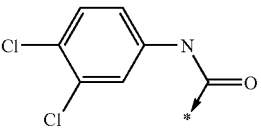 | " | 57 | 6.8 | 550.1 |
| 128 | 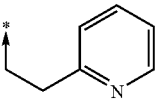 | 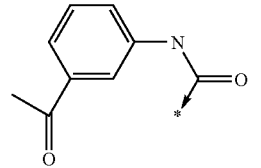 | " | 60 | 5.6 | 524.2 |
| 129 | 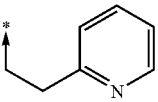 | 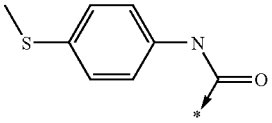 | " | 64 | 6.1 | 528.2 |
| 130 | 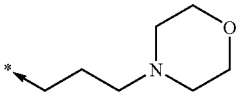 | 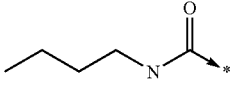 | " | 27 | 5.4 | 484.3 |
| 131 | 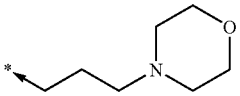 | 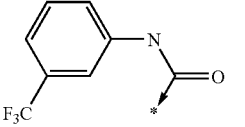 | " | 51 | 6.2 | 572.2 |
| 132 | 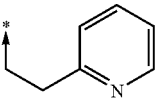 | 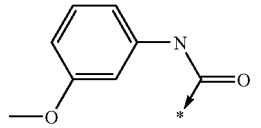 | " | 73 | 5.7 | 512.2 |
| 133 | 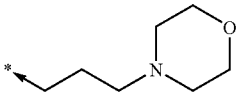 | 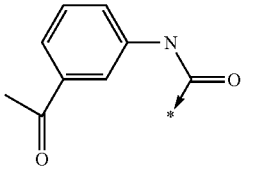 | " | 61 | 5.4 | 546.2 |
| 134 | 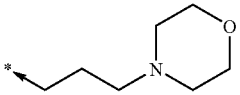 | 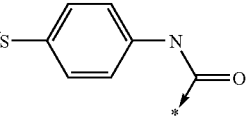 | " | 43 | 5.8 | 550.2 |
| 135 | 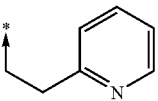 | 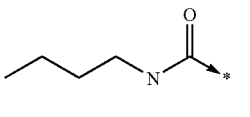 | 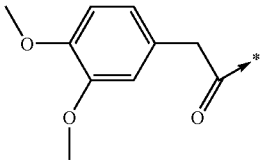 | 76 | 5.3 | 483.3 |
| 136 | 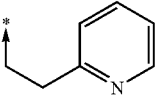 | 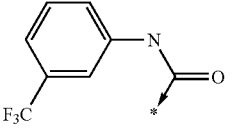 | " | 49 | 6.4 | 571.2 |

-continued
| Ex | R$_1$ | R$_2$ | R$_3$ | Purity (%) | rt | M + H+ |
|---|---|---|---|---|---|---|
| 137 | 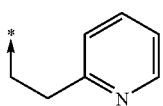 | 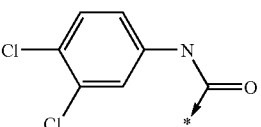 | " | 63 | 6.6 | 571.1 |
| 138 | 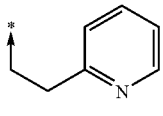 | 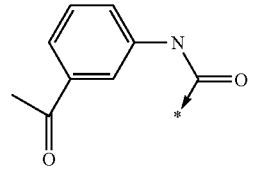 | " | 79 | 5.4 | 545.2 |
| 139 | 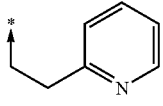 | 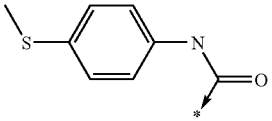 | " | 57 | 5.9 | 549.2 |
| 140 | 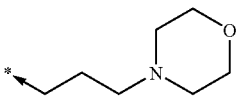 | 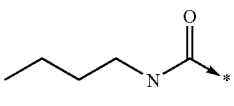 | " | 66.58 | 5.2 | 505.3 |
| 141 | 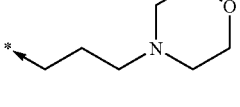 | 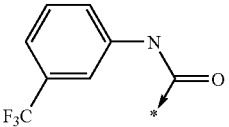 | " | 61 | 6.0 | 593.2 |
| 142 | 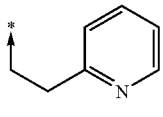 | 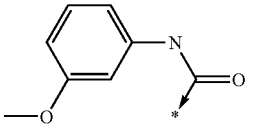 | " | 67 | 5.5 | 533.2 |
| 143 | 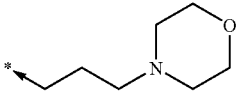 | 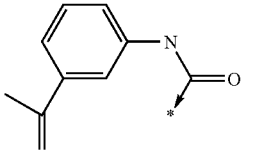 | " | 61 | 5.2 | 567.3 |
| 144 | 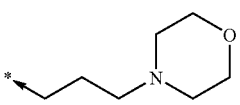 | 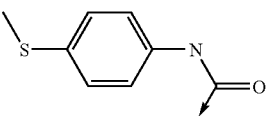 | " | 51 | 5.6 | 571.2 |
| 145 | 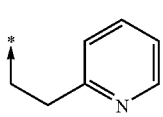 | 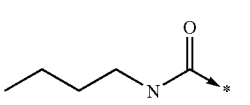 | 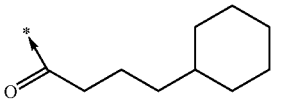 | 56 | 7.0 | 457.3 |
| 146 | 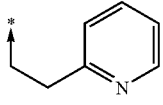 | 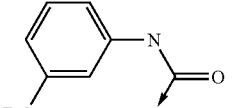 | " | 64 | 8.1 | 545.2 |

-continued
| Ex | R₁ | R₂ | R₃ | Purity (%) | rt | M + H+ |
|---|---|---|---|---|---|---|
| 147 | 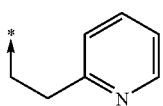 | 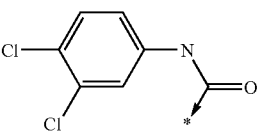 | " | 52 | 8.3 | 545.2 |
| 148 | 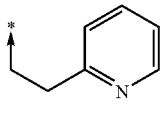 | 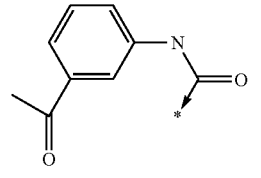 | " | 69 | 7.1 | 519.3 |
| 149 | 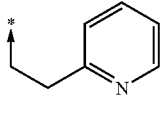 | 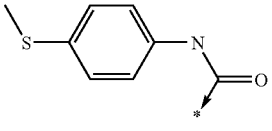 | " | 70 | 7.6 | 523.3 |
| 150 | 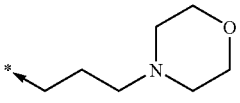 | 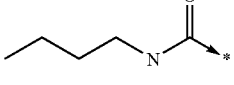 | " | 63.77 | 6.7 | 479.4 |
| 151 | 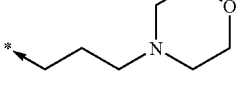 | 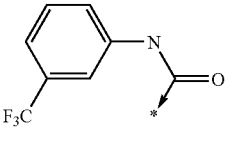 | " | 50 | 7.3 | 567.3 |
| 152 | 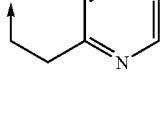 | 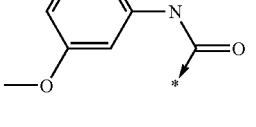 | " | 46 | 7.3 | 507.3 |
| 153 | 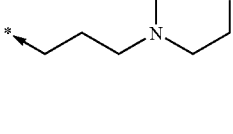 | 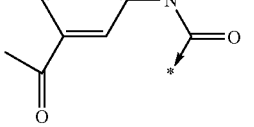 | " | 78 | 6.7 | 541.3 |
| 154 | 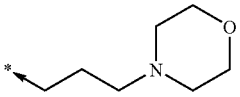 | 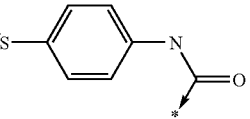 | " | 66 | 7.0 | 545.3 |
| 155 | 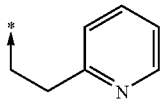 | 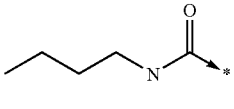 | 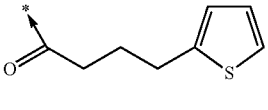 | 68 | 6.0 | 457.2 |
| 156 | 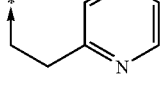 | 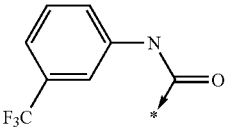 | " | 65 | 7.1 | 545.2 |

-continued
| Ex | R₁ | R₂ | R₃ | Purity (%) | rt | M + H+ |
|---|---|---|---|---|---|---|
| 157 | 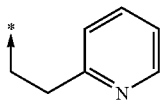 | 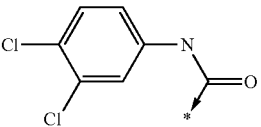 | " | 67 | 7.3 | 545.1 |
| 158 | 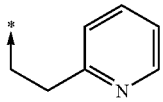 | 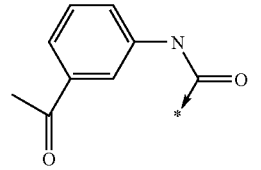 | " | 66 | 6.1 | 519.2 |
| 159 | 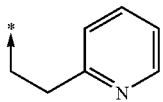 | 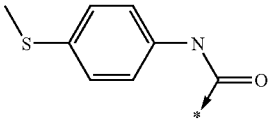 | " | 77 | 6.6 | 523.2 |
| 160 | 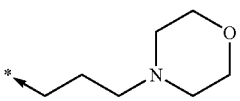 | 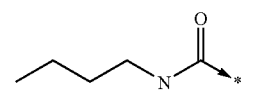 | " | 60.49 | 5.8 | 479.3 |
| 161 | 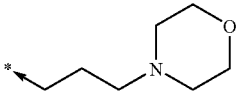 | 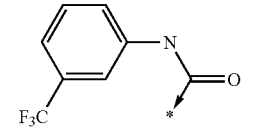 | " | 60 | 6.6 | 567.3 |
| 162 | 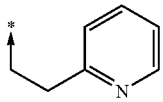 | 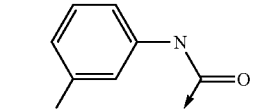 | " | 69 | 6.2 | 507.2 |
| 163 | 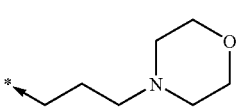 | 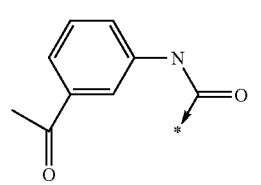 | " | 50 | 5.8 | 541.2 |
| 164 | 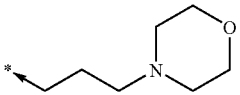 | 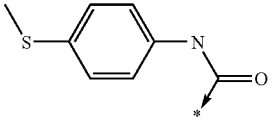 | " | 49 | 6.2 | 545.2 |
| 165 | 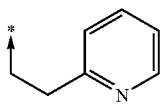 | 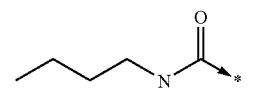 | 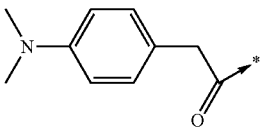 | 67 | 4.4 | 466.3 |
| 166 | 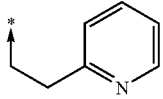 | 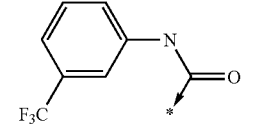 | " | 45 | 5.5 | 554.2 |

-continued

| Ex | R₁ | R₂ | R₃ | Purity (%) | rt | M + H+ |
|---|---|---|---|---|---|---|
| 167 | 2-pyridyl-CH₂CH₂-* | 3,4-dichlorophenyl-NH-C(=O)-* | " | 65.89 | 5.7 | 554.1 |
| 168 | 2-pyridyl-CH₂CH₂-* | 3-acetylphenyl-NH-C(=O)-* | " | 5 | 5.4 | 528.2 |
| 169 | 2-pyridyl-CH₂CH₂-* | 4-(methylthio)phenyl-NH-C(=O)-* | " | 64.08 | 5.0 | 532.2 |
| 170 | morpholino-(CH₂)₃-* | n-butyl-NH-C(=O)-* | " | 62.51 | 4.3 | 488.3 |
| 171 | morpholino-(CH₂)₃-* | 3-(trifluoromethyl)phenyl-NH-C(=O)-* | " | 55 | 5.2 | 576.3 |
| 172 | 2-pyridyl-CH₂CH₂-* | 3-methoxyphenyl-NH-C(=O)-* | " | 50.35 | 4.7 | 516.3 |
| 173 | morpholino-(CH₂)₃-* | 3-acetylphenyl-NH-C(=O)-* | " | 7 | 5.2 | 550.3 |
| 174 | morpholino-(CH₂)₃-* | 4-(methylthio)phenyl-NH-C(=O)-* | " | 48.63 | 4.8 | 554.3 |
| 175 | 2-pyridyl-CH₂CH₂-* | n-butyl-NH-C(=O)-* | *-C(=O)-CH₂-(2,4-difluorophenyl) | 53 | 5.7 | 459.2 |
| 176 | 2-pyridyl-CH₂CH₂-* | 3-(trifluoromethyl)phenyl-NH-C(=O)-* | " | 49 | 6.9 | 547.2 |

-continued
| Ex | R₁ | R₂ | R₃ | Purity (%) | rt | M + H+ |
|---|---|---|---|---|---|---|
| 177 | 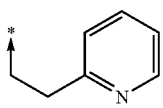 | 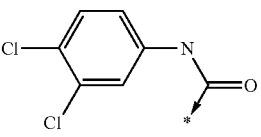 | " | 61 | 7.1 | 547.1 |
| 178 | 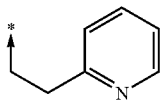 | 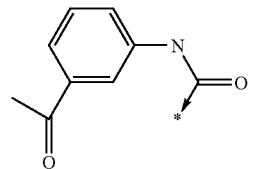 | " | 57 | 5.9 | 521.2 |
| 179 | 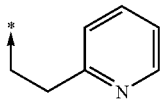 | 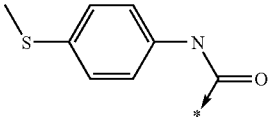 | " | 65 | 6.4 | 525.2 |
| 180 | 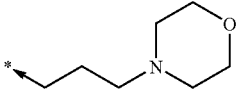 | 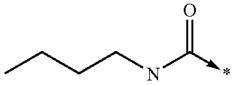 | " | 88.99 | 5.6 | 481.3 |
| 181 | 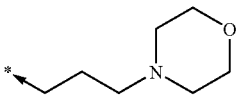 | 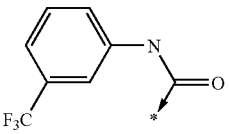 | " | 58 | 6.4 | 569.2 |
| 182 | 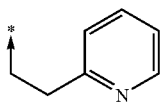 | 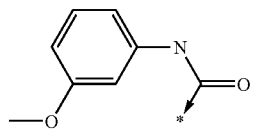 | " | 64 | 6.0 | 509.2 |
| 183 | 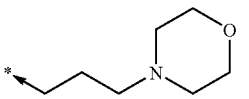 | 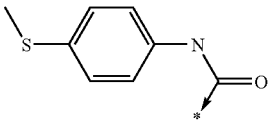 | " | 63 | 6.0 | 547.2 |
| 184 | 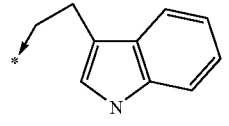 | 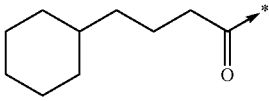 | 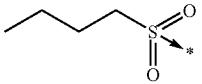 | 67.83 | 10.1 | 516.3 |
| 185 | 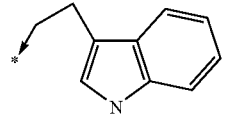 | 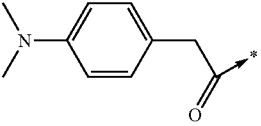 | " | 61.66 | 6.7 | 525.3 |
| 186 | 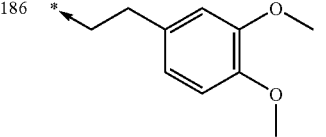 | 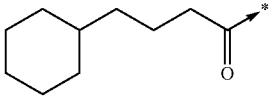 | " | 40.48 | 9.9 | 537.3 |

-continued
| Ex | R₁ | R₂ | R₃ | Purity (%) | rt | M + H+ |
|---|---|---|---|---|---|---|
| 187 | 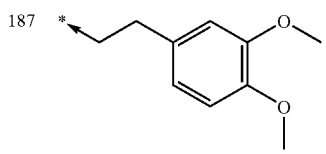 | 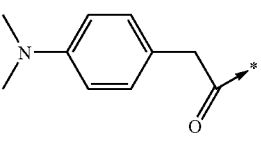 | " | 50 | 6.4 | 546.3 |
| 188 | 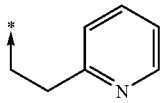 | 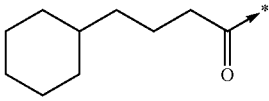 | " | 42.57 | 7.4 | 478.4 |
| 189 | 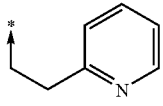 | 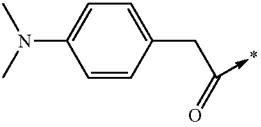 | " | 29 | 4.8 | 487.3 |
| 190 | 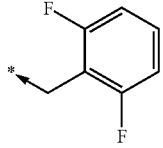 | 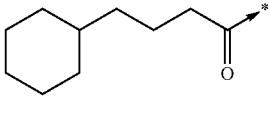 | " | 55 | 10.3 | 499.3 |
| 191 | 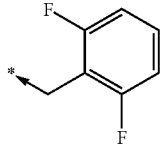 | 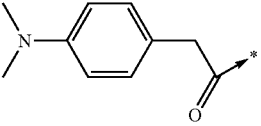 | " | 19.39 | 6.7 | 508.3 |
| 192 | 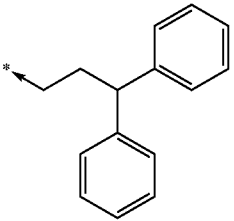 | 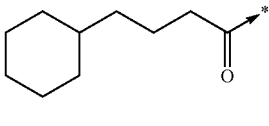 | " | 67 | 11.1 | 567.3 |
| 193 | 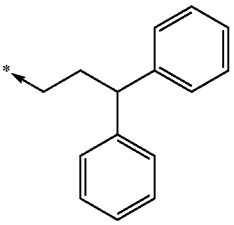 | 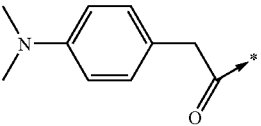 | " | 64.73 | 7.9 | 576.3 |
| 194 | 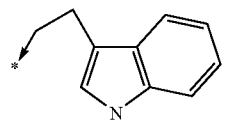 | 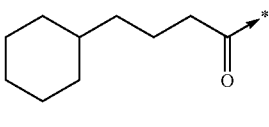 | 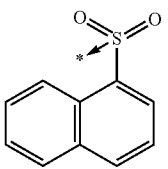 | 92 | 10.6 | 586.3 |
| 195 | 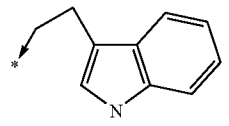 | 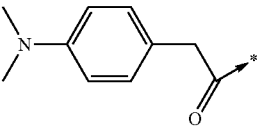 | " | 85 | 7.3 | 595.3 |

-continued
| Ex | R₁ | R₂ | R₃ | Purity (%) | rt | M + H+ |
|---|---|---|---|---|---|---|
| 196 | 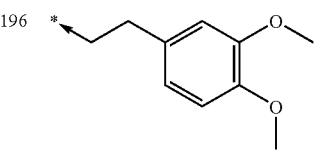 | 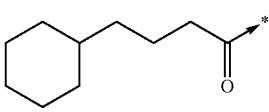 | " | 96 | 10.5 | 607.3 |
| 197 | 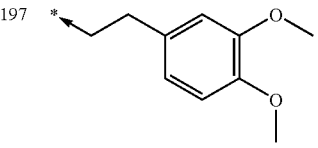 | 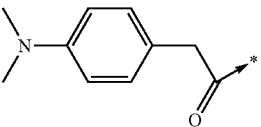 | " | 89.25 | 7.2 | 616.3 |
| 198 | 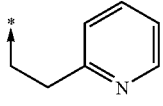 | 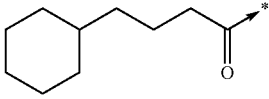 | " | 98.24 | 7.9 | 548.3 |
| 199 | 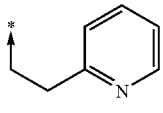 | 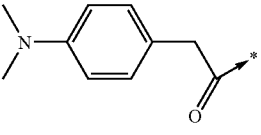 | " | 94 | 5.6 | 557.3 |
| 200 | 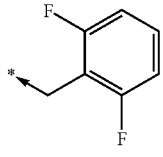 | 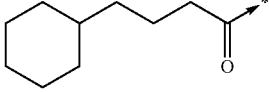 | " | 98 | 10.8 | 569.2 |
| 201 | 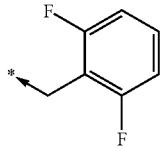 | 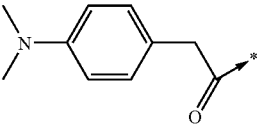 | " | 93.17 | 7.3 | 578.2 |
| 202 | 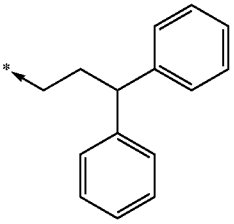 | 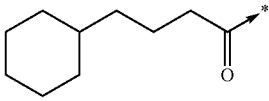 | " | 97.82 | 11.7 | 637.3 |
| 203 | 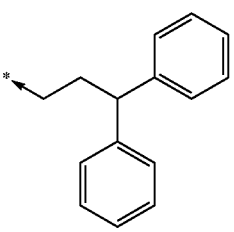 | 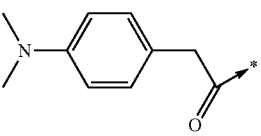 | " | 88.11 | 8.5 | 646.3 |
| 204 | 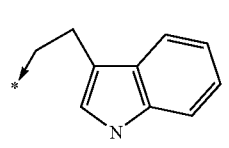 | 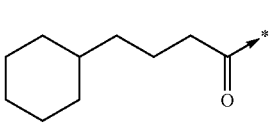 | 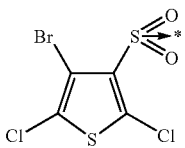 | 73 | 11.2 | 690.0 |

-continued
| Ex | R₁ | R₂ | R₃ | Purity (%) | rt | M + H+ |
|---|---|---|---|---|---|---|
| 205 | 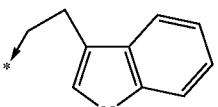 | 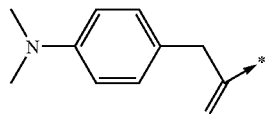 | " | 60.44 | 7.9 | 699.0 |
| 206 | 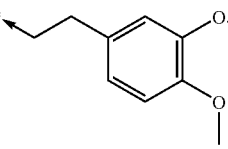 | 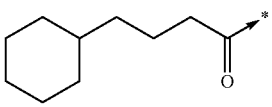 | " | 76 | 11.1 | 711.0 |
| 207 | 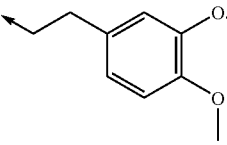 | 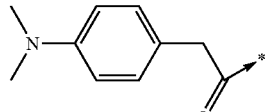 | " | 72.2 | 7.8 | 720.0 |
| 208 | 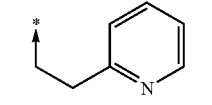 | 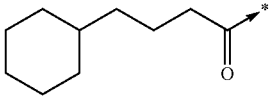 | " | 89.42 | 8.5 | 652 |
| 209 | 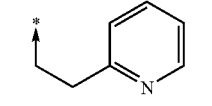 | 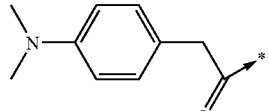 | " | 48 | 6.2 | 659.0 |
| 210 | 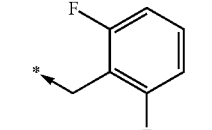 | 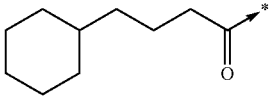 | " | 78.2 | 11.6 | 673.0 |
| 211 | 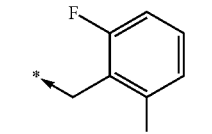 | 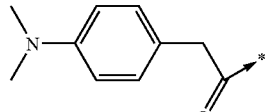 | " | 66.1 | 7.9 | 682.0 |
| 212 | 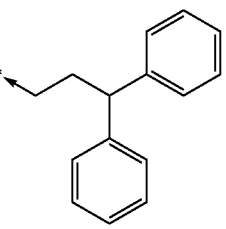 | 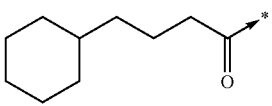 | " | 78 | 12.6 | 739.1 |
| 213 | 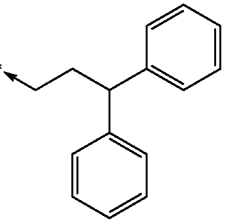 | 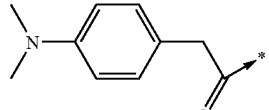 | " | 88.77 | 9.1 | 750.0 |

-continued

| Ex | R₁ | R₂ | R₃ | Purity (%) | rt | M + H+ |
|---|---|---|---|---|---|---|
| 214 | 3-(indol-3-yl)ethyl | 4-cyclohexylbutanoyl | 3-(trifluoromethyl)phenylsulfonyl | 73 | 10.6 | 604.3 |
| 215 | 3-(indol-3-yl)ethyl | 4-(dimethylamino)phenylacetyl | " | 67 | 7.5 | 613.2 |
| 216 | 3,4-dimethoxyphenethyl | 4-cyclohexylbutanoyl | " | 73 | 10.5 | 625.3 |
| 217 | 3,4-dimethoxyphenethyl | 4-(dimethylamino)phenylacetyl | " | 83 | 7.3 | 634.2 |
| 218 | 2-(pyridin-2-yl)ethyl | 4-cyclohexylbutanoyl | " | 87.32 | 7.9 | 566.3 |
| 219 | 2-(pyridin-2-yl)ethyl | 4-(dimethylamino)phenylacetyl | " | 79 | 5.7 | 575.2 |
| 220 | 2,6-difluorobenzyl | 4-cyclohexylbutanoyl | " | 89 | 10.7 | 587.2 |
| 221 | 2,6-difluorobenzyl | 4-(dimethylamino)phenylacetyl | " | 78.75 | 7.4 | 596.2 |
| 222 | 3,3-diphenylpropyl | 4-cyclohexylbutanoyl | " | 95 | 11.6 | 655.3 |

-continued

| Ex | R₁ | R₂ | R₃ | Purity (%) | rt | M + H+ |
|---|---|---|---|---|---|---|
| 223 | (3,3-diphenylpropyl) | 4-(dimethylamino)phenylacetyl | " | 79 | 8.6 | 664.3 |
| 224 | (indol-3-yl)methyl | 4-cyclohexylbutanoyl | 2-acetamido-4-methylthiazol-5-ylsulfonyl | 58 | 9.4 | 614.2 |
| 225 | (indol-3-yl)methyl | 4-(dimethylamino)phenylacetyl | " | 78 | 6.4 | 623.2 |
| 226 | 3,4-dimethoxyphenethyl | 4-cyclohexylbutanoyl | " | 75 | 9.2 | 635.3 |
| 227 | 3,4-dimethoxyphenethyl | 4-(dimethylamino)phenylacetyl | " | 88 | 6.1 | 644.3 |
| 228 | (pyridin-2-yl)ethyl | 4-cyclohexylbutanoyl | " | 86 | 6.7 | 576.3 |
| 229 | (pyridin-2-yl)ethyl | 4-(dimethylamino)phenylacetyl | " | 80 | 4.6 | 585.2 |
| 230 | 2,6-difluorobenzyl | 4-cyclohexylbutanoyl | " | 73 | 9.5 | 597.2 |
| 231 | 2,6-difluorobenzyl | 4-(dimethylamino)phenylacetyl | " | 66 | 6.2 | 606.2 |

-continued

| Ex | R₁ | R₂ | R₃ | Purity (%) | rt | M + H+ |
|---|---|---|---|---|---|---|
| 232 | *CH₂CH₂CH(Ph)₂ | cyclohexyl-(CH₂)₃-C(=O)-* | " | 62 | 10.5 | 665.3 |
| 233 | *CH₂CH₂CH(Ph)₂ | 4-(Me₂N)-C₆H₄-CH₂-C(=O)-* | " | 81 | 7.5 | 674.3 |
| 234 | *CH₂CH₂-(3-indolyl) | cyclohexyl-(CH₂)₃-C(=O)-* | 1-methylimidazol-4-yl-SO₂-* | 92 | 8.9 | 540.3 |
| 235 | *CH₂CH₂-(3-indolyl) | 4-(Me₂N)-C₆H₄-CH₂-C(=O)-* | " | 86 | 5.6 | 549.2 |
| 236 | *CH₂CH₂-(3,4-dimethoxyphenyl) | cyclohexyl-(CH₂)₃-C(=O)-* | " | 91 | 8.7 | 561.3 |
| 237 | *CH₂CH₂-(3,4-dimethoxyphenyl) | 4-(Me₂N)-C₆H₄-CH₂-C(=O)-* | " | 94.51 | 5.4 | 570.2 |
| 238 | *CH₂CH₂-(2-pyridyl) | cyclohexyl-(CH₂)₃-C(=O)-* | " | 93.36 | 6.2 | 502.3 |
| 239 | *CH₂CH₂-(2-pyridyl) | 4-(Me₂N)-C₆H₄-CH₂-C(=O)-* | " | 97 | 3.8 | 511.3 |

-continued
| Ex | R₁ | R₂ | R₃ | Purity (%) | rt | M + H+ |
|---|---|---|---|---|---|---|
| 240 | 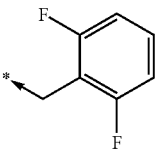 | 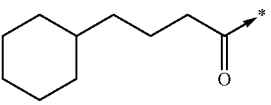 | " | 98.13 | 9.0 | 523.3 |
| 241 | 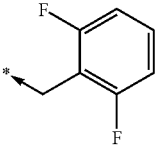 | 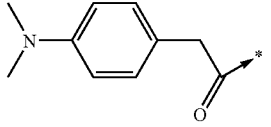 | " | 82 | 5.4 | 532.2 |
| 242 | 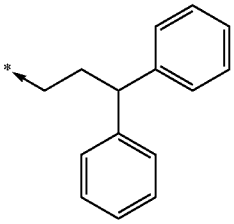 | 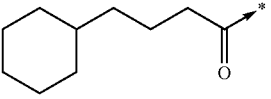 | " | 99 | 10.1 | 591.3 |
| 243 | 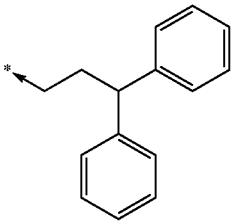 | 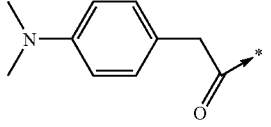 | " | 94.74 | 6.8 | 600.3 |
| 244 | 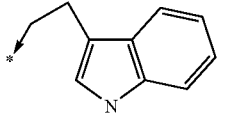 | 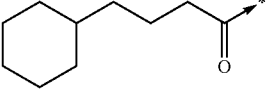 | 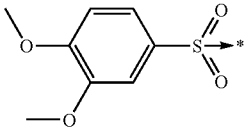 | 89 | 9.8 | 596.3 |
| 245 | 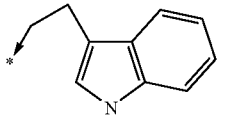 | 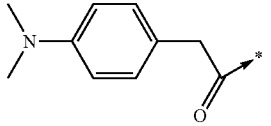 | " | 81 | 6.6 | 605.3 |
| 246 | 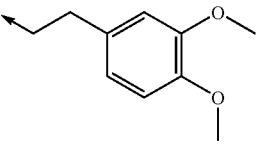 | 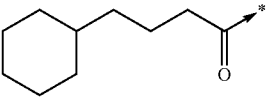 | " | 96 | 9.7 | 617.3 |
| 247 | 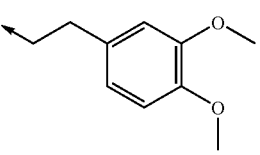 | 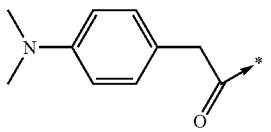 | " | 85.68 | 6.4 | 626.3 |
| 248 | 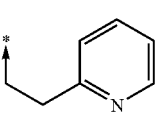 | 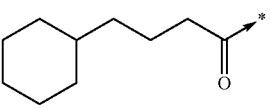 | " | 98.65 | 7.1 | 558.3 |

-continued

| Ex | R₁ | R₂ | R₃ | Purity (%) | rt | M + H+ |
|---|---|---|---|---|---|---|
| 249 | 2-pyridylethyl | 4-(dimethylamino)phenylacetyl | " | 92 | 4.8 | 567.2 |
| 250 | 2,6-difluorobenzyl | 4-cyclohexylbutanoyl | " | 96 | 10.0 | 579.2 |
| 251 | 2,6-difluorobenzyl | 4-(dimethylamino)phenylacetyl | " | 88.12 | 6.5 | 588.2 |
| 252 | 3,3-diphenylpropyl | 4-cyclohexylbutanoyl | " | 97 | 10.9 | 647.3 |
| 253 | 3,3-diphenylpropyl | 4-(dimethylamino)phenylacetyl | " | 86 | 7.8 | 656.3 |
| 254 | 3-indolylethyl | 4-cyclohexylbutanoyl | 2,6-difluorophenylsulfonyl | 79 | 10.1 | 572.2 |
| 255 | 3-indolylethyl | 4-(dimethylamino)phenylacetyl | " | 79 | 7.0 | 581.2 |
| 256 | 3,4-dimethoxyphenethyl | 4-cyclohexylbutanoyl | " | 71 | 10.0 | 593.3 |

-continued

| Ex | R₁ | R₂ | R₃ | Purity (%) | rt | M + H+ |
|---|---|---|---|---|---|---|
| 257 | 3,4-dimethoxyphenethyl | 4-(dimethylamino)phenylacetyl | " | 72.74 | 6.6 | 602.2 |
| 258 | 2-(pyridin-2-yl)ethyl | 4-cyclohexylbutanoyl | " | 79.1 | 7.4 | 534.3 |
| 259 | (pyridin-2-yl)methyl | 4-(dimethylamino)phenylacetyl | " | 74 | 4.9 | 543.2 |
| 260 | 2,6-difluorobenzyl | 4-cyclohexylbutanoyl | " | 84.17 | 10.3 | 555.2 |
| 261 | 2,6-difluorobenzyl | 4-(dimethylamino)phenylacetyl | " | 76.16 | 6.7 | 564.2 |
| 262 | 3,3-diphenylpropyl | 4-cyclohexylbutanoyl | " | 95 | 11.1 | 623.3 |
| 263 | 3,3-diphenylpropyl | 4-(dimethylamino)phenylacetyl | " | 78.91 | 8.0 | 632.3 |
| 264 | 2-(indol-3-yl)ethyl | 3,4-dichlorophenylacetyl | H | 75.26 | 5.1 | 430.2 |
| 265 | " | 3-(trifluoromethyl)phenylacetyl | " | 90.43 | 5.0 | 430.3 |

-continued
| Ex | R₁ | R₂ | R₃ | Purity (%) | rt | M + H+ |
|---|---|---|---|---|---|---|
| 266 | " | 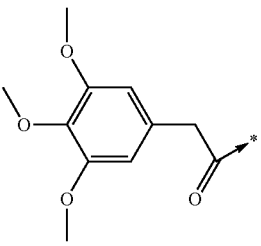 | " | 74.93 | 4.3 | 452.3 |
| 267 | " | 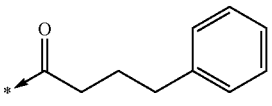 | " | 79.62 | 4.9 | 390.3 |
| 268 | " | 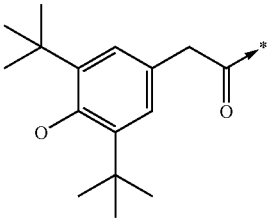 | " | 92.82 | 5.6 | 490.4 |
| 269 | " | 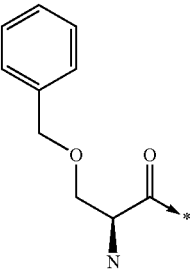 | " | 68.87 | 3.6 | 421.3 |
| 270 | " | 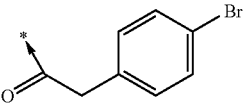 | " | 79.07 | 4.9 | 440.2 |
| 271 | " | 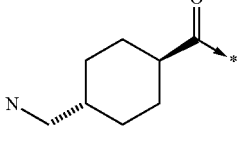 | " | 84.22 | 3.0 | 392.3 |
| 272 | " | 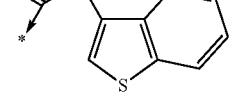 | " | 67.34 | 4.9 | 418.2 |
| 273 | " | 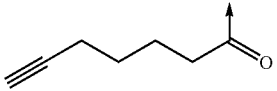 | " | 81.63 | 4.4 | 352.3 |

-continued

| Ex | R₁ | R₂ | R₃ | Purity (%) | rt | M + H+ |
|---|---|---|---|---|---|---|
| 274 | " | (4-methylpentanoyl) | " | 90.11 | 4.7 | 342.3 |
| 275 | " | (2,4,6-trimethoxybenzoyl) | " | 54.36 | 4.3 | 438.3 |
| 276 | " | (4-trifluoromethoxybenzoyl) | " | 81.69 | 4.9 | 432.2 |
| 277 | " | (3-cyclohexylpropanoyl) | " | 85.62 | 5.2 | 382.3 |
| 278 | " | (4-aminophenylacetyl) | " | 86.19 | 3.2 | 377.3 |
| 279 | (3,4-dimethoxyphenethyl) | (3,4-dichlorophenylacetyl) | " | 94.76 | 4.9 | 451.2 |
| 280 | " | (3-trifluoromethylphenylacetyl) | " | 99.42 | 4.7 | 451.3 |
| 281 | " | (3,4,5-trimethoxyphenylacetyl) | " | 90.55 | 4.0 | 473.3 |
| 282 | " | (4-phenylbutanoyl) | " | 93.80 | 4.6 | 411.3 |

-continued

| Ex | R₁ | R₂ | R₃ | Purity (%) | rt | M + H+ |
|---|---|---|---|---|---|---|
| 283 | " | 3,5-di-tert-butyl-4-hydroxyphenylacetyl | " | 82.71 | 5.4 | 511.4 |
| 284 | " | O-benzyl-serinyl | " | 90.85 | 3.4 | 442.3 |
| 285 | " | 4-bromophenylacetyl | " | 98.65 | 4.6 | 461.2 |
| 286 | " | trans-4-(aminomethyl)cyclohexanecarbonyl | " | 98.80 | 2.8 | 404.3 |
| 287 | " | benzothiophen-3-yl-acetyl | " | 86.02 | 4.6 | 439.3 |
| 288 | " | hept-6-ynoyl | " | 97.47 | 4.1 | 373.3 |
| 289 | " | 4-methylpentanoyl | " | 99.31 | 4.4 | 363.3 |
| 290 | " | 2,4,6-trimethoxybenzoyl | " | 45.77 | 4.1 | 459.3 |

-continued
| Ex | R₁ | R₂ | R₃ | Purity (%) | rt | M + H+ |
|---|---|---|---|---|---|---|
| 291 | " | 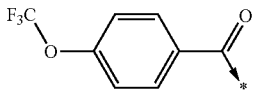 | " | 94.07 | 4.6 | 453.3 |
| 292 | " | 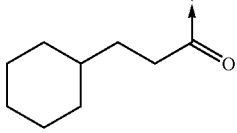 | " | 95.65 | 5.0 | 403.4 |
| 293 | " | 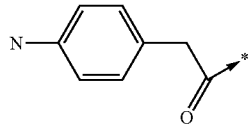 | " | 94.30 | 2.9 | 398.3 |
| 294 | 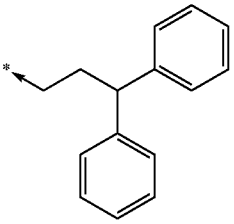 | 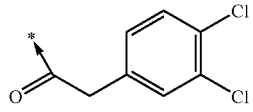 | " | 80.64 | 5.9 | 481.2 |
| 295 | " | 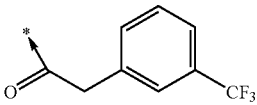 | " | 98.05 | 5.7 | 481.3 |
| 296 | " | 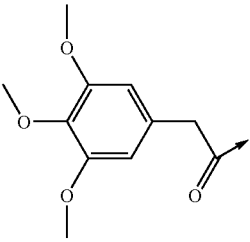 | " | 94.93 | 5.0 | 503.4 |
| 297 | " | 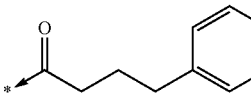 | " | 96.81 | 5.6 | 441.3 |
| 298 | " | 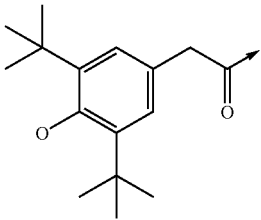 | " | 95.00 | 6.3 | 541.4 |

-continued

| Ex | R₁ | R₂ | R₃ | Purity (%) | rt | M + H+ |
|---|---|---|---|---|---|---|
| 299 | " | (O-benzyl serine group) | " | 95.13 | 4.2 | 472.4 |
| 300 | " | (arginine group) | " | 52.68 | 3.2 | 452.4 |
| 301 | " | (4-bromophenylacetyl group) | " | 98.03 | 5.6 | 491.2 |
| 302 | " | (4-(aminomethyl)cyclohexanecarbonyl group) | " | 96.44 | 3.7 | 217.9 |
| 303 | " | (benzothiophen-3-ylacetyl group) | " | 97.22 | 5.6 | 469.3 |
| 304 | " | (hept-6-ynoyl group) | " | 96.97 | 5.2 | 403.3 |
| 305 | " | (4-methylpentanoyl group) | " | 99.05 | 5.4 | 393.4 |
| 306 | " | (2,4,6-trimethoxybenzoyl group) | " | 32.67 | 5.1 | 489.3 |

-continued
| Ex | R₁ | R₂ | R₃ | Purity (%) | rt | M + H+ |
|---|---|---|---|---|---|---|
| 307 | " | 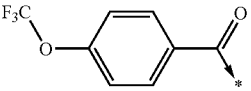 | " | 84.51 | 5.6 | 483.3 |
| 308 | " | 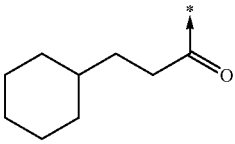 | " | 98.44 | 6.0 | 433.4 |
| 309 | " | 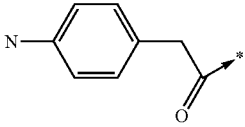 | " | 97.78 | 4.0 | 428.3 |
| 310 | 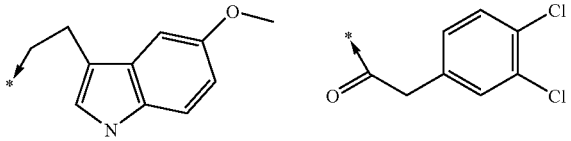 | 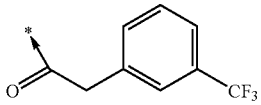 | " | 79.54 | 5.0 | 460.2 |
| 311 | " | 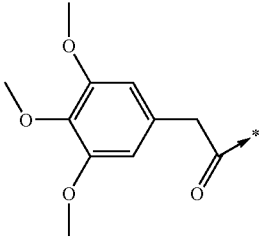 | " | 78.59 | 4.9 | 460.3 |
| 312 | " | 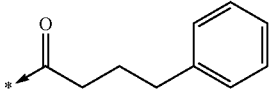 | " | 66.24 | 4.2 | 482.3 |
| 313 | " | 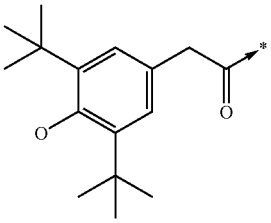 | " | 70.15 | 4.8 | 420.3 |
| 314 | " |  | " | 57.87 | 5.5 | 520.4 |

-continued

| Ex | R₁ | R₂ | R₃ | Purity (%) | rt | M + H+ |
|---|---|---|---|---|---|---|
| 315 | " | (benzyloxymethyl serine derivative) | " | 71.26 | 3.6 | 451.3 |
| 316 | " | (4-bromophenylacetyl) | " | 81.16 | 4.8 | 470.2 |
| 317 | " | (4-aminomethylcyclohexanecarbonyl) | " | 74.96 | 2.9 | 413.3 |
| 318 | " | (benzothiophen-3-ylacetyl) | " | 53.47 | 4.8 | 448.3 |
| 319 | " | (hept-6-ynoyl) | " | 87.88 | 4.3 | 382.3 |
| 320 | " | (4-methylpentanoyl) | " | 91.41 | 4.6 | 372.3 |
| 321 | " | (2,4,6-trimethoxybenzoyl) | " | 1.59 | 5.0 | 468.3 |
| 322 | " | (4-trifluoromethoxybenzoyl) | " | 77.81 | 4.8 | 462.3 |
| 323 | " | (3-cyclohexylpropanoyl) | " | 76.59 | 5.1 | 412.3 |

-continued

| Ex | R₁ | R₂ | R₃ | Purity (%) | rt | M + H+ |
|---|---|---|---|---|---|---|
| 324 | " | 4-aminophenyl-CH₂-C(=O)-* | " | 83.35 | 3.1 | 407.3 |
| 325 | 3-indolyl-CH₂-CH₂-* | 3,4-dichlorophenyl-CH₂-C(=O)-* | CH₃-* | 87.42 | 5.2 | 444.2 |
| 326 | " | 3-(CF₃)phenyl-CH₂-C(=O)-* | " | 98.89 | 5.1 | 444.3 |
| 327 | " | 3,4,5-trimethoxyphenyl-CH₂-C(=O)-* | " | 95.68 | 4.3 | 466.3 |
| 328 | " | phenyl-(CH₂)₃-C(=O)-* | " | 97.27 | 4.9 | 404.3 |
| 329 | " | 3,5-di-tert-butyl-4-hydroxyphenyl-CH₂-C(=O)-* | " | 95.73 | 5.7 | 504.4 |
| 330 | " | O-benzyl-serinyl-* | " | 83.37 | 3.7 | 435.3 |

-continued

| Ex | R₁ | R₂ | R₃ | Purity (%) | rt | M + H+ |
|---|---|---|---|---|---|---|
| 331 | " | (S)-2-amino-5-guanidinopentanoyl | " | 71.88 | 3.2 | 413.3 |
| 332 | " | 2-(4-bromophenyl)acetyl | " | 98.33 | 5.0 | 454.2 |
| 333 | " | trans-4-(aminomethyl)cyclohexanecarbonyl | " | 83.73 | 3.0 | 397.3 |
| 334 | " | 2-(benzo[b]thiophen-3-yl)acetyl | " | 94.77 | 5.0 | 432.3 |
| 335 | " | hept-6-ynoyl | " | 95.88 | 4.5 | 366.3 |
| 336 | " | 4-methylpentanoyl | " | 98.9 | 4.7 | 356.3 |
| 337 | " | 2,4,6-trimethoxybenzoyl | " | 50.74 | 4.4 | 452.3 |
| 338 | " | 4-(trifluoromethoxy)benzoyl | " | 95.39 | 5.0 | 446.3 |
| 339 | " | 3-cyclohexylpropanoyl | " | 98.2 | 5.3 | 396.3 |

-continued

| Ex | R₁ | R₂ | R₃ | Purity (%) | rt | M + H+ |
|---|---|---|---|---|---|---|
| 340 | " | 4-aminophenyl-CH₂-C(=O)-* | " | 92.35 | 3.2 | 391.3 |
| 341 | 1-methylindol-3-yl-CH₂CH₂-* | 3,4-dichlorophenyl-CH₂-C(=O)-* | H-* | 90.41 | 5.1 | 444.2 |
| 342 | " | 3-(CF₃)phenyl-CH₂-C(=O)-* | " | 87.41 | 5.0 | 444.3 |
| 343 | " | 3,4,5-trimethoxyphenyl-CH₂-C(=O)-* | " | 87.37 | 4.3 | 466.3 |
| 344 | " | Ph-CH₂CH₂CH₂-C(=O)-* | " | 83.01 | 4.9 | 404.3 |
| 345 | " | 3,5-di-tert-butyl-4-hydroxyphenyl-CH₂-C(=O)-* | " | 89.47 | 5.6 | 504.4 |
| 346 | " | O-benzyl-serinyl-* | " | 77.55 | 3.6 | 435.3 |

-continued
| Ex | R₁ | R₂ | R₃ | Purity (%) | rt | M + H+ |
|---|---|---|---|---|---|---|
| 347 | " | 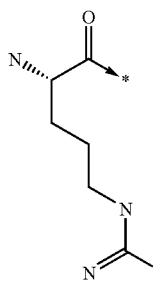 | " | 49.49 | 2.4 | 414.3 |
| 348 | " | 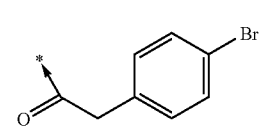 | " | 85.63 | 4.9 | 454.2 |
| 349 | " | 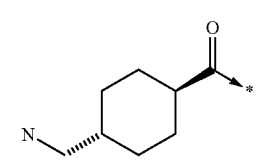 | " | 88.12 | 2.9 | 397.3 |
| 350 | " | 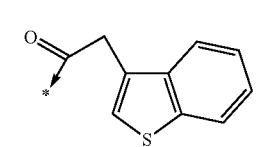 | " | 87.73 | 4.9 | 432.3 |
| 351 | " | 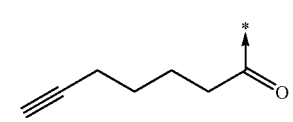 | " | 84.48 | 4.4 | 366.3 |
| 352 | " | 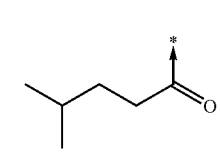 | " | 82.03 | 4.7 | 356.3 |
| 353 | " | 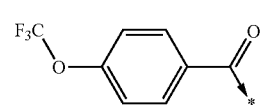 | " | 82.93 | 4.9 | 446.3 |
| 354 | " | 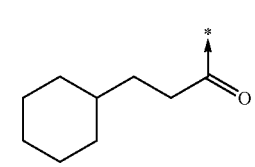 | " | 72.6 | 5.3 | 396.3 |
| 355 | " | 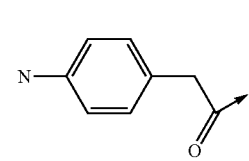 | " | 86.75 | 3.2 | 391.3 |

-continued
| Ex | R₁ | R₂ | R₃ | Purity (%) | rt | M + H+ |
|---|---|---|---|---|---|---|
| 356 | 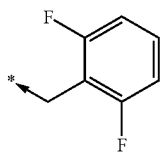 | 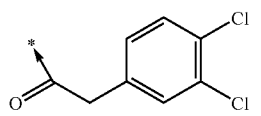 | " | 93.75 | 4.7 | 413.1 |
| 357 | " | 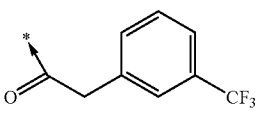 | " | 96.13 | 4.6 | 413.2 |
| 358 | " | 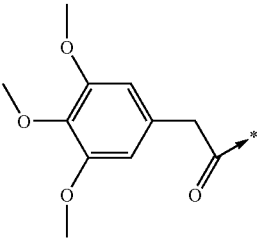 | " | 98.3 | 3.8 | 435.2 |
| 359 | " | 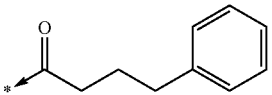 | " | 96.45 | 4.5 | 373.2 |
| 360 | " | 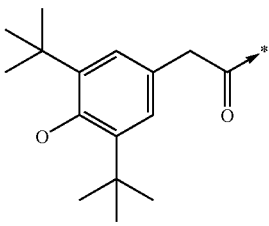 | " | 97.9 | 5.3 | 473.4 |
| 361 | " | 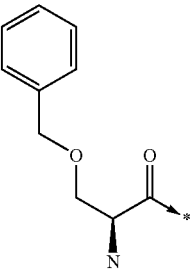 | " | 97.57 | 3.0 | 404.3 |
| 362 | " | 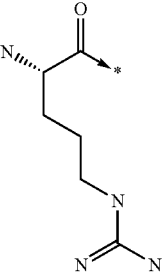 | " | 78.0 | 2.5 | 383.2 |

-continued
| Ex | R₁ | R₂ | R₃ | Purity (%) | rt | M + H+ |
|---|---|---|---|---|---|---|
| 363 | " | 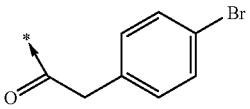 | " | 98.96 | 4.5 | 423.1 |
| 364 | " | 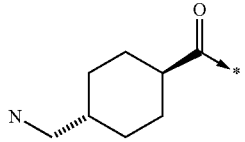 | " | 93.98 | 2.4 | 366.3 |
| 365 | " | 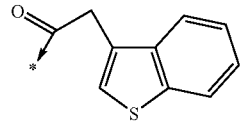 | " | 97.98 | 4.5 | 401.2 |
| 366 | " | 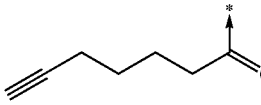 | " | 93.33 | 4.0 | 335.2 |
| 367 | " | 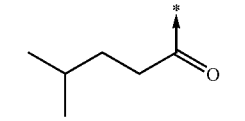 | " | 95.73 | 4.3 | 325.3 |
| 368 | " | 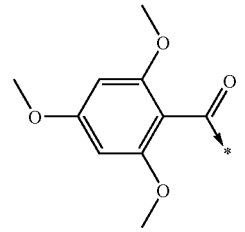 | " | 1.21 | 3.9 | 421.3 |
| 369 | " | 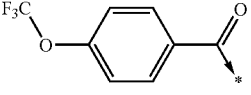 | " | 88.55 | 4.6 | 415.2 |
| 370 | " | 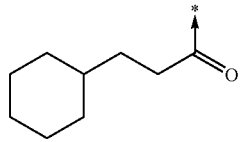 | " | 95.93 | 4.9 | 365.3 |
| 371 | " | 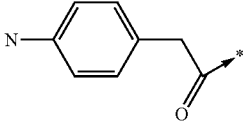 | " | 99.1 | 2.6 | 360.2 |
| 372 | 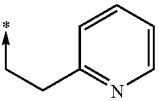 | 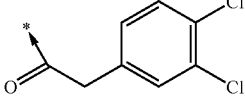 | " | 90.59 | 3.4 | 392.1 |

-continued
| Ex | R₁ | R₂ | R₃ | Purity (%) | rt | M + H+ |
|---|---|---|---|---|---|---|
| 373 | " | 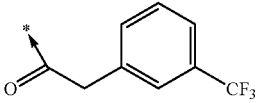 | " | 93.57 | 3.3 | 392.2 |
| 374 | " | 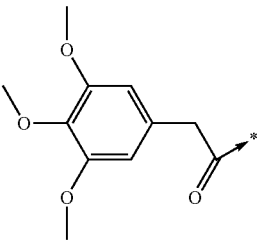 | " | 97.23 | 2.6 | 414.2 |
| 375 | " | 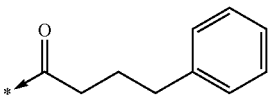 | " | 93.83 | 3.1 | 352.3 |
| 376 | " | 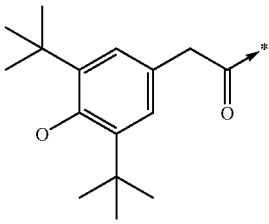 | " | 96.81 | 4.0 | 452.4 |
| 377 | " | 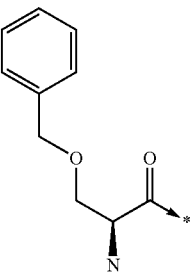 | " | 97.7 | 2.2 | 383.3 |
| 378 | " | 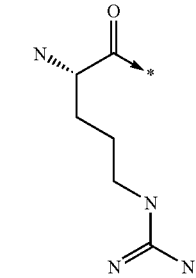 | " | 53.69 | 2.3 | 362.2 |
| 379 | " | 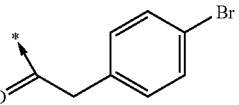 | " | 97.1 | 3.1 | 402.1 |

-continued
| Ex | R₁ | R₂ | R₃ | Purity (%) | rt | M + H+ |
|---|---|---|---|---|---|---|
| 380 | " | 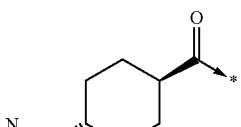 | " | 70.3 | 2.5 | 345.3 |
| 381 | " | 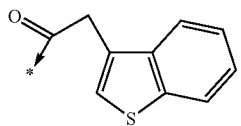 | " | 97.59 | 3.1 | 380.2 |
| 382 | " | 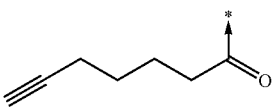 | " | 86.74 | 2.4 | 314.2 |
| 383 | " | 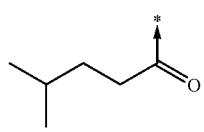 | " | 87.28 | 2.6 | 304.3 |
| 384 | " | 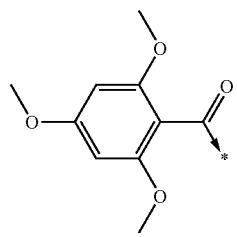 | " | 10.27 | 3.1 | 400.2 |
| 385 | " | 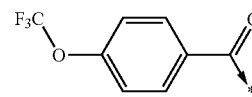 | " | 93.38 | 3.1 | 394.2 |
| 386 | " | 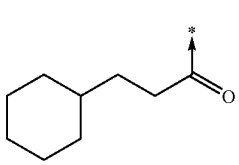 | " | 88.99 | 3.4 | 344.3 |
| 387 | " | 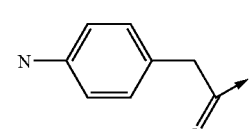 | " | 89.43 | 2.5 | 339.3 |
| 388 | 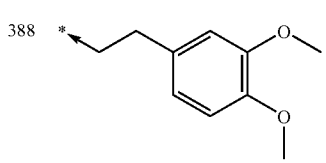 | 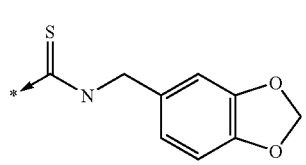 |  | 86.18 | 4.2 | 458.3 |
| 389 | " | 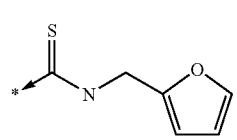 | " | 37.01 | 3.9 | 404.3 |

-continued
| Ex | R₁ | R₂ | R₃ | Purity (%) | rt | M + H+ |
|---|---|---|---|---|---|---|
| 390 | " | 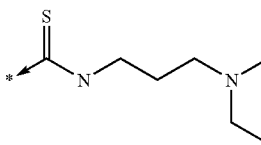 | " | 57.02 | 2.7 | 437.4 |
| 391 | " | 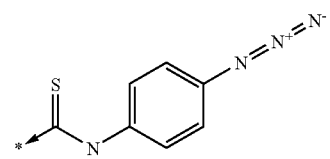 | " | 78.70 | 4.3 | 441.3 |
| 392 | " | 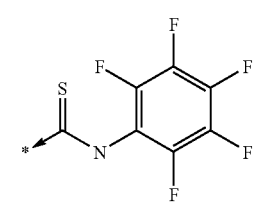 | " | 67.94 | 4.6 | 490.3 |
| 393 | " | 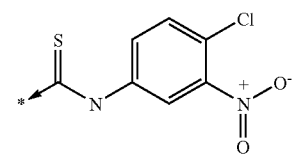 | " | 39.75 | 4.5 | 479.3 |
| 394 | " | 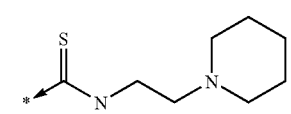 | " | 94.48 | 2.8 | 435.4 |
| 395 | " | 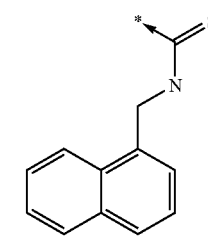 | " | 83.7 | 3.4 | 432.3 |
| 396 | " | 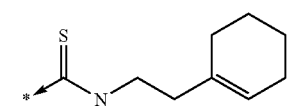 | " | 96.5 | 4.7 | 464.4 |
| 397 | " | 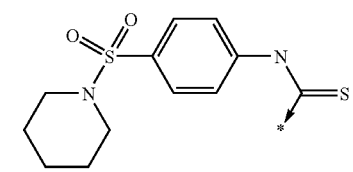 | " | 43.75 | 4.5 | 547.3 |
| 398 | 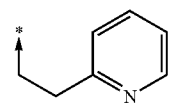 | 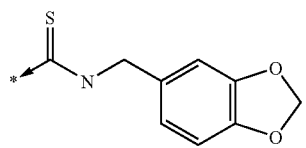 | " | 86.87 | 3.3 | 399.3 |

-continued
| Ex | R₁ | R₂ | R₃ | Purity (%) | rt | M + H+ |
|---|---|---|---|---|---|---|
| 399 | " | 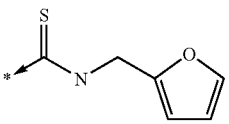 | " | 47.77 | 2.9 | 345.3 |
| 400 | " | 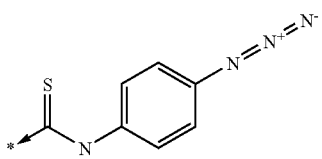 | " | 82 | 3.4 | 382.3 |
| 401 | " | 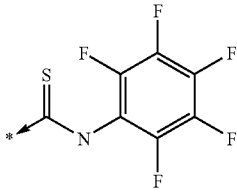 | " | 97.10 | 3.8 | 431.2 |
| 402 | " | 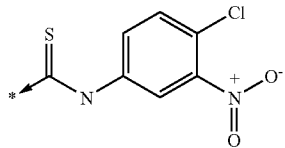 | " | 76.92 | 3.8 | 420.2 |
| 403 | " | 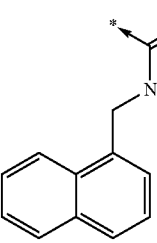 | " | 97.3 | 2.8 | 373.3 |
| 404 | " | 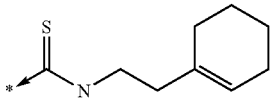 | " | 95.9 | 4.0 | 405.3 |
| 405 | " | 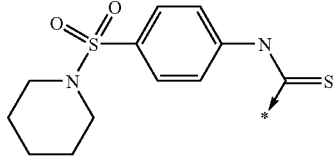 | " | 69.50 | 3.7 | 488.3 |
| 406 | 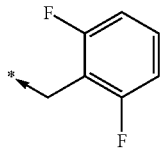 | 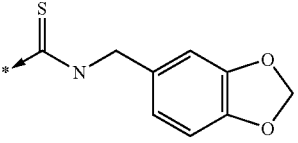 | " | 90.79 | 4.1 | 420.3 |
| 407 | " | 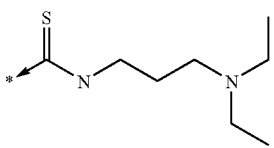 | " | 86.38 | 2.5 | 399.3 |

-continued

| Ex | R₁ | R₂ | R₃ | Purity (%) | rt | M + H+ |
|---|---|---|---|---|---|---|
| 408 | " | 2,3,4,5,6-pentafluorophenyl thioamide | " | 67.52 | 4.6 | 452.2 |
| 409 | " | N-(2-piperidin-1-ylethyl) thioamide | " | 99.8 | 2.7 | 397.3 |
| 410 | " | N-(naphthalen-1-ylmethyl) thioamide | " | 97.7 | 3.3 | 394.3 |
| 411 | 3,3-diphenylpropyl | N-(benzo[d][1,3]dioxol-5-ylmethyl) thioamide | " | 87.97 | 5.0 | 488.3 |
| 412 | " | N-(3-(diethylamino)propyl) thioamide | " | 97.23 | 3.6 | 467.4 |
| 413 | " | N-(2-piperidin-1-ylethyl) thioamide | " | 99.29 | 3.7 | 465.4 |
| 414 | " | N-(naphthalen-1-ylmethyl) thioamide | " | 96.2 | 4.2 | 462.4 |
| 415 | " | N-(2-(cyclohex-1-enyl)ethyl) thioamide | " | 72.0 | 5.5 | 494.3 |

-continued

| Ex | R₁ | R₂ | R₃ | Purity (%) | rt | M + H+ |
|---|---|---|---|---|---|---|
| 416 | 5-methoxy-tryptamine linker | *-C(S)-NH-CH₂-(benzo[1,3]dioxol-5-yl) | " | 85.09 | 4.3 | 467.3 |
| 417 | " | *-C(S)-NH-CH₂-(2-furyl) | " | 68.52 | 4.1 | 413.3 |
| 418 | " | *-C(S)-NH-CH₂CH₂CH₂-N(Et)₂ | " | 98.76 | 2.8 | 446.4 |
| 419 | " | *-C(S)-NH-(4-azidophenyl) | " | 73.21 | 4.4 | 450.3 |
| 420 | " | *-C(S)-NH-(pentafluorophenyl) | " | 76.94 | 4.7 | 499.2 |
| 421 | " | *-C(S)-NH-(4-chloro-3-nitrophenyl) | " | 85.12 | 4.6 | 488.2 |
| 422 | " | *-C(S)-NH-CH₂CH₂-(1-piperidinyl) | " | 98.15 | 2.9 | 444.4 |
| 423 | " | *-C(S)-NH-CH₂-(1-naphthyl) | " | 58 | 5.1 | 477.3 |
| 424 | " | *-C(S)-NH-CH₂CH₂-(cyclohex-1-en-1-yl) | " | 25 | 3.6 | 410.3 |

-continued
| Ex | R₁ | R₂ | R₃ | Purity (%) | rt | M + H+ |
|---|---|---|---|---|---|---|
| 425 | " | 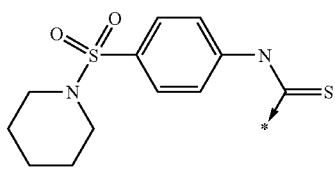 | " | 69.90 | 4.6 | 556.3 |
| 426 | 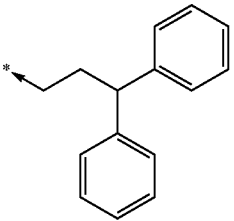 | 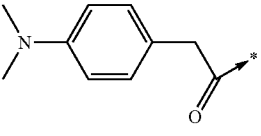 | 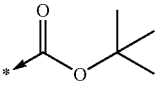 | 90.11 | 8.2 | 556.3 |
| 427 | " | 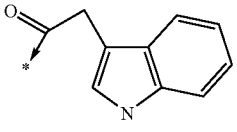 | " | 95.30 | 9.7 | 552.3 |
| 428 | " | 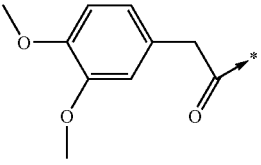 | " | 89.35 | 9.6 | 573.3 |
| 429 | " | 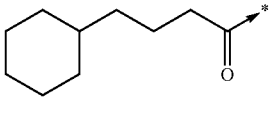 | " | 97.48 | 11.8 | 547.4 |
| 430 | " | 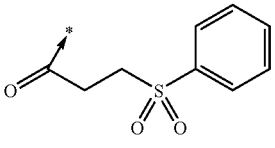 | " | 91.35 | 9.6 | 591.3 |
| 431 | " | 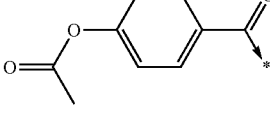 | " | 66.60 | 9.7 | 557.3 |
| 432 | " |  | " | 97.25 | 10.5 | 547.3 |
| 433 | " | 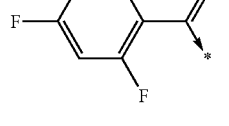 | " | 98.20 | 10.2 | 549.3 |

-continued

| Ex | R₁ | R₂ | R₃ | Purity (%) | rt | M + H+ |
|---|---|---|---|---|---|---|
| 434 | *-CH₂CH₂CH₂-N(morpholine) | 4-(dimethylamino)phenyl-CH₂-C(=O)-* | " | 88.28 | 4.7 | 489.3 |
| 435 | " | indol-3-yl-CH₂-C(=O)-* | " | 94.30 | 5.8 | 485.3 |
| 436 | " | 3,4-dimethoxyphenyl-CH₂-C(=O)-* | " | 92.92 | 5.6 | 506.3 |
| 437 | " | cyclohexyl-(CH₂)₃-C(=O)-* | " | 95.73 | 7.1 | 480.4 |
| 438 | " | *-(C=O)-CH₂CH₂-S(=O)₂-phenyl | " | 89.80 | 5.6 | 524.3 |
| 439 | " | 4-(acetyloxy)phenyl-C(=O)-* | " | 69.38 | 5.6 | 490.3 |
| 440 | " | thien-2-yl-(CH₂)₃-C(=O)-* | " | 95.21 | 6.2 | 480.3 |
| 441 | " | 2,4-difluorophenyl-C(=O)-* | " | 96.98 | 6.0 | 482.3 |
| 442 | *-CH₂CH₂-CH(phenyl)₂ | 4-(dimethylamino)phenyl-CH₂-C(=O)-* | H-* | 85.00 | 5.4 | 456.3 |
| 443 | " | indol-3-yl-CH₂-C(=O)-* | " | 94.40 | 6.5 | 452.3 |

-continued

| Ex | R₁ | R₂ | R₃ | Purity (%) | rt | M + H+ |
|---|---|---|---|---|---|---|
| 444 | " | 3,4-dimethoxyphenylacetyl | " | 91.10 | 6.3 | 473.3 |
| 445 | " | 4-cyclohexylbutanoyl | " | 96.60 | 7.7 | 447.3 |
| 446 | " | 3-(phenylsulfonyl)propanoyl | " | 92.80 | 6.3 | 491.2 |
| 447 | " | 4-acetoxybenzoyl | " | 85.40 | 6.3 | 457.2 |
| 448 | " | 4-(thiophen-2-yl)butanoyl | " | 96.70 | 6.9 | 447.2 |
| 449 | " | 2,4-difluorobenzoyl | " | 98 | 6.7 | 449.2 |
| 450 | 3-morpholinopropyl | indol-3-ylacetyl | " | 38.17 | 3.6 | 385.2 |
| 451 | " | 3,4-dimethoxyphenylacetyl | " | 92.70 | 3.4 | 406.2 |
| 452 | " | 4-cyclohexylbutanoyl | " | 89.50 | 4.7 | 380.3 |
| 453 | " | 3-(phenylsulfonyl)propanoyl | " | 86.24 | 3.4 | 424.2 |

-continued
| Ex | R₁ | R₂ | R₃ | Purity (%) | rt | M + H+ |
|---|---|---|---|---|---|---|
| 454 | " | 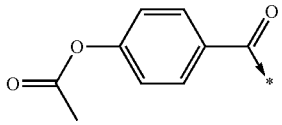 | " | 71.20 | 3.3 | 390.2 |
| 455 | " | 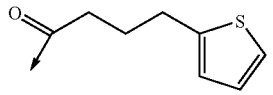 | " | 88.60 | 3.8 | 380.2 |
| 456 | " | 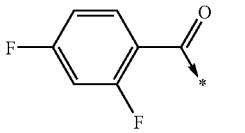 | " | 89.26 | 3.5 | 382.2 |
| 457 | 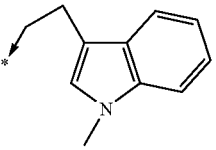 | 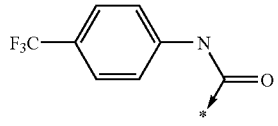 | " | 96.55 | 4.9 | 445.3 |
| 458 | " | 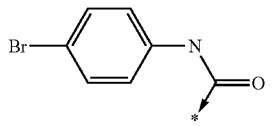 | " | 94.46 | 4.8 | 455.2 |
| 459 | " | 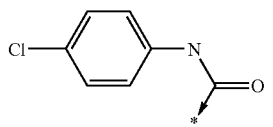 | " | 95.6 | 4.7 | 411.3 |
| 460 | " | 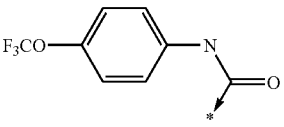 | " | 98.1 | 5.0 | 461.3 |
| 461 | " | 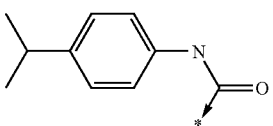 | " | 93.31 | 5.1 | 419.4 |
| 462 | " | 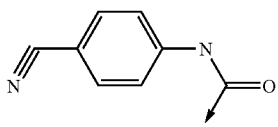 | " | 97.08 | 4.2 | 402.3 |
| 463 | " | 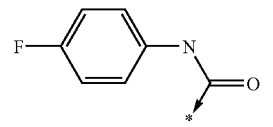 | " | 94.61 | 4.4 | 395.3 |

-continued

| Ex | R₁ | R₂ | R₃ | Purity (%) | rt | M + H+ |
|---|---|---|---|---|---|---|
| 464 | " | 4-iodophenyl-NHC(O)- | " | 97.05 | 4.9 | 503.2 |
| 465 | " | 4-biphenyl-NHC(O)- | " | 95.13 | 5.1 | 453.4 |
| 466 | 2-(5-methoxy-1-methyl-1H-indol-3-yl)ethyl | 4-(trifluoromethyl)phenyl-NHC(O)- | " | 93.21 | 4.8 | 475.3 |
| 467 | " | 4-bromophenyl-NHC(O)- | " | 94.08 | 4.7 | 485.2 |
| 468 | " | 4-chlorophenyl-NHC(O)- | " | 93.08 | 4.6 | 441.3 |
| 469 | " | 4-(trifluoromethoxy)phenyl-NHC(O)- | " | 95.17 | 4.9 | 491.3 |
| 470 | " | 4-isopropylphenyl-NHC(O)- | " | 89.99 | 5.0 | 449.4 |
| 471 | " | 4-cyanophenyl-NHC(O)- | " | 92 | 4.1 | 432.3 |
| 472 | " | 4-fluorophenyl-NHC(O)- | " | 94.71 | 4.3 | 425.3 |
| 473 | " | 4-iodophenyl-NHC(O)- | " | 95.3 | 4.8 | 533.2 |

-continued
| Ex | R₁ | R₂ | R₃ | Purity (%) | rt | M + H+ |
|---|---|---|---|---|---|---|
| 474 | " | 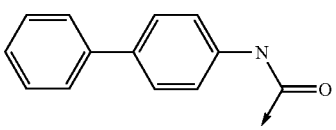 | " | 94.13 | 5.0 | 483.4 |
| 475 | 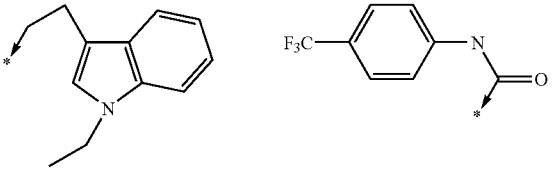 | 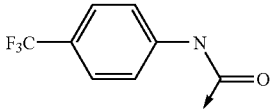 | " | 95 | 5.1 | 459.3 |
| 476 | " | 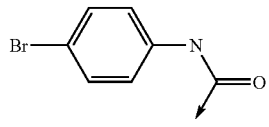 | " | 94.69 | 5.0 | 469.2 |
| 477 | " | 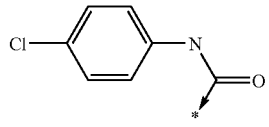 | " | 94.44 | 4.9 | 425.3 |
| 478 | " | 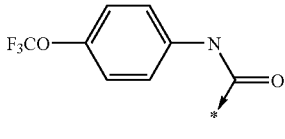 | " | 98 | 5.2 | 475.3 |
| 479 | " | 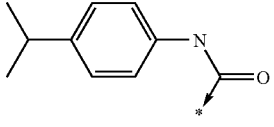 | " | 96.2 | 5.3 | 433.4 |
| 480 | " | 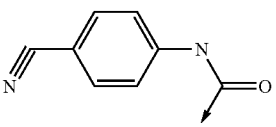 | " | 93 | 4.4 | 416.3 |
| 481 | " | 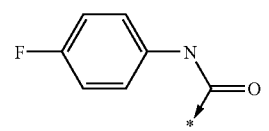 | " | 94.59 | 4.6 | 409.3 |
| 482 | " | 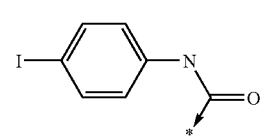 | " | 95.22 | 5.1 | 517.2 |
| 483 | " | 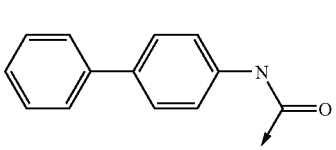 | " | 95.7 | 5.3 | 467.4 |

-continued
| Ex | R₁ | R₂ | R₃ | Purity (%) | rt | M + H+ |
|---|---|---|---|---|---|---|
| 484 | 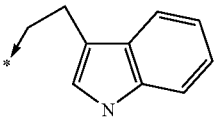 | 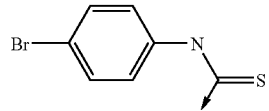 | " | 94.8 | 4.6 | 457.2 |
| 485 | " | 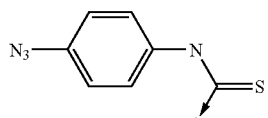 | " | 86.7 | 4.5 | 420.3 |
| 486 | " | 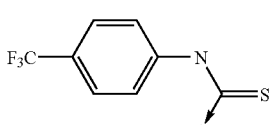 | " | 88.5 | 4.8 | 447.3 |
| 487 | " | 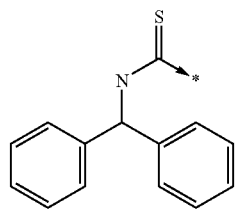 | " | 96.9 | 5.1 | 483.4 |
| 488 | " | 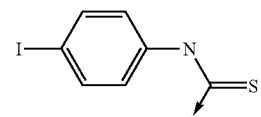 | " | 92.3 | 4.7 | 505.2 |
| 489 | 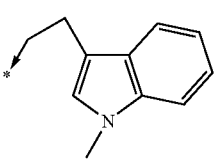 | 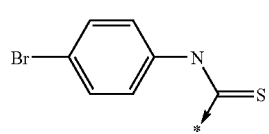 | " | 65.4 | 4.9 | 471.2 |
| 490 | " | 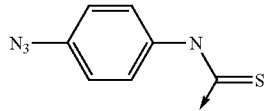 | " | 62.6 | 4.7 | 434.3 |
| 491 | " | 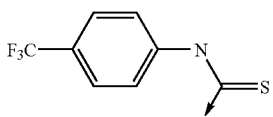 | " | 57.9 | 5.0 | 461.3 |
| 492 | " | 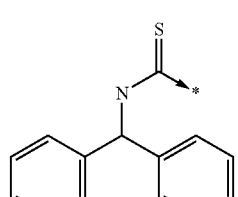 | " | 94.2 | 5.3 | 497.4 |

-continued
| Ex | R₁ | R₂ | R₃ | Purity (%) | rt | M + H+ |
|---|---|---|---|---|---|---|
| 493 | " | 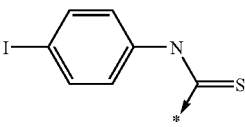 | " | 54.0 | 5.0 | 519.2 |
| 494 | 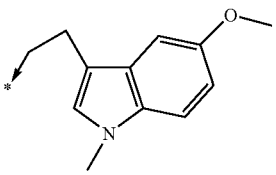 | 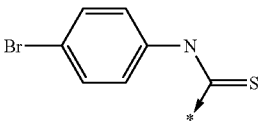 | " | 54.6 | 4.8 | 501.3 |
| 495 | " | 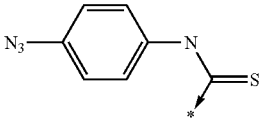 | " | 64.9 | 4.7 | 464.3 |
| 496 | " | 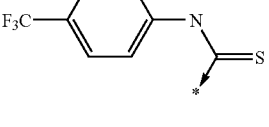 | " | 70.4 | 4.9 | 491.3 |
| 497 | " | 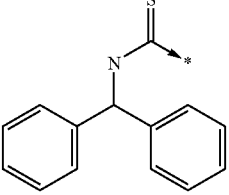 | " | 96.5 | 5.2 | 527.4 |
| 498 | " | 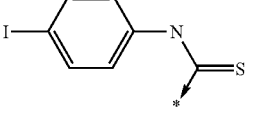 | " | 55.7 | 4.9 | 549.2 |
| 499 | 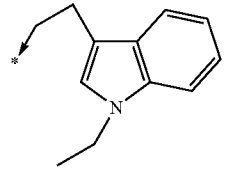 | 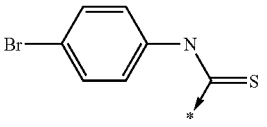 | " | 57.4 | 5.1 | 485.3 |
| 500 | " | 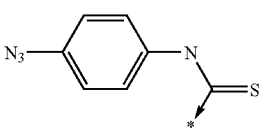 | " | 59.3 | 4.9 | 448.4 |
| 501 | " | 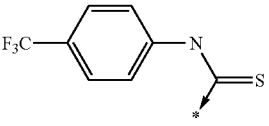 | " | 53.6 | 5.2 | 475.3 |

-continued

| Ex | R₁ | R₂ | R₃ | Purity (%) | rt | M + H+ |
|---|---|---|---|---|---|---|
| 502 | " | N-C(=S)-CH(Ph)(Ph) | " | 97.8 | 5.4 | 511.4 |
| 503 | " | 4-iodophenyl-NH-C(=S)-* | " | 10 +36.87 | 5.2 | 533.2 |
| 504 | *-CH2CH2-CH(Ph)(Ph) | cyclohexyl-(CH2)3-C(=O)-* | 4-bromophenyl-NH-C(=O)-* | 96.33 | 11.2 | 646.3 |
| 505 | " | *-C(=O)-CH2CH2-S(=O)2-Ph | " | 92.67 | 9.4 | 690.1 |
| 506 | " | 4-(acetyloxy)phenyl-C(=O)-* | " | 41.11 | 9.5 | 656.2 |
| 507 | " | *-C(=O)-(CH2)3-(2-thienyl) | " | 97.65 | 10.1 | 646.2 |
| 508 | " | 2,4-difluorophenyl-C(=O)-* | " | 96.29 | 9.9 | 648.2 |
| 509 | 3-indolyl-CH2CH2-* | 3-indolyl-CH2-C(=O)-* | *-O-C(=O)-O-tBu | 90.89 | 8.5 | 501.3 |
| 510 | " | " | H-* | 61.04 | 5.8 | 401.2 |
| 511 | " | cyclohexyl-(CH2)3-C(=O)-* | *-O-C(=O)-O-tBu | 99.16 | 10.5 | 496.4 |
| 512 | " | " | H-* | 95.73 | 7.1 | 396.3 |

-continued

| Ex | R₁ | R₂ | R₃ | Purity (%) | rt | M + H+ |
|---|---|---|---|---|---|---|
| 513 | " | 4-(thiophen-2-yl)butanoyl | tert-butoxycarbonyl | 66 | 9.3 | 496.3 |
| 514 | " | " | H | 95.00 | 8.9 | 396.2 |
| 515 | " | 2-(4-(trifluoromethyl)phenyl)acetyl | tert-butoxycarbonyl | 96.61 | 9.5 | 530.3 |
| 516 | " | " | H | 94.05 | 6.4 | 430.3 |
| 517 | " | 3-(3,4-dimethoxyphenyl)propanoyl | tert-butoxycarbonyl | 87 | 8.6 | 536.3 |
| 518 | " | " | H | 91.59 | 5.6 | 436.3 |
| 519 | 2-(3,4-dimethoxyphenyl)ethyl | 2-(1H-indol-3-yl)acetyl | tert-butoxycarbonyl | 86.84 | 8.4 | 522.3 |
| 520 | " | " | H | 94.18 | 5.4 | 422.3 |
| 521 | " | 4-cyclohexylbutanoyl | tert-butoxycarbonyl | 99.75 | 10.4 | 517.4 |
| 522 | " | " | H | 96.8 | 6.8 | 417.4 |
| 523 | " | 4-(thiophen-2-yl)butanoyl | tert-butoxycarbonyl | 70.34 | 9.1 | 517.3 |
| 524 | " | " | H | 93.49 | 5.8 | 417.3 |
| 525 | " | 2-(4-(trifluoromethyl)phenyl)acetyl | tert-butoxycarbonyl | 93.03 | 9.3 | 551.3 |
| 526 | " | " | H | 97.13 | 6.1 | 451.3 |
| 527 | " | 3-(3,4-dimethoxyphenyl)propanoyl | tert-butoxycarbonyl | 74.37 | 8.4 | 557.3 |

-continued

| Ex | R₁ | R₂ | R₃ | Purity (%) | rt | M + H+ |
|---|---|---|---|---|---|---|
| 528 | " | " | H→* | 92.92 | 5.3 | 457.3 |
| 529 | 2,6-difluorobenzyl | indol-3-yl-CH₂-C(O)-* | *-O-C(O)-O-tBu | 92.92 | 8.8 | 484.3 |
| 530 | " | " | H→* | 92.68 | 5.5 | 384.2 |
| 531 | " | cyclohexyl-(CH₂)₃-C(O)-* | *-O-C(O)-O-tBu | 98.29 | 10.8 | 479.3 |
| 532 | " | " | H→* | 96.39 | 7.0 | 379.3 |
| 533 | " | *-C(O)-(CH₂)₃-thien-2-yl | *-O-C(O)-O-tBu | 99 | 9.5 | 479.2 |
| 534 | " | " | H→* | 99.76 | 6.0 | 379.2 |
| 535 | " | 4-CF₃-C₆H₄-CH₂-C(O)-* | *-O-C(O)-O-tBu | 99.17 | 9.7 | 513.2 |
| 536 | " | " | H→* | 99.74 | 6.3 | 413.2 |
| 537 | " | 3,4-dimethoxyphenyl-(CH₂)₂-C(O)-* | *-O-C(O)-O-tBu | 68.71 | 8.7 | 519.3 |
| 538 | " | " | H→* | 90.09 | 5.4 | 419.3 |
| 539 | 3,3-diphenylpropyl | indol-3-yl-CH₂-C(O)-* | *-O-C(O)-O-tBu | 91.37 | 9.8 | 552.3 |
| 540 | " | " | H→* | 95.39 | 6.6 | 452.3 |
| 541 | " | cyclohexyl-(CH₂)₃-C(O)-* | *-O-C(O)-O-tBu | 98.71 | 11.7 | 547.4 |
| 542 | " | " | H→* | 99.02 | 7.9 | 447.4 |

-continued

| Ex | R₁ | R₂ | R₃ | Purity (%) | rt | M + H+ |
|---|---|---|---|---|---|---|
| 543 | " | *-C(=O)-CH₂CH₂CH₂-(2-thienyl) | *-C(=O)-O-tBu | 79.38 | 10.5 | 547.3 |
| 544 | " | " | H-* | 95.46 | 7.1 | 447.3 |
| 545 | " | 4-(F₃C)-C₆H₄-CH₂-C(=O)-* | *-C(=O)-O-tBu | 95.3 | 10.6 | 581.3 |
| 546 | " | " | H-* | 95.45 | 7.3 | 481.3 |
| 547 | " | 3,4-(MeO)₂-C₆H₃-CH₂CH₂-C(=O)-* | *-C(=O)-O-tBu | 80.92 | 9.8 | 587.3 |
| 548 | " | " | H-* | 92.06 | 6.5 | 487.3 |
| 549 | 3-indolyl-CH₂CH₂-* | cyclohexyl-CH₂CH₂CH₂-C(=O)-* | 4-(HN)-C₆H₄-CH₂-C(=O)-* | 63 | 7.7 | 529.4 |
| 550 | " | " | HN-CH₂CH₂CH₂CH₂-C(=O)-* | 79 | 7.1 | 495.4 |
| 551 | " | *-C(=O)-CH₂CH₂CH₂-(2-thienyl) | 4-(HN)-C₆H₄-CH₂-C(=O)-* | 70 | 6.7 | 529.3 |
| 552 | " | " | HN-CH₂CH₂CH₂CH₂-C(=O)-* | 77 | 6.3 | 495.3 |
| 553 | " | 4-(F₃C)-C₆H₄-CH₂-C(=O)-* | 4-(HN)-C₆H₄-CH₂-C(=O)-* | 61 | 6.9 | 563.3 |
| 554 | " | " | HN-CH₂CH₂CH₂CH₂-C(=O)-* | 69 | 6.5 | 529.3 |
| 555 | " | 3,4-(MeO)₂-C₆H₃-CH₂CH₂-C(=O)-* | 4-(HN)-C₆H₄-CH₂-C(=O)-* | 69 | 6.1 | 569.3 |
| 556 | " | " | HN-CH₂CH₂CH₂CH₂-C(=O)-* | 76 | 5.8 | 535.3 |

-continued

| Ex | R₁ | R₂ | R₃ | Purity (%) | rt | M + H+ |
|---|---|---|---|---|---|---|
| 557 | 3,4-dimethoxyphenethyl | 1H-indol-3-ylacetyl | 4-aminophenylacetyl | 79 | 5.9 | 555.3 |
| 558 | " | " | 5-aminopentanoyl | 88 | 5.6 | 521.3 |
| 559 | " | 4-cyclohexylbutanoyl | 4-aminophenylacetyl | 90.81 | 7.4 | 550.4 |
| 560 | " | " | 5-aminopentanoyl | 95.6 | 6.9 | 516.4 |
| 561 | " | 4-(thiophen-2-yl)butanoyl | 4-aminophenylacetyl | 80.85 | 6.4 | 550.3 |
| 562 | " | " | 5-aminopentanoyl | 85.8 | 6.0 | 516.3 |
| 563 | " | 4-(trifluoromethyl)phenylacetyl | 4-aminophenylacetyl | 92.92 | 6.6 | 584.3 |
| 564 | " | " | 5-aminopentanoyl | 97.26 | 6.3 | 550.3 |
| 565 | " | 3-(3,4-dimethoxyphenyl)propanoyl | 4-aminophenylacetyl | 82.91 | 5.8 | 590.3 |
| 566 | " | " | 5-aminopentanoyl | 87.77 | 5.5 | 556.3 |
| 567 | 2,6-difluorobenzyl | 1H-indol-3-ylacetyl | 4-aminophenylacetyl | 86 | 6.0 | 517.3 |
| 568 | " | " | 5-aminopentanoyl | 83.41 | 5.7 | 483.3 |

-continued

| Ex | R₁ | R₂ | R₃ | Purity (%) | rt | M + H+ |
|---|---|---|---|---|---|---|
| 569 | " | cyclohexyl-(CH₂)₂-C(=O)-* | *-C(=O)-CH₂-C₆H₄-N | 95 | 7.6 | 512.3 |
| 570 | " | " | N-(CH₂)₄-C(=O)-* | 94.08 | 7.1 | 478.4 |
| 571 | " | *-C(=O)-(CH₂)₃-(2-thienyl) | *-C(=O)-CH₂-C₆H₄-N | 87.39 | 6.5 | 512.3 |
| 572 | " | " | N-(CH₂)₄-C(=O)-* | 90.06 | 6.1 | 478.3 |
| 573 | " | 4-F₃C-C₆H₄-CH₂-C(=O)-* | *-C(=O)-CH₂-C₆H₄-N | 85.61 | 6.8 | 546.2 |
| 574 | " | " | N-(CH₂)₄-C(=O)-* | 83.51 | 6.4 | 512.3 |
| 575 | " | 3,4-(MeO)₂-C₆H₃-(CH₂)₂-C(=O)-* | *-C(=O)-CH₂-C₆H₄-N | 78.63 | 5.9 | 552.3 |
| 576 | " | " | N-(CH₂)₄-C(=O)-* | 79.58 | 5.6 | 518.3 |
| 577 | *-(CH₂)₂-CH(C₆H₅)₂ | *-C(=O)-CH₂-(1H-indol-3-yl) | *-C(=O)-CH₂-C₆H₄-N | 84 | 7.1 | 585.3 |
| 578 | " | " | N-(CH₂)₄-C(=O)-* | 91 | 6.7 | 551.3 |
| 579 | " | cyclohexyl-(CH₂)₂-C(=O)-* | *-C(=O)-CH₂-C₆H₄-N | 89.59 | 8.6 | 580.4 |

-continued
| Ex | R₁ | R₂ | R₃ | Purity (%) | rt | M + H+ |
|---|---|---|---|---|---|---|
| 580 | " | " | 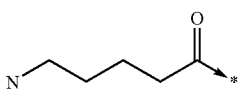 | 97.13 | 7.9 | 546.4 |
| 581 | " | 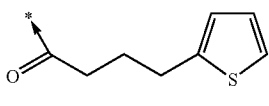 | 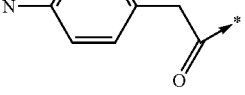 | 83 | 7.6 | 580.3 |
| 582 | " | " | 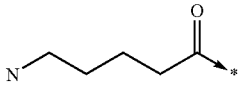 | 92.05 | 7.1 | 546.3 |
| 583 | " | 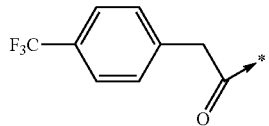 | 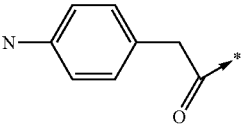 | 86 | 7.8 | 614.3 |
| 584 | " | " | 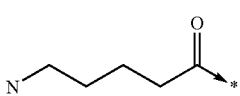 | 95.49 | 7.3 | 580.3 |
| 585 | " | 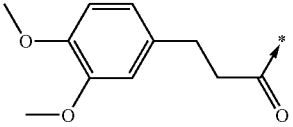 | 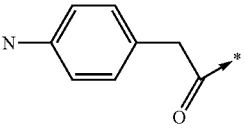 | 77 | 7.0 | 620.3 |
| 586 | " | " | 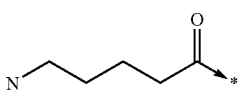 | 91.1 | 6.6 | 586.4 |
| 587 | 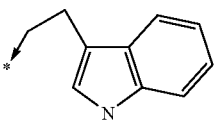 | 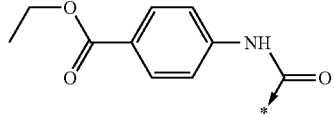 | H—* | 95 | 4.6 | 435 |
| 588 | " |  | " | 90 | 4.4 | 391.3 |
| 589 | " | 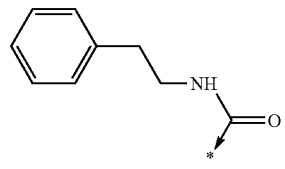 | " | 88 | 5.1 | 435.3 |
| 590 | " | 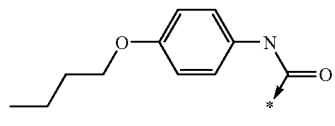 | " | 92 | 4.9 | 447.3 |

-continued
| Ex | R₁ | R₂ | R₃ | Purity (%) | rt | M + H+ |
|---|---|---|---|---|---|---|
| 591 | " | 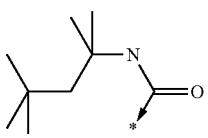 | " | 20.32 | 5.1 | 399.4 |
| 592 | 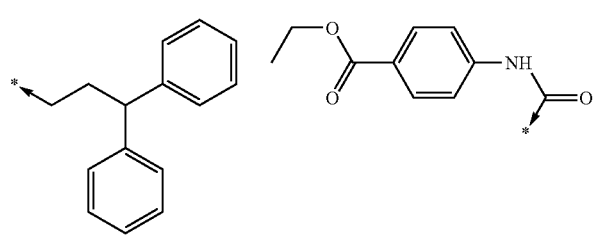 | 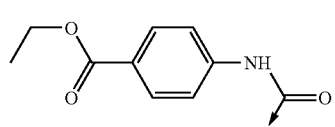 | " | 85 | 5.3 | 486.3 |
| 593 | " | 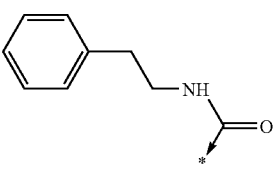 | " | 97 | 5.1 | 442.3 |
| 594 | " | 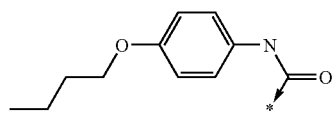 | " | 92 | 5.7 | 486.4 |
| 595 | " | 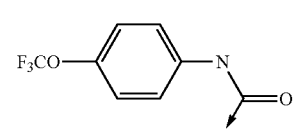 | " | 79 | 5.5 | 498.3 |
| 596 | 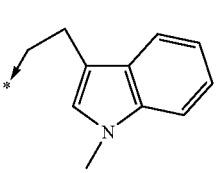 | 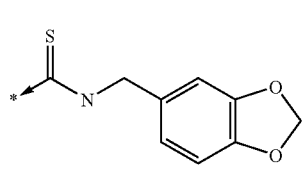 | " | 93.4 | 4.68 | 451.29 |
| 597 | " | 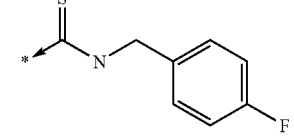 | " | 94.9 | 4.86 | 425.27 |
| 598 | " | 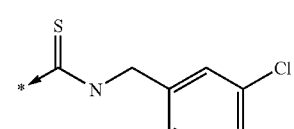 | " | 97.9 | 5.37 | 475.22 |
| 599 | " | 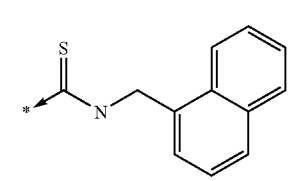 | " | 97.1 | 5.20 | 457.32 |

-continued
| Ex | R₁ | R₂ | R₃ | Purity (%) | rt | M + H+ |
|---|---|---|---|---|---|---|
| 600 | " | 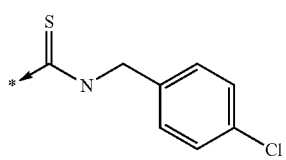 | " | 95.1 | 5.10 | 441.24 |
| 601 | 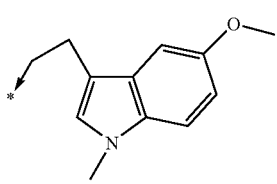 | 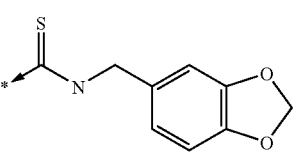 | " | 91.1 | 4.61 | 481.29 |
| 602 | " | 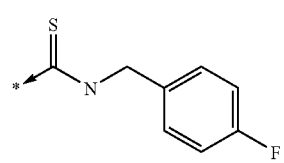 | " | 97.5 | 4.78 | 455.29 |
| 603 | " | 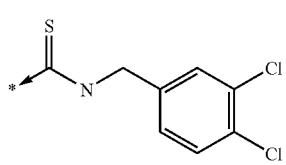 | " | 98.0 | 5.28 | 505.22 |
| 604 | " | 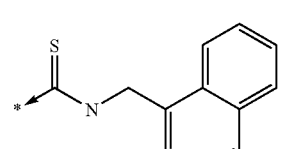 | " | 95.4 | 5.12 | 487.33 |
| 605 | " | 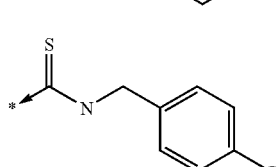 | " | 94.0 | 5.03 | 471.27 |
| 606 | 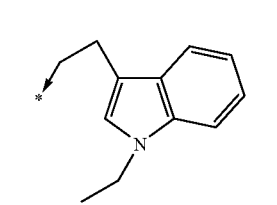 | 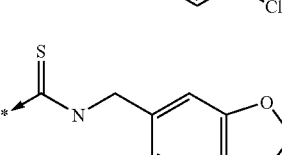 | " | 89.8 | 4.86 | 465.29 |
| 607 | " | 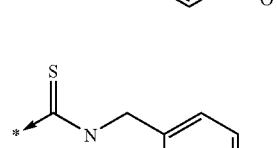 | " | 98.2 | 5.03 | 439.29 |
| 608 | " | 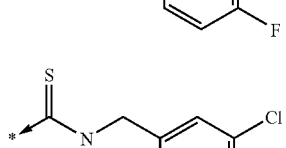 | " | 97.6 | 5.53 | 489.24 |

-continued

| Ex | R₁ | R₂ | R₃ | Purity (%) | rt | M + H+ |
|---|---|---|---|---|---|---|
| 609 | " | *-C(S)-NH-CH₂-(1-naphthyl) | " | 93.3 | 5.36 | 471.34 |
| 610 | " | *-C(S)-NH-CH₂-(4-Cl-C₆H₄) | " | 91.4 | 5.27 | 455.26 |
| 611 | 1-methylindol-3-yl-ethyl | 4-(F₃C)-C₆H₄-N(*)-C(O)-* | CH₃-* | 94 | 4.9 | 459.3 |
| 612 | " | 4-Br-C₆H₄-N(*)-C(O)-* | " | 92.95 | 4.8 | 469.2 |
| 613 | " | 4-Cl-C₆H₄-N(*)-C(O)-* | " | 91.61 | 4.7 | 425.3 |
| 614 | " | 4-(F₃CO)-C₆H₄-N(*)-C(O)-* | " | 92 | 5.0 | 475.3 |
| 615 | " | 4-iPr-C₆H₄-N(*)-C(O)-* | " | 85.2 | 5.1 | 433.4 |
| 616 | " | 4-NC-C₆H₄-N(*)-C(O)-* | " | 83 | 4.2 | 416.3 |
| 617 | " | 4-F-C₆H₄-N(*)-C(O)-* | " | 94.11 | 4.4 | 409.3 |
| 618 | " | 4-I-C₆H₄-N(*)-C(O)-* | " | 93.85 | 5.0 | 517.2 |

-continued
| Ex | R₁ | R₂ | R₃ | Purity (%) | rt | M + H+ |
|---|---|---|---|---|---|---|
| 619 | " | 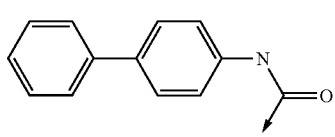 | " | 92.74 | 5.1 | 467.4 |
| 620 | 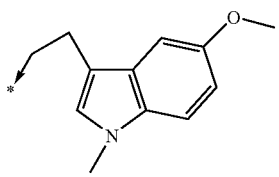 | 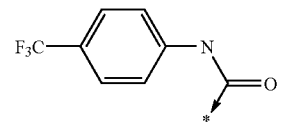 | " | 91 | 4.8 | 489.3 |
| 621 | " | 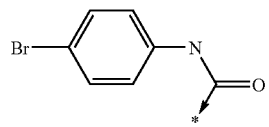 | " | 91.9 | 4.7 | 499.3 |
| 622 | " | 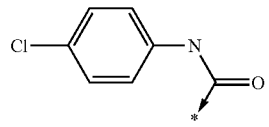 | " | 89.71 | 4.6 | 455.3 |
| 623 | " | 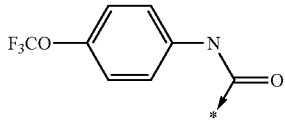 | " | 90 | 4.9 | 505.3 |
| 624 | " | 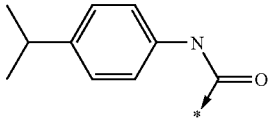 | " | 83.96 | 5.0 | 463.4 |
| 625 | " | 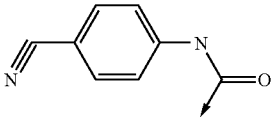 | " | 87 | 4.1 | 446.3 |
| 626 | " | 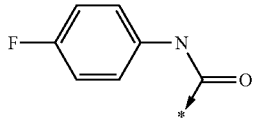 | " | 93.1 | 4.3 | 439.3 |
| 627 | " | 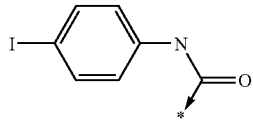 | " | 93.21 | 4.8 | 547.2 |
| 628 | " | 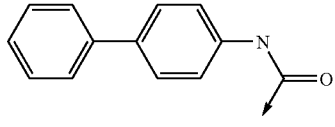 | " | 90.67 | 5.0 | 497.4 |

-continued

| Ex | R₁ | R₂ | R₃ | Purity (%) | rt | M + H+ |
|---|---|---|---|---|---|---|
| 629 | 1-methylindol-3-yl-ethyl | 4-bromophenyl-NHC(=S)- | " | 79.6 | 4.9 | 485.2 |
| 630 | " | 4-azidophenyl-NHC(=S)- | " | 72.8 | 4.8 | 448.3 |
| 631 | " | 4-trifluoromethylphenyl-NHC(=S)- | " | 78.7 | 5.1 | 475.3 |
| 632 | " | diphenylmethyl-NHC(=S)- | " | 97.3 | 5.4 | 511.4 |
| 633 | " | 4-iodophenyl-NHC(=S)- | " | 51.5 | 5.1 | 533.2 |
| 634 | 5-methoxy-1-methylindol-3-yl-ethyl | 4-bromophenyl-NHC(=S)- | " | 76.1 | 4.9 | 515.3 |
| 635 | " | 4-azidophenyl-NHC(=S)- | " | 74.2 | 4.7 | 478.3 |
| 636 | " | 4-trifluoromethylphenyl-NHC(=S)- | " | 76.5 | 5.0 | 505.3 |
| 637 | " | diphenylmethyl-NHC(=S)- | " | 97.7 | 5.3 | 541.4 |

-continued

| Ex | R₁ | R₂ | R₃ | Purity (%) | rt | M + H+ |
|---|---|---|---|---|---|---|
| 638 | " | 4-iodophenyl-NH-C(=S)-* | " | 71.4 | 5.0 | 563.2 |
| 639 | 3-indolyl-CH₂-CH₂-* | benzo[1,3]dioxol-5-yl-CH₂-NH-C(=S)-* | " | 82.54 | 4.4 | 451.3 |
| 640 | " | furan-2-yl-CH₂-NH-C(=S)-* | " | 93.42 | 4.2 | 397.3 |
| 641 | " | Et₂N-CH₂CH₂CH₂-NH-C(=S)-* | " | 98.93 | 2.9 | 430.4 |
| 642 | " | 4-azidophenyl-NH-C(=S)-* | " | 81.46 | 4.5 | 434.3 |
| 643 | " | pentafluorophenyl-NH-C(=S)-* | " | 96.41 | 4.9 | 483.3 |
| 644 | " | 4-chloro-3-nitrophenyl-NH-C(=S)-* | " | 91.55 | 4.7 | 472.3 |
| 645 | " | piperidin-1-yl-CH₂CH₂-NH-C(=S)-* | " | 97.96 | 2.9 | 428.4 |
| 646 | " | naphthalen-1-yl-CH₂-NH-C(=S)-* | " | 96.9 | 5.0 | 425.3 |
| 647 | " | cyclohex-1-enyl-CH₂CH₂-NH-C(=S)-* | " | 95.8 | 4.9 | 457.3 |

-continued
| Ex | R₁ | R₂ | R₃ | Purity (%) | rt | M + H+ |
|---|---|---|---|---|---|---|
| 648 | " | 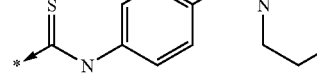 | " | 91.41 | 4.6 | 540.3 |
| 649 |  | 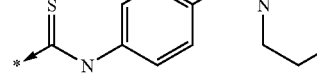 | " | 88.0 | 4.75 | 465.3 |
| 650 | " | 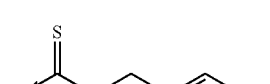 | " | 99.0 | 4.89 | 439.3 |
| 651 | " |  | " | 98.5 | 5.42 | 489.2 |
| 652 | " |  | " | 93.3 | 5.24 | 471.3 |
| 653 | " |  | " | 87.6 | 5.14 | 455.3 |
| 654 | 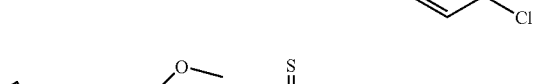 | 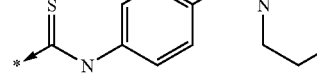 | " | 88.3 | 4.66 | 495.3 |
| 655 | " | 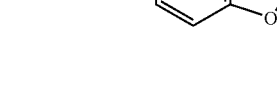 | " | 98.1 | 4.82 | 469.3 |
| 656 | " | 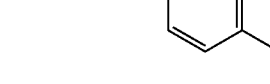 | " | 98.4 | 5.34 | 519.2 |

-continued

| Ex | R₁ | R₂ | R₃ | Purity (%) | rt | M + H+ |
|---|---|---|---|---|---|---|
| 657 | " | *-C(=S)-NH-CH₂-(1-naphthyl) | " | 95.4 | 5.16 | 501.3 |
| 658 | " | *-C(=S)-NH-CH₂-(4-Cl-phenyl) | " | 89.8 | 5.08 | 485.3 |
| 659 | *-CH₂CH₂-(1-methylindol-3-yl) | 4-Cl-phenyl-CH₂-C(=O)-* | H-* | 80.76 | 4.84 | 410.2 |
| 660 | " | (naphth-2-yl)-CH₂-C(=O)-* | " | 61.69 | 4.97 | 426.2 |
| 661 | " | (2-Br-phenyl)-CH₂-C(=O)-* | " | 90.93 | 4.79 | 454.1 |
| 662 | " | (4-F-phenyl)-CH₂-C(=O)-* | " | 91.55 | 4.58 | 394.2 |
| 663 | " | (3-Br-phenyl)-CH₂-C(=O)-* | " | 91.99 | 4.88 | 454.1 |
| 664 | " | (3,5-bis(CF₃)-phenyl)-CH₂CH₂-C(=O)-* | " | 92.79 | 5.55 | 526.2 |
| 665 | " | (4-I-phenyl)-CH₂-C(=O)-* | " | 93.78 | 5.02 | 502.1 |

-continued
| Ex | R₁ | R₂ | R₃ | Purity (%) | rt | M + H+ |
|---|---|---|---|---|---|---|
| 666 | " | 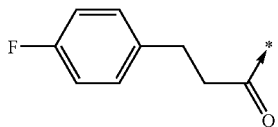 | " | 96.3 | 4.75 | 408.2 |
| 667 | " | 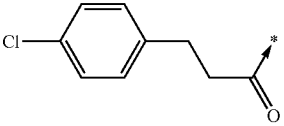 | " | 81.2 | 5.02 | 408.2 |
| 668 | 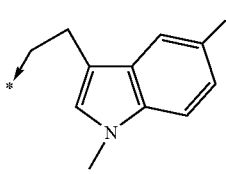 | 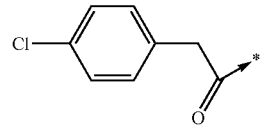 | " | 90.79 | 4.74 | 440.2 |
| 669 | " | 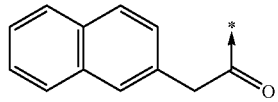 | " | 78.93 | 4.88 | 456.3 |
| 670 | " | 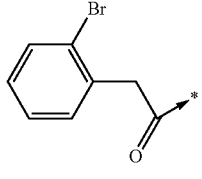 | " | 91.87 | 4.69 | 484.2 |
| 671 | " | 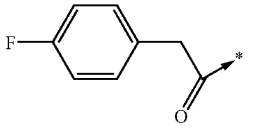 | " | 91.19 | 4.51 | 424.2 |
| 672 | " | 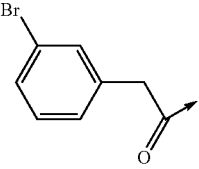 | " | 95.27 | 4.79 | 484.2 |
| 673 | " | 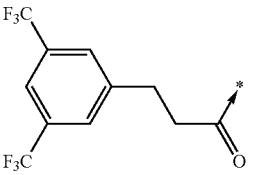 | " | 89.5 | 5.46 | 542.2 |
| 674 | " | 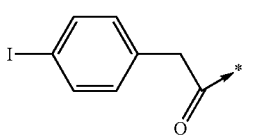 | " | 90.77 | 4.92 | 532.1 |

-continued

| Ex | R₁ | R₂ | R₃ | Purity (%) | rt | M + H+ |
|---|---|---|---|---|---|---|
| 675 | " | 3-(4-fluorophenyl)propanoyl | " | 95.1 | 4.66 | 438.2 |
| 676 | " | 3-(4-chlorophenyl)propanoyl | " | 88.7 | 4.92 | 524.2 |
| 677 | 2-(1-ethyl-1H-indol-3-yl)ethyl | 2-(4-chlorophenyl)acetyl | " | 81.65 | 4.99 | 424.2 |
| 678 | " | 2-(naphthalen-2-yl)acetyl | " | 70.32 | 5.11 | 440.3 |
| 679 | " | 2-(2-bromophenyl)acetyl | " | 90.06 | 4.96 | 468.2 |
| 680 | " | 2-(4-fluorophenyl)acetyl | " | 94.11 | 4.74 | 408.2 |
| 681 | " | 2-(3-bromophenyl)acetyl | " | 93.96 | 5.04 | 468.2 |
| 682 | " | 3-(3,5-bis(trifluoromethyl)phenyl)propanoyl | " | 93.3 | 5.66 | 540.2 |
| 683 | " | 2-(4-iodophenyl)acetyl | " | 94.79 | 5.16 | 516.1 |

-continued

| Ex | R₁ | R₂ | R₃ | Purity (%) | rt | M + H+ |
|---|---|---|---|---|---|---|
| 684 | " | 4-F-C₆H₄-CH₂-CH₂-C(=O)-* | " | 96.5 | 4.9 | 422.3 |
| 685 | " | 4-Cl-C₆H₄-CH₂-CH₂-C(=O)-* | " | 88.2 | 5.19 | 438.2 |
| 686 | 1-methylindol-3-yl-CH₂-CH₂-* | 4-Cl-C₆H₄-CH₂-C(=O)-* | CH₃-* | 87.93 | 4.86 | 424.2 |
| 687 | " | naphth-2-yl-CH₂-C(=O)-* | " | 84.74 | 5 | 440.2 |
| 688 | " | 2-Br-C₆H₄-CH₂-C(=O)-* | " | 95.34 | 4.82 | 468.2 |
| 689 | " | 4-F-C₆H₄-CH₂-C(=O)-* | " | 89.78 | 4.6 | 408.2 |
| 690 | " | 3-Br-C₆H₄-CH₂-C(=O)-* | " | 95.16 | 4.9 | 468.1633 |
| 691 | " | 3,5-(CF₃)₂-C₆H₃-CH₂-CH₂-C(=O)-* | " | 95.6 | 5.56 | 540.2 |
| 692 | " | 4-I-C₆H₄-CH₂-C(=O)-* | " | 95.24 | 5.05 | 516.3 |

-continued
| Ex | R₁ | R₂ | R₃ | Purity (%) | rt | M + H+ |
|---|---|---|---|---|---|---|
| 693 | " | 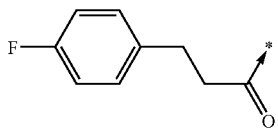 | " | 96.6 | 4.8 | 422.2 |
| 694 | " | 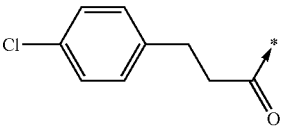 | " | 90.4 | 5.04 | 438.2 |
| 695 | 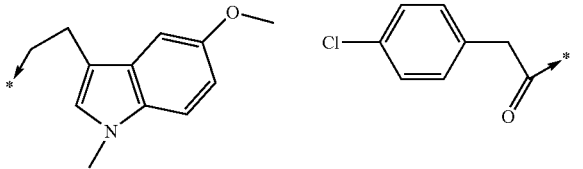 | 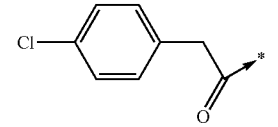 | " | 93.12 | 4.78 | 454.2 |
| 696 | " | 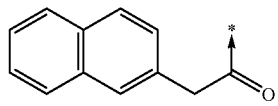 | " | 86.11 | 4.92 | 470.3 |
| 697 | " | 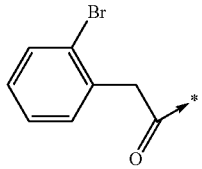 | " | 94.89 | 4.73 | 498.2 |
| 698 | " | 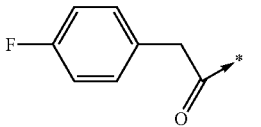 | " | 94.1 | 4.54 | 438.3 |
| 699 | " | 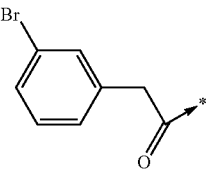 | " | 95.66 | 4.81 | 498.2 |
| 700 | " | 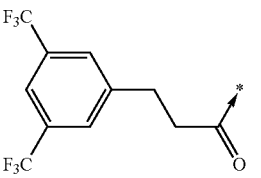 | " | 94.8 | 5.48 | 570.2 |
| 701 | " | 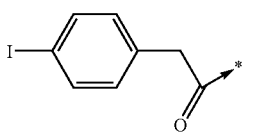 | " | 93.63 | 4.96 | 546.1 |

-continued

| Ex | R₁ | R₂ | R₃ | Purity (%) | rt | M + H+ |
|---|---|---|---|---|---|---|
| 702 | " | 4-F-C₆H₄-CH₂-CH₂-C(=O)-* | " | 96.7 | 4.7 | 452.3 |
| 703 | " | 4-Cl-C₆H₄-CH₂-CH₂-C(=O)-* | " | 85.6 | 4.96 | 468.2 |
| 704 | *-CH₂-CH₂-O-CH₃ | 3,4-(MeO)₂-C₆H₃-S(=O)₂-* | H-* | 78.36 | 3.14 | 359.1 |
| 705 | *-CH₂-CH₂-O-CH₃ | 4-CF₃-C₆H₄-S(=O)₂-* | " | 47.4 | 3.9 | 367.1 |
| 706 | *-(CH₂)₅-CH₃ | 3,4-(MeO)₂-C₆H₃-S(=O)₂-* | " | 69.72 | 4.28 | 385.2 |
| 707 | *-(CH₂)₅-CH₃ | 4-CF₃-C₆H₄-S(=O)₂-* | " | 34.86 | 4.96 | 393.2 |
| 708 | 1-naphthyl-CH₂-* | 4-CF₃-C₆H₄-S(=O)₂-* | " | 37.54 | 4.91 | 449.2 |
| 709 | 4-Br-C₆H₄-CH₂-CH₂-* | 3,4-(MeO)₂-C₆H₃-S(=O)₂-* | " | 81.57 | 4.46 | 483.1 |
| 710 | 4-Br-C₆H₄-CH₂-CH₂-* | 4-CF₃-C₆H₄-S(=O)₂-* | " | 55.98 | 5.12 | 491.1 |
| 711 | *-(CH₂)₃-N(piperazine)N-CH₃ | 3,4-(MeO)₂-C₆H₃-S(=O)₂-* | " | 73.74 | 3.09 | 441.2 |
| 712 | *-(CH₂)₃-N(piperazine)N-CH₃ | 4-CF₃-C₆H₄-S(=O)₂-* | " | 40.19 | 2.85 | 449.2 |

-continued

| Ex | R₁ | R₂ | R₃ | Purity (%) | rt | M + H+ |
|---|---|---|---|---|---|---|
| 713 | *-CH₂CH₂CH₂-N(pyrrolidin-2-one) | 3,4-dimethoxyphenyl-SO₂-* | " | 90.07 | 3.18 | 426.2 |
| 714 | *-CH₂CH₂CH₂-N(pyrrolidin-2-one) | 4-(CF₃)phenyl-SO₂-* | " | 74.98 | 3.84 | 434.2 |
| 715 | *-CH₂-cyclohexyl | 3,4-dimethoxyphenyl-SO₂-* | " | 78.14 | 4.24 | 397.2 |
| 716 | *-CH₂-cyclohexyl | 4-(CF₃)phenyl-SO₂-* | " | 39.87 | 4.92 | 405.2 |
| 717 | *-CH₂-(4-F, 3-CF₃)phenyl | 3,4-dimethoxyphenyl-SO₂-* | " | 57.34 | 4.45 | 477.2 |
| 718 | *-CH₂-(4-F, 3-CF₃)phenyl | 4-(CF₃)phenyl-SO₂-* | " | 37.75 | 5.01 | 485.1 |
| 719 | *-(CH₂)₅-CH₃ | 3,4-dichlorophenyl-NH-C(O)-* | allyl-* | 70.3 | 5.2 | 412.1 |
| 720 | " | " | CH₃-* | 70.7 | 5.0 | 386.1 |
| 721 | " | " | 5,5,8,8-tetramethyl-5,6,7,8-tetrahydronaphthalen-2-yl-C(O)-CH₂-* | 61.9 | 6.3 | 600.3 |
| 722 | " | cyclohexyl-NH-C(O)-* | " | 49.3 | 6.1 | 538.4 |
| 723 | *-CH₂CH₂-C(CH₃)₃ | 3,4-dichlorophenyl-NH-C(O)-* | allyl-* | 65.0 | 5.1 | 412.2 |

-continued
| Ex | R₁ | R₂ | R₃ | Purity (%) | rt | M + H+ |
|---|---|---|---|---|---|---|
| 724 | " | " |  | 44.3 | 4.9 | 386.2 |
| 725 | " | " | 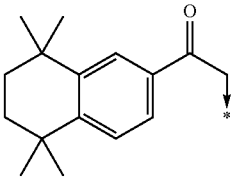 | 49.2 | 6.2 | 600.3 |
| 726 | " | 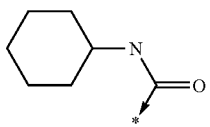 | " | 37.5 | 6.0 | 538.4 |
| 727 | 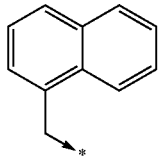 | 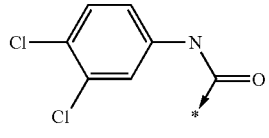 | 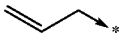 | 87.1 | 5.1 | 468.1 |
| 728 | " | " |  | 84.4 | 4.9 | 442.1 |
| 729 | " | " | 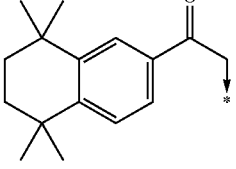 | 82.3 | 6.2 | 656.3 |
| 730 | " | 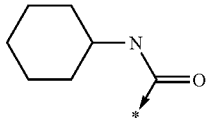 | 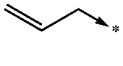 | 93.8 | 4.7 | 406.3 |
| 731 | " | " |  | 80.7 | 4.6 | 380.3 |
| 732 | " | " | 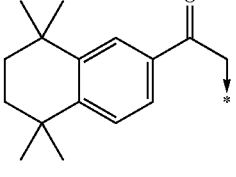 | 84.1 | 5.9 | 594.3 |
| 733 | 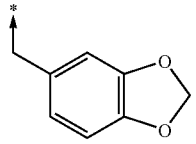 | 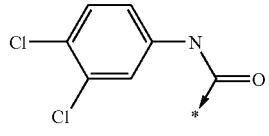 | 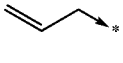 | 67.9 | 4.7 | 462.1 |
| 734 | " | " |  | 66.9 | 4.6 | 436.1 |

-continued

| Ex | R₁ | R₂ | R₃ | Purity (%) | rt | M + H+ |
|---|---|---|---|---|---|---|
| 735 | " | " | tetramethyltetrahydronaphthalenyl-C(O)-CH₂-* | 56.8 | 5.9 | 650.2 |
| 736 | " | cyclohexyl-N(C(O)-*)- | allyl-* | 88.1 | 4.3 | 400.3 |
| 737 | " | " | CH₃-* | 82.8 | 4.1 | 374.3 |
| 738 | " | " | tetramethyltetrahydronaphthalenyl-C(O)-CH₂-* | 51.4 | 5.6 | 588.3 |
| 739 | 3,5-dimethylbenzyl-* | 3,4-dichlorophenyl-N(C(O)-*)- | allyl-* | 77.7 | 5.1 | 446.2 |
| 740 | " | " | CH₃-* | 76.1 | 4.9 | 420.2 |
| 741 | " | " | tetramethyltetrahydronaphthalenyl-C(O)-CH₂-* | 67.1 | 6.2 | 634.3 |
| 742 | " | cyclohexyl-N(C(O)-*)- | allyl-* | 88.9 | 4.7 | 384.3 |
| 743 | " | " | CH₃-* | 79.3 | 4.5 | 358.3 |
| 744 | " | " | tetramethyltetrahydronaphthalenyl-C(O)-CH₂-* | 65.1 | 5.9 | 572.4 |

-continued

| Ex | R₁ | R₂ | R₃ | Purity (%) | rt | M + H+ |
|---|---|---|---|---|---|---|
| 745 | *~~~~CH₃ (hexyl) | oxindole-CH₂-C(=O)-* | allyl | 80.0 | 4.0 | 398.3 |
| 746 | " | " | CH₃-* | 76.9 | 3.8 | 372.3 |
| 747 | " | " | 5,5,8,8-tetramethyl-tetrahydronaphthalenyl-C(=O)-CH₂-* | 42.7 | 5.8 | 586.4 |
| 748 | " | " | 5-NO₂-furan-2-yl-CH₂-* | 64.6 | 4.4 | 483.3 |
| 749 | " | 2-methyl-3,4-dihydronaphthalenyl-CH₂-C(=O)-* | allyl | 87.4 | 5.3 | 409.3 |
| 750 | " | " | CH₃-* | 71.0 | 5.1 | 383.3 |
| 751 | " | " | 5,5,8,8-tetramethyl-tetrahydronaphthalenyl-C(=O)-CH₂-* | 59.8 | 6.7 | 597.4 |
| 752 | " | " | 5-NO₂-furan-2-yl-CH₂-* | 84.4 | 5.6 | 494.3 |
| 753 | neopentyl-CH₂-* | oxindole-CH₂-C(=O)-* | allyl | 80.1 | 3.9 | 398.3 |
| 754 | " | " | CH₃-* | 63.1 | 3.7 | 372.3 |

-continued
| Ex | R₁ | R₂ | R₃ | Purity (%) | rt | M + H+ |
|---|---|---|---|---|---|---|
| 755 | " | " | 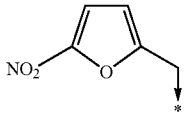 | 64.4 | 4.3 | 483.3 |
| 756 | " | 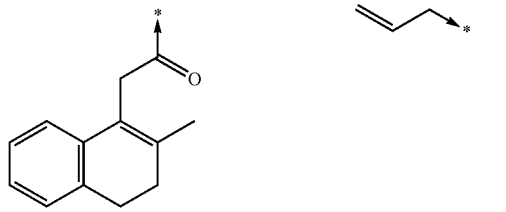 | 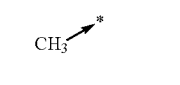 | 84.6 | 5.3 | 409.3 |
| 757 | " | " | 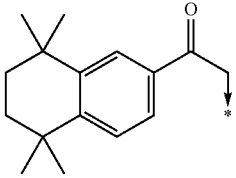 | 59.6 | 5.0 | 383.3 |
| 758 | " | " | 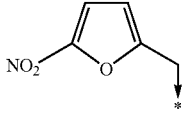 | 52.9 | 6.6 | 597.4 |
| 759 | " | " | 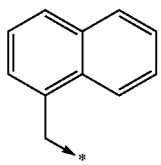 | 81.6 | 5.5 | 494.3 |
| 760 | 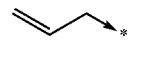 | " | 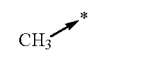 | 75.3 | 5.3 | 465.3 |
| 761 | " | " | 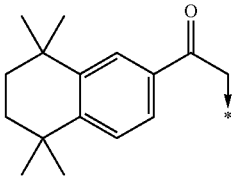 | 60.3 | 5.1 | 439.3 |
| 762 | " | " | 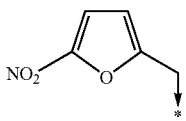 | 61.8 | 6.6 | 653.4 |
| 763 | " | " | 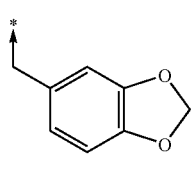 | 74.4 | 5.6 | 550.3 |
| 764 | 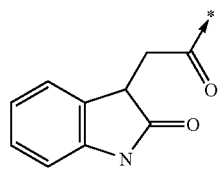 | 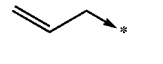 | | 74.5 | 3.6 | 448.2 |

-continued
| Ex | R₁ | R₂ | R₃ | Purity (%) | rt | M + H+ |
|---|---|---|---|---|---|---|
| 765 | " | " |  | 51.3 | 3.4 | 422.2 |
| 766 | " | " | 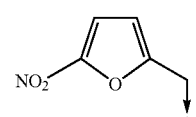 | 58.8 | 3.9 | 533.2 |
| 767 | " | 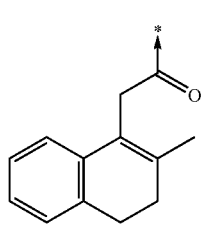 |  | 86.2 | 4.8 | 459.3 |
| 768 | " | " | 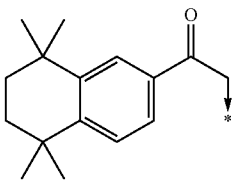 | 63.2 | 4.6 | 433.3 |
| 769 | " | " | 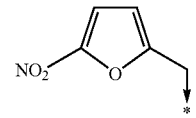 | 60.1 | 6.2 | 647.4 |
| 770 | " | " | 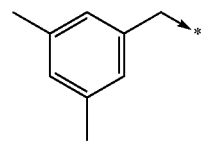 | 83.5 | 5.1 | 544.2 |
| 771 | 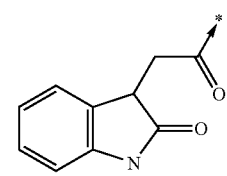 |  | 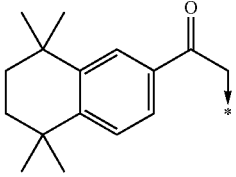 | 68.1 | 4.1 | 432.3 |
| 772 | " | " | 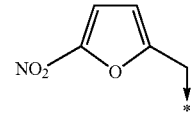 | 63.8 | 3.9 | 406.2 |
| 773 | " | " |  | 41.1 | 5.8 | 620.4 |
| 774 | " | " |  | 62.8 | 4.4 | 517.2 |

-continued

| Ex | R₁ | R₂ | R₃ | Purity (%) | rt | M + H+ |
|---|---|---|---|---|---|---|
| 775 | " | (2-methyl-3,4-dihydronaphthalen-1-yl)acetyl group | allyl | 85.5 | 5.4 | 443.3 |
| 776 | " | " | CH₃ | 62.5 | 5.2 | 417.3 |
| 777 | " | " | (5,5,8,8-tetramethyl-5,6,7,8-tetrahydronaphthalen-2-yl)carbonylmethyl | 66.0 | 6.7 | 631.4 |
| 778 | " | " | (5-nitrofuran-2-yl)methyl | 87.7 | 5.6 | 528.3 |

Pharmacological Study

The compounds of the present invention can and have been tested as regards their affinity for different sub-types of somatostatin receptors according to the procedures described below.

Study of the Affinity for the Sub-Types of Human Somatostatin Receptors:

The affinity of a compound of the invention for sub-types of human somatostatin receptors 1 to 5 ($sst_1$, $sst_2$, $sst_3$, $sst_4$ and $sst_5$, respectively) is determined by measurement of the inhibition of the bond of [$^{125}$I-Tyr$^{11}$]SRIF-14 to transfected CHO-K1 cells.

The gene of the $sst_1$ receptor of human somatostatin has been cloned in the form of a genomic fragment. A segment PstI-XmnI of 1.5 Kb containing 100 bp of the non transcribed 5' region, 1.17 Kb of the coding region in totality, and 230 bp of the non transcribed 3' region is modified by the addition of the linker BglII. The resulting DNA fragment is subcloned in the BamHI site of a pCMV-81 in order to produce the expression plasmid in mammals (provided by Dr. Graeme Bell, Univ. Chicago). A cloned cell line expressing in a stable fashion the $sst_1$ receptor is obtained by transfection in CHO-K1 cells (ATCC) using the calcium phosphate co-precipitation method. The plasmid pRSV-neo (ATCC) is included as selection marker. Cloned cell lines were selected in an RPMI 1640 medium containing 0.5 mg/ml of G418 (Gibco), followed by circular cloning and multiplication in culture.

The gene of the $sst_2$ receptor of human somatostatin, isolated in the form of a genomic fragment of DNA of 1.7 Kb BamHI-HindIII and subcloned in a plasmid vector pGEM3Z (Promega), was provided by Dr. G. Bell (Univ. of Chicago). The expression vector of the mammalian cells is constructed by inserting the BamHI-HindIII fragment of 1.7 Kb in endonuclease restriction sites compatible with the plasmid pCMV5. A cloned cell line is obtained by transfection in CHO-K1 cells using the calcium phosphate co-precipitation method. The plasmid pRSV-neo is included as selection marker.

The $sst_3$ receptor is isolated as a genomic fragment, and the complete coding sequence is contained in a BamHI/HindIII fragment of 2.4 Kb. The expression plasmid in mammals, pCMV-h3, is constructed by insertion of the NcoI-HindIII fragment of 2.0 Kb in the EcoR1 site of the vector pCMV after modification of the terminations and addition of EcoR1 linkers. A cloned cell line expressing in a stable fashion the $sst_3$ receptor is obtained by transfection in CHO-K1 cells (ATCC) by the calcium phosphate co-precipitation method. The plasmid pRSV-neo (ATCC) is included as selection marker. Cloned cell lines were selected in an RPMI 1640 medium containing 0.5 mg/ml of G418 (Gibco), followed by circular cloning and multiplication in culture.

The expression plasmid of the human $sst_4$ receptor, pCMV-HX, was provided by Dr. Graeme Bell (Univ. Chicago). This vector contains the genomic fragment coding for the human $sst_4$ receptor of 1.4 Kb NheI-NheI, 456 pb of the non transcribed 5' region, and 200 pb of the non transcribed 3' region, cloned in the XbaI/EcoR1 sites of PCMV-HX. A cloned cell line expressing in a stable fashion the $sst_4$ receptor is obtained by transfection in CHO-K1 (ATCC) cells by the calcium phosphate co-precipitation method. The plasmid pRSV-neo (ATCC) is included as selection marker. The cloned cell lines were selected in an RPMI 1640 medium containing 0.5 mg/ml of G418 (Gibco), followed by circular cloning and multiplication in culture.

The gene corresponding to the human $sst_5$ receptor, obtained by the PCR method using a genomic λ clone as probe, was provided by Dr. Graeme Bell (Univ. Chicago). The resulting PCR fragment of 1.2 Kb contains 21 base pairs of the non transcribed 5' region, the coding region in totality, and 55 pb of the non transcribed 3' region. The clone is inserted in an EcoR1 site of the plasmid pBSSK(+). The insert is recovered in the form of a HindIII-XbaI fragment of 1.2 Kb for subcloning in an expression vector in mammals, pCVM5. A cloned cell lines expressing in a stable fashion the $sst_5$ receptor is obtained by transfection in CHO-K1 cells (ATCC) by the calcium phosphate co-precipitation method. The plasmid pRSV-neo (ATCC) is included as selection marker. The cloned cell lines were selected in an RPMI 1640 medium containing 0.5 mg/ml of G418 (Gibco), followed by circular cloning and multiplication in culture.

The CHO-K1 cells which express in a stable fashion one of the human sst receptors are cultured in an RPMI 1640 medium containing 10% of foetal calf serum and 0.4 mg/ml of geneticin. The cells are collected with EDTA at 0.5 mM and centrifuged at 500 g for approximately 5 minutes at approximately 4° C. The pellet is resuspended in Tris 50 mM buffer medium at pH 7.4 and centrifuged twice at 500 g for approximately 5 minutes at approximately 4° C. The cells are lysed by sonication then centrifuged at 39000 g for approximately 10 minutes at 4° C. The pellet is resuspended in the same buffer and centrifuged at 50000 g for approximately 10 minutes at approximately 4° C. and the cell membranes in the pellet obtained are stored at −80° C.

The competitive inhibition tests of the bond with [$^{125}$I-Tyr$^{11}$]SRIF-14 are carried out in duplicate in 96-well polypropylene plates. The cell membranes (10 μg protein/well) are incubated with [$^{125}$I-Tyr$^{11}$]SRIF-14 (0.05 nM) for approximately 60 min. at approximately 37° C. in a HEPES 50 mM buffer (pH 7.4) containing BSA 0.2%, MgCl$_2$ 5 mM, Trasylol 200 KIU/ml, bacitricin 0.02 mg/ml and phenylmethylsulphonyl fluoride 0.02 mg/ml.

The bound [$^{125}$I-Tyr$^{11}$]SRIF-14 is separated from the free [$^{125}$I-Tyr$^{11}$]SRIF-14 by immediate filtration through GF/C glass fibre filter plates (Unifilter, Packard) pre-impregnated with 0.1% of polyethylenimine (P.E.I.), using a Filtermate 196 (Packard). The filters are washed with 50 mM HEPES buffer at approximately 0-4° C. for approximately 4 seconds and their radioactivity is determined using a counter (Packard Top Count).

The specific bond is obtained by subtracting the non-specific bond (determined in the presence of 0.1 μM of SRIF-14) from the total bond. The data relative to the bond are analyzed by computer-aided non-linear regression analysis (MDL) and the values of the inhibition constants (Ki) are determined.

Determination of the agonist or antagonist character of a compound of the present invention is carried out using the test described below.

Functional Test Inhibition of Production of Intracellular cAMP:

CHO-K1 cells expressing the sub-types of human somatostatin receptors (SRIF-14) are cultured in 24-well plates in an RPMI 1640 medium with 10% of foetal calf serum and 0.4 mg·ml of geneticin. The medium is changed the day preceding the experiment.

The cells at a rate of $10^5$ cells/well are washed twice with 0.5 ml of new RPMI medium comprising 0.2% BSA completed by 0.5 mM of 3-isobutyl-1-methylxanthine (IBMX) and incubated for approximately 5 min at approximately 37° C.

the production of cyclic AMP is stimulated by the addition of 1 mM of forskolin (FSK) for 15-30 minutes at approximately 37° C.

the inhibitory effect of the somatostatin of an agonist compound is measured by the simultaneous addition of FSK (1 μM), SRIF-14 ($10^{-12}$ M to $10^{-6}$ M) and of the compound to be tested ($10^{-10}$ M to $10^{-5}$ M).

the antagonist effect of a compound is measured by the simultaneous addition of FSK (1 μM), SRIF-14 (1 to 10 nM) and of the compound to be tested ($10^{-10}$ M to $10^{-5}$ M).

The reaction medium is eliminated and 200 ml of 0.1 N HCl are added. The quantity of cAMP is measured by a radioimmunological test (FlashPlate SMP001A kit, New England Nuclear).

Results:

The tests carried out according to the protocols described above have demonstrated that the products of general formula (I) defined in the present Application have a good affinity for at least one of the sub-types of somatostatin receptors, the inhibition constant $K_i$ being lower than micromolar for certain exemplified compounds.

The invention claimed is:

1. Compounds of the general formula:

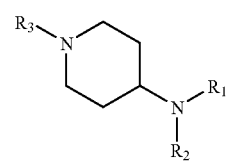

I in racemic, enantiomeric form or all combinations of these forms, in which:
  $R_1$ represents a —(CH$_2$)$_m$—Z$_{12}$ radical in which $Z_{12}$ represents optionally substituted aryl;
  $R_2$ represents a radical of formula —C(Y)NHX$_1$, wherein $X_1$ represents a (CH$_2$)$_p$—Z$_{22}$ radical in which $Z_{22}$ represents aryl optionally substituted;
  $R_3$ represents an optionally substituted alkyl;
  Y represents an oxygen or a sulphur atom;
  m is an integer from 1 to 6; and
  p is an integer from 0 to 6;
  or their addition salts with pharmaceutically acceptable mineral or organic acids.

* * * * *